(12) United States Patent
Weber et al.

(10) Patent No.: US 8,128,689 B2
(45) Date of Patent: Mar. 6, 2012

(54) BIOERODIBLE ENDOPROSTHESIS WITH BIOSTABLE INORGANIC LAYERS

(75) Inventors: Jan Weber, Maastricht (NL); Liliana Atanasoska, Edina, MN (US); Scott Schewe, Eden Prairie, MN (US)

(73) Assignee: Boston Scientific SciMed, Inc., Maple Grove, MN (US)

( * ) Notice: Subject to any disclaimer, the term of this patent is extended or adjusted under 35 U.S.C. 154(b) by 598 days.

(21) Appl. No.: 11/855,542

(22) Filed: Sep. 14, 2007

(65) Prior Publication Data

US 2008/0071352 A1 Mar. 20, 2008

Related U.S. Application Data

(60) Provisional application No. 60/845,135, filed on Sep. 15, 2006.

(51) Int. Cl.
*A61F 2/06* (2006.01)

(52) U.S. Cl. .................................................. 623/1.42

(58) Field of Classification Search ........ 623/1.38–1.54, 623/1.15, 1.13, 23.7, 23.71, 23.72, 23.73, 623/23.74, 23.75, 23.76
See application file for complete search history.

(56) References Cited

U.S. PATENT DOCUMENTS

| | | |
|---|---|---|
| 2,950,187 A | 8/1960 | Ototani |
| 3,560,362 A | 2/1971 | Kasamatsu et al. |
| 3,569,660 A | 3/1971 | Houldcroft |
| 3,687,135 A | 8/1972 | Stroganov et al. |
| 3,758,396 A | 9/1973 | Vieth et al. |
| 3,868,578 A | 2/1975 | Oldham |
| 3,910,819 A | 10/1975 | Rembaum et al. |
| 3,948,254 A | 4/1976 | Zaffaroni |
| 3,952,334 A | 4/1976 | Bokros et al. |
| 3,993,072 A | 11/1976 | Zaffaroni |
| 4,002,877 A | 1/1977 | Banas |
| 4,101,984 A | 7/1978 | MacGregor |
| 4,143,661 A | 3/1979 | LaForge et al. |
| 4,202,055 A | 5/1980 | Reiner et al. |
| 4,237,559 A | 12/1980 | Borom |
| 4,308,868 A | 1/1982 | Jhabvala |
| 4,334,327 A | 6/1982 | Lyman et al. |
| 4,401,546 A | 8/1983 | Nakamura et al. |
| 4,532,929 A | 8/1985 | Mattei et al. |
| 4,539,061 A | 9/1985 | Sagiv |
| 4,542,539 A | 9/1985 | Rowe et al. |
| 4,585,652 A | 4/1986 | Miller et al. |
| 4,634,502 A | 1/1987 | Callahan et al. |
| 4,655,771 A | 4/1987 | Wallsten |
| 4,657,544 A * | 4/1987 | Pinchuk ................. 623/1.39 |

(Continued)

FOREIGN PATENT DOCUMENTS

AU 739 507 11/1998

(Continued)

OTHER PUBLICATIONS

International Search Report and Written Opinion in PCT/US2007/078476, mailed Jan. 28, 2009, 29 pages.

(Continued)

*Primary Examiner* — Alvin J. Stewart
(74) *Attorney, Agent, or Firm* — Fish & Richardson P.C.

(57) ABSTRACT

Medical devices such as endoprostheses (e.g., stents) containing one or more biostable layers (e.g., biostable inorganic layers) and a biodegradable underlying structure are disclosed.

21 Claims, 6 Drawing Sheets

U.S. PATENT DOCUMENTS

| | | | |
|---|---|---|---|
| 4,665,896 A | 5/1987 | LaForge et al. | |
| 4,705,502 A | 11/1987 | Patel | |
| 4,713,070 A * | 12/1987 | Mano | 623/1.39 |
| 4,725,273 A * | 2/1988 | Kira | 623/1.33 |
| 4,733,665 A | 3/1988 | Palmaz | |
| 4,767,418 A * | 8/1988 | Deininger et al. | 623/1.39 |
| 4,784,659 A | 11/1988 | Fleckenstein et al. | |
| 4,800,882 A | 1/1989 | Gianturco | |
| 4,804,382 A * | 2/1989 | Turina et al. | 623/1.41 |
| 4,886,062 A | 12/1989 | Wiktor | |
| 4,954,126 A | 9/1990 | Wallsten | |
| 4,976,692 A | 12/1990 | Atad | |
| 4,994,071 A | 2/1991 | MacGregor | |
| 5,024,671 A | 6/1991 | Tu et al. | |
| 5,059,211 A | 10/1991 | Stack et al. | |
| 5,061,275 A | 10/1991 | Wallsten et al. | |
| 5,061,914 A | 10/1991 | Busch et al. | |
| 5,073,365 A | 12/1991 | Katz et al. | |
| 5,079,203 A | 1/1992 | Pinnavaia | |
| 5,091,024 A | 2/1992 | DeBold et al. | |
| 5,091,205 A | 2/1992 | Fan | |
| 5,102,403 A | 4/1992 | Alt | |
| 5,120,322 A | 6/1992 | Davis et al. | |
| 5,125,971 A | 6/1992 | Nonami et al. | |
| 5,147,370 A | 9/1992 | McNamara et al. | |
| 5,163,958 A | 11/1992 | Pinchuk | |
| 5,195,969 A | 3/1993 | Wang et al. | |
| 5,205,921 A | 4/1993 | Shirkanzadeh | |
| 5,234,457 A | 8/1993 | Andersen | |
| 5,236,413 A | 8/1993 | Feiring | |
| 5,236,447 A * | 8/1993 | Kubo et al. | 623/1.13 |
| 5,270,086 A | 12/1993 | Hamlin | |
| 5,279,292 A | 1/1994 | Baumann et al. | |
| 5,290,585 A | 3/1994 | Elton | |
| 5,292,558 A | 3/1994 | Heller et al. | |
| 5,302,414 A | 4/1994 | Alkhimov et al. | |
| 5,304,121 A | 4/1994 | Sahatjian | |
| 5,304,195 A | 4/1994 | Twyford, Jr. et al. | |
| 5,306,286 A | 4/1994 | Stack et al. | |
| 5,314,453 A | 5/1994 | Jeutter | |
| 5,322,520 A | 6/1994 | Milder | |
| 5,342,348 A | 8/1994 | Kaplan | |
| 5,348,553 A | 9/1994 | Whitney | |
| 5,356,433 A | 10/1994 | Rowland et al. | |
| 5,360,440 A | 11/1994 | Andersen | |
| 5,366,504 A | 11/1994 | Andersen et al. | |
| 5,380,298 A | 1/1995 | Zabetakis et al. | |
| 5,383,935 A | 1/1995 | Shirkhanzadeh | |
| 5,385,776 A | 1/1995 | Maxfield et al. | |
| 5,397,307 A | 3/1995 | Goodin | |
| 5,405,367 A | 4/1995 | Schulman et al. | |
| 5,421,955 A | 6/1995 | Lau et al. | |
| 5,439,446 A | 8/1995 | Barry | |
| 5,443,458 A | 8/1995 | Eury | |
| 5,443,496 A | 8/1995 | Schwartz et al. | |
| 5,443,500 A * | 8/1995 | Sigwart | 623/1.17 |
| 5,449,373 A | 9/1995 | Pinchasik et al. | |
| 5,449,382 A * | 9/1995 | Dayton | 623/1.15 |
| 5,458,627 A | 10/1995 | Baranowski, Jr. et al. | |
| 5,462,575 A | 10/1995 | Del Corso | |
| 5,464,450 A * | 11/1995 | Buscemi et al. | 623/1.2 |
| 5,464,650 A | 11/1995 | Berg et al. | |
| 5,468,574 A | 11/1995 | Ehrenberg et al. | |
| 5,474,797 A | 12/1995 | Sioshansi et al. | |
| 5,500,013 A | 3/1996 | Buscemi et al. | |
| 5,514,154 A | 5/1996 | Lau et al. | |
| 5,527,337 A | 6/1996 | Stack et al. | |
| 5,536,573 A | 7/1996 | Rubner et al. | |
| 5,545,208 A * | 8/1996 | Wolff et al. | 623/1.22 |
| 5,549,664 A * | 8/1996 | Hirata et al. | 623/1.48 |
| 5,551,954 A | 9/1996 | Buscemi et al. | |
| 5,578,075 A * | 11/1996 | Dayton | 623/1.15 |
| 5,587,200 A | 12/1996 | Lorenz et al. | |
| 5,587,507 A | 12/1996 | Kohn et al. | |
| 5,591,222 A | 1/1997 | Susawa et al. | |
| 5,591,224 A | 1/1997 | Schwartz et al. | |
| 5,599,352 A | 2/1997 | Dinh et al. | |
| 5,603,556 A | 2/1997 | Klink | |
| 5,605,696 A | 2/1997 | Eury et al. | |
| 5,607,463 A * | 3/1997 | Schwartz et al. | 623/1.44 |
| 5,609,629 A | 3/1997 | Fearnot et al. | |
| 5,614,549 A | 3/1997 | Greenwald et al. | |
| 5,624,411 A | 4/1997 | Tuch | |
| 5,628,787 A | 5/1997 | Mayer | |
| 5,629,077 A | 5/1997 | Turnland et al. | |
| 5,632,771 A | 5/1997 | Boatman et al. | |
| 5,632,840 A | 5/1997 | Campbell | |
| 5,649,951 A * | 7/1997 | Davidson | 606/198 |
| 5,658,327 A | 8/1997 | Altman et al. | |
| 5,672,242 A | 9/1997 | Jen | |
| 5,674,192 A | 10/1997 | Sahatjian et al. | |
| 5,674,242 A | 10/1997 | Phan | |
| 5,676,685 A | 10/1997 | Razavi | |
| 5,679,440 A | 10/1997 | Kubota | |
| 5,690,670 A * | 11/1997 | Davidson | 606/198 |
| 5,693,085 A | 12/1997 | Buirge et al. | |
| 5,693,928 A | 12/1997 | Egitto et al. | |
| 5,697,967 A | 12/1997 | Dinh et al. | |
| 5,700,286 A | 12/1997 | Tartaglia et al. | |
| 5,716,981 A | 2/1998 | Hunter et al. | |
| 5,721,049 A | 2/1998 | Marcolongo et al. | |
| 5,725,570 A | 3/1998 | Heath | |
| 5,733,925 A | 3/1998 | Kunz et al. | |
| 5,741,331 A | 4/1998 | Pinchuk | |
| 5,744,515 A | 4/1998 | Clapper | |
| 5,749,809 A | 5/1998 | Lin | |
| 5,749,880 A | 5/1998 | Banas et al. | |
| 5,758,562 A | 6/1998 | Thompson | |
| 5,759,192 A | 6/1998 | Saunders | |
| 5,761,775 A | 6/1998 | Legome et al. | |
| 5,769,883 A | 6/1998 | Buscemi et al. | |
| 5,769,884 A | 6/1998 | Solovay | |
| 5,773,925 A | 6/1998 | Kimura et al. | |
| 5,776,184 A | 7/1998 | Tuch | |
| 5,779,904 A | 7/1998 | Ruderman et al. | |
| 5,780,807 A | 7/1998 | Saunders | |
| 5,788,626 A * | 8/1998 | Thompson | 623/1.15 |
| 5,788,687 A | 8/1998 | Batich et al. | |
| 5,788,979 A | 8/1998 | Alt et al. | |
| 5,797,898 A | 8/1998 | Santini, Jr. et al. | |
| 5,800,511 A | 9/1998 | Mayer | |
| 5,815,904 A | 10/1998 | Clubb et al. | |
| 5,817,046 A | 10/1998 | Glickman | |
| 5,824,045 A | 10/1998 | Alt | |
| 5,824,048 A | 10/1998 | Tuch | |
| 5,824,077 A | 10/1998 | Mayer | |
| 5,830,217 A | 11/1998 | Ryan | |
| 5,833,715 A | 11/1998 | Vachon et al. | |
| 5,837,007 A | 11/1998 | Altman et al. | |
| 5,837,275 A * | 11/1998 | Burrell et al. | 424/409 |
| 5,840,387 A | 11/1998 | Berlowitz-Tarrant et al. | |
| 5,843,089 A | 12/1998 | Sahatjian et al. | |
| 5,843,172 A | 12/1998 | Yan | |
| 5,852,277 A | 12/1998 | Gustafson | |
| 5,854,382 A * | 12/1998 | Loomis | 528/354 |
| 5,858,556 A | 1/1999 | Eckert et al. | |
| 5,869,140 A | 2/1999 | Blohowiak et al. | |
| 5,873,904 A * | 2/1999 | Ragheb et al. | 623/1.13 |
| 5,876,756 A | 3/1999 | Takada et al. | |
| 5,879,697 A | 3/1999 | Ding et al. | |
| 5,880,661 A | 3/1999 | Davidson et al. | |
| 5,882,335 A | 3/1999 | Leone et al. | |
| 5,891,108 A * | 4/1999 | Leone et al. | 604/264 |
| 5,891,191 A | 4/1999 | Stinson | |
| 5,899,935 A | 5/1999 | Ding | |
| 5,902,266 A | 5/1999 | Leone et al. | |
| 5,906,759 A | 5/1999 | Richter | |
| 5,907,893 A | 6/1999 | Zadno-Azizi et al. | |
| 5,922,005 A | 7/1999 | Richter et al. | |
| 5,922,021 A | 7/1999 | Jang | |
| 5,928,247 A | 7/1999 | Barry et al. | |
| 5,935,506 A | 8/1999 | Schmitz et al. | |
| 5,938,903 A | 8/1999 | Broderick | |
| 5,941,843 A | 8/1999 | Atanasoska et al. | |
| 5,951,458 A | 9/1999 | Hastings et al. | |
| 5,951,881 A | 9/1999 | Rogers et al. | |
| 5,954,706 A | 9/1999 | Sahatjian | |

| Patent | | Date | Inventor |
|---|---|---|---|
| 5,957,975 | A | 9/1999 | Lafont et al. |
| 5,958,440 | A * | 9/1999 | Burrell et al. ................. 424/409 |
| 5,961,547 | A | 10/1999 | Razavi |
| 5,968,091 | A | 10/1999 | Pinchuk et al. |
| 5,968,092 | A | 10/1999 | Buscemi et al. |
| 5,972,027 | A | 10/1999 | Johnson |
| 5,972,192 | A | 10/1999 | Dubin et al. |
| 5,976,169 | A | 11/1999 | Imran |
| 5,976,454 | A | 11/1999 | Sterzel et al. |
| 5,977,204 | A | 11/1999 | Boyan et al. |
| 5,980,554 | A | 11/1999 | Lenker et al. |
| 5,980,564 | A | 11/1999 | Stinson |
| 5,980,566 | A * | 11/1999 | Alt et al. ....................... 623/23.7 |
| 6,001,125 | A | 12/1999 | Golds et al. |
| 6,013,591 | A * | 1/2000 | Ying et al. .......................... 501/1 |
| 6,017,553 | A * | 1/2000 | Burrell et al. ................. 424/405 |
| 6,017,577 | A | 1/2000 | Hostettler et al. |
| 6,021,347 | A | 2/2000 | Herbst et al. |
| 6,025,036 | A | 2/2000 | McGill et al. |
| 6,027,742 | A * | 2/2000 | Lee et al. ....................... 424/422 |
| 6,034,295 | A | 3/2000 | Rehberg et al. |
| 6,042,597 | A | 3/2000 | Kveen et al. |
| 6,056,776 | A | 5/2000 | Lau et al. |
| 6,063,101 | A | 5/2000 | Jacobsen et al. |
| 6,071,305 | A | 6/2000 | Brown et al. |
| 6,080,190 | A | 6/2000 | Schwartz |
| 6,086,773 | A * | 7/2000 | Dufresne et al. .................... 216/8 |
| 6,096,070 | A | 8/2000 | Ragheb et al. |
| 6,096,175 | A | 8/2000 | Roth |
| 6,099,561 | A * | 8/2000 | Alt ................ 623/1.44 |
| 6,099,562 | A | 8/2000 | Ding et al. |
| 6,106,473 | A | 8/2000 | Violante et al. |
| 6,107,004 | A | 8/2000 | Donadio, III |
| 6,117,592 | A | 9/2000 | Hoshino et al. |
| 6,120,260 | A | 9/2000 | Jirele |
| 6,120,535 | A * | 9/2000 | McDonald et al. .......... 623/1.39 |
| 6,120,660 | A | 9/2000 | Chu et al. |
| 6,123,861 | A | 9/2000 | Santini, Jr. et al. |
| 6,132,463 | A * | 10/2000 | Lee et al. ......................... 600/36 |
| 6,139,573 | A | 10/2000 | Sogard et al. |
| 6,139,574 | A * | 10/2000 | Vacanti et al. ............... 623/1.44 |
| 6,139,913 | A | 10/2000 | Van Steenkiste et al. |
| 6,140,740 | A | 10/2000 | Porat et al. |
| 6,143,370 | A | 11/2000 | Panagiotou et al. |
| 6,153,252 | A | 11/2000 | Hossainy et al. |
| 6,159,142 | A | 12/2000 | Alt |
| 6,162,238 | A | 12/2000 | Kaplan et al. |
| 6,164,284 | A | 12/2000 | Schulman et al. |
| 6,165,211 | A * | 12/2000 | Thompson .................... 623/1.13 |
| 6,167,307 | A | 12/2000 | Hess |
| 6,168,602 | B1 | 1/2001 | Ryan |
| 6,170,488 | B1 | 1/2001 | Spillman, Jr. et al. |
| 6,174,329 | B1 | 1/2001 | Callol et al. |
| 6,174,330 | B1 | 1/2001 | Stinson |
| 6,180,222 | B1 | 1/2001 | Schulz et al. |
| 6,185,455 | B1 | 2/2001 | Loeb et al. |
| 6,185,457 | B1 | 2/2001 | Kroll et al. |
| 6,190,404 | B1 | 2/2001 | Palmaz et al. |
| 6,192,271 | B1 | 2/2001 | Hayman |
| 6,201,991 | B1 | 3/2001 | Chekanov |
| 6,203,536 | B1 | 3/2001 | Berg et al. |
| 6,206,914 | B1 | 3/2001 | Soykan et al. |
| 6,206,915 | B1 | 3/2001 | Fagan et al. |
| 6,206,916 | B1 | 3/2001 | Furst |
| 6,212,434 | B1 | 4/2001 | Scheiner |
| 6,214,037 | B1 | 4/2001 | Mitchell et al. |
| 6,214,042 | B1 | 4/2001 | Jacobsen et al. |
| 6,217,607 | B1 * | 4/2001 | Alt ................. 623/1.1 |
| 6,231,597 | B1 | 5/2001 | Deem et al. |
| 6,240,616 | B1 * | 6/2001 | Yan .............. 29/527.2 |
| 6,241,762 | B1 | 6/2001 | Shanley |
| 6,245,103 | B1 | 6/2001 | Stinson |
| 6,245,104 | B1 * | 6/2001 | Alt ................. 427/2.25 |
| 6,249,952 | B1 | 6/2001 | Ding |
| 6,251,136 | B1 | 6/2001 | Guruwaiya et al. |
| 6,251,980 | B1 | 6/2001 | Lan et al. |
| 6,253,252 | B1 * | 6/2001 | Schofield ..................... 719/315 |
| 6,253,443 | B1 | 7/2001 | Johnson |
| 6,254,632 | B1 | 7/2001 | Wu et al. |
| 6,258,117 | B1 | 7/2001 | Camrud et al. |
| 6,264,687 | B1 | 7/2001 | Tomonto |
| 6,270,831 | B2 * | 8/2001 | Kumar et al. ................. 427/2.24 |
| 6,273,908 | B1 | 8/2001 | Ndondo-Lay |
| 6,273,913 | B1 | 8/2001 | Wright et al. |
| 6,277,078 | B1 | 8/2001 | Porat et al. |
| 6,280,385 | B1 | 8/2001 | Melzer et al. |
| 6,280,411 | B1 | 8/2001 | Lennox |
| 6,283,386 | B1 | 9/2001 | Van Steenkiste et al. |
| 6,287,331 | B1 | 9/2001 | Heath |
| 6,287,332 | B1 | 9/2001 | Bolz et al. |
| 6,287,335 | B1 | 9/2001 | Drasler et al. |
| 6,287,628 | B1 | 9/2001 | Hossainy et al. |
| 6,290,721 | B1 | 9/2001 | Heath |
| 6,290,722 | B1 | 9/2001 | Wang |
| 6,291,076 | B1 | 9/2001 | Nakatsugawa |
| 6,299,604 | B1 | 10/2001 | Ragheb et al. |
| 6,299,755 | B1 | 10/2001 | Richter |
| 6,306,144 | B1 | 10/2001 | Sydney et al. |
| 6,309,414 | B1 | 10/2001 | Rolando et al. |
| 6,312,463 | B1 | 11/2001 | Rourke et al. |
| 6,315,708 | B1 | 11/2001 | Salmon et al. |
| 6,323,146 | B1 | 11/2001 | Pugh et al. |
| 6,325,825 | B1 | 12/2001 | Kula et al. |
| 6,327,504 | B1 | 12/2001 | Dolgin et al. |
| 6,331,312 | B1 * | 12/2001 | Lee et al. ....................... 424/426 |
| 6,335,029 | B1 * | 1/2002 | Kamath et al. ................ 424/423 |
| 6,337,076 | B1 | 1/2002 | Studin |
| 6,338,739 | B1 | 1/2002 | Datta et al. |
| 6,342,507 | B1 | 1/2002 | Naicker et al. |
| 6,344,055 | B1 | 2/2002 | Shukov |
| 6,348,960 | B1 | 2/2002 | Etori et al. |
| 6,358,276 | B1 | 3/2002 | Edwin |
| 6,364,823 | B1 | 4/2002 | Garibaldi et al. |
| 6,364,856 | B1 | 4/2002 | Ding et al. |
| 6,364,903 | B2 | 4/2002 | Tseng et al. |
| 6,366,808 | B1 | 4/2002 | Schroeppel et al. |
| 6,368,658 | B1 | 4/2002 | Schwarz et al. |
| 6,369,355 | B1 | 4/2002 | Saunders |
| 6,375,826 | B1 | 4/2002 | Wang et al. |
| 6,379,379 | B1 | 4/2002 | Wang |
| 6,379,382 | B1 * | 4/2002 | Yang ............................ 623/1.42 |
| 6,379,383 | B1 | 4/2002 | Palmaz et al. |
| 6,379,392 | B1 | 4/2002 | Walak |
| 6,383,214 | B1 | 5/2002 | Banas et al. |
| 6,387,121 | B1 | 5/2002 | Alt |
| 6,387,124 | B1 | 5/2002 | Buscemi et al. |
| 6,390,967 | B1 | 5/2002 | Forman et al. |
| 6,391,033 | B2 | 5/2002 | Ryan |
| 6,391,052 | B2 | 5/2002 | Buirge et al. |
| 6,395,326 | B1 | 5/2002 | Castro et al. |
| 6,398,806 | B1 | 6/2002 | You |
| 6,409,754 | B1 | 6/2002 | Smith et al. |
| 6,419,692 | B1 * | 7/2002 | Yang et al. .................... 623/1.15 |
| 6,423,092 | B2 | 7/2002 | Datta et al. |
| 6,425,855 | B2 | 7/2002 | Tomonto |
| 6,436,133 | B1 | 8/2002 | Furst et al. |
| 6,440,166 | B1 * | 8/2002 | Kolluri ............................ 623/1.4 |
| 6,440,487 | B1 | 8/2002 | Delfino et al. |
| 6,440,503 | B1 | 8/2002 | Merdan et al. |
| 6,447,540 | B1 | 9/2002 | Fontaine et al. |
| 6,451,871 | B1 | 9/2002 | Winterton et al. |
| 6,458,153 | B1 | 10/2002 | Bailey et al. |
| 6,468,304 | B1 | 10/2002 | Dubois-Rande et al. |
| 6,471,721 | B1 | 10/2002 | Dang |
| 6,471,980 | B2 | 10/2002 | Sirhan et al. |
| 6,475,477 | B1 | 11/2002 | Kohn et al. |
| 6,478,815 | B1 | 11/2002 | Alt |
| 6,479,146 | B1 | 11/2002 | Caruso et al. |
| 6,486,588 | B2 | 11/2002 | Doron |
| 6,488,702 | B1 | 12/2002 | Besselink |
| 6,491,666 | B1 | 12/2002 | Santini, Jr. et al. |
| 6,491,720 | B1 | 12/2002 | Vallana et al. |
| 6,492,096 | B1 | 12/2002 | Liu et al. |
| 6,503,556 | B2 | 1/2003 | Harish et al. |
| 6,503,921 | B2 | 1/2003 | Naicker et al. |
| 6,506,437 | B1 | 1/2003 | Harish et al. |
| 6,506,972 | B1 | 1/2003 | Wang |
| 6,514,283 | B2 | 2/2003 | DiMatteo et al. |

| Patent | Type | Date | Inventor |
|---|---|---|---|
| 6,517,571 | B1 | 2/2003 | Brauker et al. |
| 6,517,888 | B1 | 2/2003 | Weber |
| 6,524,274 | B1 | 2/2003 | Rosenthal et al. |
| 6,524,334 | B1 * | 2/2003 | Thompson ................... 623/1.13 |
| 6,527,801 | B1 | 3/2003 | Dutta |
| 6,527,938 | B2 | 3/2003 | Bales et al. |
| 6,530,949 | B2 | 3/2003 | Konya et al. |
| 6,530,951 | B1 | 3/2003 | Bates et al. |
| 6,537,310 | B1 | 3/2003 | Palmaz et al. |
| 6,537,312 | B2 | 3/2003 | Datta et al. |
| 6,544,582 | B1 | 4/2003 | Yoe |
| 6,544,854 | B1 | 4/2003 | Puchner et al. |
| 6,545,097 | B2 | 4/2003 | Pinchuk et al. |
| 6,549,811 | B2 | 4/2003 | Stewart et al. |
| 6,558,422 | B1 | 5/2003 | Baker et al. |
| 6,558,733 | B1 | 5/2003 | Hossainy et al. |
| 6,565,602 | B2 | 5/2003 | Rolando et al. |
| 6,569,489 | B1 | 5/2003 | Li |
| 6,584,349 | B1 | 6/2003 | Sage et al. |
| 6,585,764 | B2 | 7/2003 | Wright et al. |
| 6,585,765 | B1 | 7/2003 | Hossainy et al. |
| 6,586,705 | B1 | 7/2003 | Schell |
| 6,589,286 | B1 | 7/2003 | Litner |
| 6,599,558 | B1 | 7/2003 | Al-Lamee et al. |
| 6,602,287 | B1 | 8/2003 | Millare et al. |
| 6,607,598 | B2 | 8/2003 | Schwarz et al. |
| 6,613,077 | B2 | 9/2003 | Gilligan et al. |
| 6,613,083 | B2 | 9/2003 | Alt |
| 6,613,432 | B2 | 9/2003 | Zamora et al. |
| 6,616,765 | B1 | 9/2003 | Castro et al. |
| 6,626,933 | B1 | 9/2003 | Lau et al. |
| 6,626,936 | B2 | 9/2003 | Stinson |
| 6,626,939 | B1 | 9/2003 | Burnside et al. |
| 6,627,321 | B1 | 9/2003 | Ellingsen et al. |
| 6,628,989 | B1 | 9/2003 | Penner |
| 6,629,992 | B2 | 10/2003 | Bigus et al. |
| 6,635,082 | B1 | 10/2003 | Hossainy et al. |
| 6,638,302 | B1 | 10/2003 | Curcio et al. |
| 6,641,607 | B1 * | 11/2003 | Hossainy et al. ............ 623/1.15 |
| 6,652,575 | B2 | 11/2003 | Wang |
| 6,652,578 | B2 | 11/2003 | Bailey et al. |
| 6,652,581 | B1 | 11/2003 | Ding |
| 6,652,582 | B1 * | 11/2003 | Stinson ........................ 623/1.39 |
| 6,660,034 | B1 | 12/2003 | Mandrusov et al. |
| 6,663,662 | B2 | 12/2003 | Pacetti et al. |
| 6,663,664 | B1 | 12/2003 | Pacetti |
| 6,669,980 | B2 | 12/2003 | Hansen |
| 6,673,105 | B1 | 1/2004 | Chen |
| 6,673,385 | B1 | 1/2004 | Ding et al. |
| 6,673,999 | B1 | 1/2004 | Wang et al. |
| 6,676,987 | B2 | 1/2004 | Zhong |
| 6,676,989 | B2 | 1/2004 | Kirkpatrick et al. |
| 6,689,160 | B1 * | 2/2004 | Okuda et al. ................. 623/1.39 |
| 6,689,803 | B2 | 2/2004 | Hunter |
| 6,695,865 | B2 | 2/2004 | Boyle et al. |
| 6,696,666 | B2 | 2/2004 | Merdan et al. |
| 6,696,667 | B1 | 2/2004 | Flanagan |
| 6,699,281 | B2 | 3/2004 | Vallana et al. |
| 6,699,282 | B1 | 3/2004 | Sceusa |
| 6,709,379 | B1 | 3/2004 | Brandau et al. |
| 6,709,397 | B2 | 3/2004 | Taylor |
| 6,709,451 | B1 | 3/2004 | Noble et al. |
| 6,710,053 | B2 | 3/2004 | Naicker et al. |
| 6,712,844 | B2 | 3/2004 | Pacetti |
| 6,712,845 | B2 | 3/2004 | Hossainy |
| 6,713,671 | B1 | 3/2004 | Wang et al. |
| 6,716,444 | B1 * | 4/2004 | Castro et al. .................. 424/422 |
| 6,719,987 | B2 * | 4/2004 | Burrell et al. ................. 424/405 |
| 6,720,402 | B2 | 4/2004 | Langer et al. |
| 6,723,120 | B2 | 4/2004 | Yan |
| 6,723,350 | B2 * | 4/2004 | Burrell et al. ................. 424/618 |
| 6,725,901 | B1 | 4/2004 | Kramer et al. |
| 6,726,712 | B1 | 4/2004 | Raeder-Devens |
| 6,730,117 | B1 | 5/2004 | Tseng et al. |
| 6,730,120 | B2 | 5/2004 | Berg et al. |
| 6,730,699 | B2 | 5/2004 | Li et al. |
| 6,733,513 | B2 | 5/2004 | Boyle et al. |
| 6,740,077 | B1 | 5/2004 | Brandau et al. |
| 6,743,388 | B2 | 6/2004 | Sridharan et al. |
| 6,752,826 | B2 | 6/2004 | Holloway et al. |
| 6,752,829 | B2 | 6/2004 | Kocur et al. |
| 6,753,071 | B1 | 6/2004 | Pacetti |
| 6,758,859 | B1 | 7/2004 | Dang et al. |
| 6,764,505 | B1 | 7/2004 | Hossainy et al. |
| 6,764,579 | B2 | 7/2004 | Veerasamy et al. |
| 6,764,709 | B2 | 7/2004 | Flanagan |
| 6,765,144 | B1 | 7/2004 | Wang et al. |
| 6,767,360 | B1 | 7/2004 | Alt et al. |
| 6,770,086 | B1 | 8/2004 | Girton |
| 6,770,729 | B2 | 8/2004 | Van Antwerp |
| 6,774,278 | B1 | 8/2004 | Ragheb et al. |
| 6,776,022 | B2 | 8/2004 | Kula et al. |
| 6,776,094 | B1 | 8/2004 | Whitesides et al. |
| 6,776,793 | B2 | 8/2004 | Brown et al. |
| 6,780,424 | B2 | 8/2004 | Claude |
| 6,783,543 | B2 | 8/2004 | Jang |
| 6,790,228 | B2 | 9/2004 | Hossainy et al. |
| 6,793,877 | B1 | 9/2004 | Pettersen et al. |
| 6,796,435 | B2 | 9/2004 | Izumi |
| 6,803,070 | B2 | 10/2004 | Weber |
| 6,805,709 | B1 | 10/2004 | Schaldach et al. |
| 6,805,898 | B1 * | 10/2004 | Wu et al. ...................... 427/2.25 |
| 6,807,440 | B2 | 10/2004 | Weber |
| RE38,653 | E | 11/2004 | Igaki et al. |
| 6,815,609 | B1 | 11/2004 | Wang et al. |
| 6,820,676 | B2 | 11/2004 | Palmaz et al. |
| 6,827,737 | B2 | 12/2004 | Hill et al. |
| 6,827,966 | B2 | 12/2004 | Qiu et al. |
| 6,833,004 | B2 * | 12/2004 | Ishii et al. .................... 623/1.15 |
| 6,846,323 | B2 | 1/2005 | Yip et al. |
| 6,846,841 | B2 | 1/2005 | Hunter et al. |
| 6,847,837 | B1 | 1/2005 | Melzer et al. |
| 6,849,085 | B2 | 2/2005 | Marton |
| 6,849,089 | B2 * | 2/2005 | Stoll ............................ 623/1.42 |
| 6,852,122 | B2 | 2/2005 | Rush |
| 6,854,172 | B2 | 2/2005 | Kaese et al. |
| 6,861,088 | B2 | 3/2005 | Weber et al. |
| 6,865,810 | B2 | 3/2005 | Stinson |
| 6,866,805 | B2 | 3/2005 | Hong et al. |
| 6,869,443 | B2 | 3/2005 | Buscemi et al. |
| 6,869,701 | B1 * | 3/2005 | Aita et al. ...................... 428/698 |
| 6,875,227 | B2 | 4/2005 | Yoon |
| 6,878,249 | B2 | 4/2005 | Kouyama et al. |
| 6,884,429 | B2 | 4/2005 | Koziak et al. |
| 6,887,270 | B2 | 5/2005 | Miller et al. |
| 6,887,857 | B2 | 5/2005 | Naimark et al. |
| 6,896,697 | B1 | 5/2005 | Yip et al. |
| 6,899,731 | B2 | 5/2005 | Li et al. |
| 6,899,914 | B2 | 5/2005 | Schaldach et al. |
| 6,904,658 | B2 | 6/2005 | Hines |
| 6,908,506 | B2 | 6/2005 | Zimmermann |
| 6,908,622 | B2 | 6/2005 | Barry et al. |
| 6,908,624 | B2 * | 6/2005 | Hossainy et al. ............. 424/424 |
| 6,913,617 | B1 | 7/2005 | Reiss |
| 6,913,765 | B2 | 7/2005 | Li et al. |
| 6,918,869 | B2 | 7/2005 | Shaw et al. |
| 6,918,927 | B2 * | 7/2005 | Bates et al. .................. 623/1.15 |
| 6,921,390 | B2 * | 7/2005 | Bucay-Couto et al. ........ 604/265 |
| 6,923,996 | B2 | 8/2005 | Epstein et al. |
| 6,926,735 | B2 * | 8/2005 | Henderson ................... 623/1.42 |
| 6,932,930 | B2 | 8/2005 | DeSimone et al. |
| 6,936,066 | B2 | 8/2005 | Palmaz et al. |
| 6,939,320 | B2 | 9/2005 | Lennox |
| 6,945,993 | B2 | 9/2005 | Kveen et al. |
| 6,951,053 | B2 | 10/2005 | Padilla et al. |
| 6,953,560 | B1 | 10/2005 | Castro et al. |
| 6,953,594 | B2 | 10/2005 | Lee et al. |
| 6,954,977 | B2 | 10/2005 | Maguire et al. |
| 6,955,661 | B1 | 10/2005 | Herweck et al. |
| 6,955,685 | B2 | 10/2005 | Escamilla et al. |
| 6,962,822 | B2 | 11/2005 | Hart et al. |
| 6,964,817 | B2 | 11/2005 | Date et al. |
| 6,971,813 | B2 | 12/2005 | Shekalim et al. |
| 6,972,130 | B1 * | 12/2005 | Lee et al. ...................... 424/426 |
| 6,973,718 | B2 | 12/2005 | Sheppard, Jr. et al. |
| 6,979,346 | B1 | 12/2005 | Hossainy et al. |
| 6,979,347 | B1 | 12/2005 | Wu et al. |
| 6,979,348 | B2 | 12/2005 | Sundar |

| | | |
|---|---|---|
| 6,981,986 B1 | 1/2006 | Brown et al. |
| 6,984,404 B1 | 1/2006 | Talton et al. |
| 6,986,899 B2 | 1/2006 | Hossainy et al. |
| 6,989,156 B2* | 1/2006 | Gillis .................... 424/618 |
| 6,991,709 B2 | 1/2006 | Gopalraja et al. |
| 7,001,421 B2 | 2/2006 | Cheng et al. |
| 7,004,968 B2 | 2/2006 | Lootz et al. |
| 7,011,670 B2 | 3/2006 | Radisch, Jr. |
| 7,011,678 B2 | 3/2006 | Tenerz et al. |
| 7,011,680 B2 | 3/2006 | Alt |
| 7,018,408 B2 | 3/2006 | Bailey et al. |
| 7,022,334 B1* | 4/2006 | Ding .................... 424/423 |
| 7,041,130 B2 | 5/2006 | Santini, Jr. |
| 7,048,767 B2* | 5/2006 | Namavar ................ 623/23.6 |
| 7,048,939 B2 | 5/2006 | Elkins et al. |
| 7,052,488 B2 | 5/2006 | Uhland |
| 7,056,338 B2 | 6/2006 | Shanley et al. |
| 7,056,339 B2 | 6/2006 | Elkins et al. |
| 7,060,051 B2 | 6/2006 | Palasis |
| 7,060,240 B2* | 6/2006 | Costa et al. ............... 423/338 |
| 7,063,748 B2 | 6/2006 | Talton |
| 7,067,606 B2 | 6/2006 | Mather et al. |
| 7,070,576 B2 | 7/2006 | O'Brien et al. |
| 7,077,859 B2 | 7/2006 | Sirhan et al. |
| 7,078,108 B2* | 7/2006 | Zhang et al. .............. 428/579 |
| 7,099,091 B2* | 8/2006 | Taniguchi et al. ........... 359/722 |
| 7,101,391 B2 | 9/2006 | Scheuermann et al. |
| 7,101,394 B2* | 9/2006 | Hamm et al. ............. 623/1.42 |
| 7,105,018 B1 | 9/2006 | Yip et al. |
| 7,105,199 B2 | 9/2006 | Blinn et al. |
| 7,108,716 B2 | 9/2006 | Burnside et al. |
| 7,157,096 B2* | 1/2007 | Zhang et al. .............. 424/422 |
| 7,160,592 B2* | 1/2007 | Rypacek et al. ............ 428/36.9 |
| 7,163,715 B1 | 1/2007 | Kramer |
| 7,169,173 B2 | 1/2007 | Hossainy et al. |
| 7,169,178 B1 | 1/2007 | Santos et al. |
| 7,195,640 B2 | 3/2007 | Falotico et al. |
| 7,195,641 B2 | 3/2007 | Palmaz et al. |
| 7,198,675 B2 | 4/2007 | Fox et al. |
| 7,208,011 B2 | 4/2007 | Shanley et al. |
| 7,208,172 B2 | 4/2007 | Birdsall et al. |
| 7,220,816 B2 | 5/2007 | Pacetti et al. |
| 7,226,475 B2 | 6/2007 | Lenz et al. |
| 7,229,471 B2 | 6/2007 | Gale et al. |
| 7,235,096 B1 | 6/2007 | Van Tassel et al. |
| 7,235,098 B2 | 6/2007 | Palmaz |
| 7,238,199 B2 | 7/2007 | Feldman et al. |
| 7,241,295 B2 | 7/2007 | Maguire |
| 7,244,272 B2* | 7/2007 | Dubson et al. ............ 623/1.44 |
| 7,261,732 B2 | 8/2007 | Justino |
| 7,261,735 B2* | 8/2007 | Llanos et al. ............. 623/1.46 |
| 7,267,960 B2 | 9/2007 | Galibert et al. |
| 7,279,174 B2 | 10/2007 | Pacetti |
| 7,279,175 B2* | 10/2007 | Chen et al. .............. 623/1.42 |
| 7,294,409 B2 | 11/2007 | Lye et al. |
| 7,311,727 B2 | 12/2007 | Mazumder et al. |
| 7,323,189 B2* | 1/2008 | Pathak .................... 424/423 |
| RE40,122 E | 2/2008 | Thompson |
| 7,331,993 B2 | 2/2008 | White |
| 7,335,375 B2 | 2/2008 | Li et al. |
| 7,344,560 B2* | 3/2008 | Gregorich et al. .......... 623/1.15 |
| 7,344,563 B2 | 3/2008 | Vallana et al. |
| 7,393,589 B2 | 7/2008 | Aharonov et al. |
| 7,402,173 B2 | 7/2008 | Scheuermann et al. |
| 7,416,558 B2 | 8/2008 | Yip et al. |
| 7,432,327 B2* | 10/2008 | Glasgow et al. ............ 525/106 |
| 7,462,366 B2 | 12/2008 | Lanphere |
| 7,498,385 B2* | 3/2009 | Swetlin et al. ............. 525/172 |
| 7,507,433 B2* | 3/2009 | Weber .................... 427/2.1 |
| 7,537,610 B2* | 5/2009 | Reiss .................... 623/1.39 |
| 7,547,445 B2 | 6/2009 | Chudzik et al. |
| 7,563,277 B2 | 7/2009 | Case et al. |
| 7,637,941 B1 | 12/2009 | Manicka et al. |
| 7,651,527 B2 | 1/2010 | Krivoruchko et al. |
| 7,691,401 B2* | 4/2010 | Castro et al. .............. 424/423 |
| 7,713,297 B2* | 5/2010 | Alt ..................... 623/1.39 |
| 7,713,573 B2* | 5/2010 | Owens et al. .............. 427/2.1 |
| 7,722,805 B2* | 5/2010 | Hao et al. ................ 420/417 |
| 7,749,264 B2* | 7/2010 | Gregorich et al. .......... 623/1.15 |
| 7,758,635 B2* | 7/2010 | Parsonage ................ 623/1.41 |
| 7,771,773 B2* | 8/2010 | Namavar ................. 427/2.1 |
| 7,776,926 B1* | 8/2010 | Claude et al. ............. 514/772.1 |
| 2001/0001834 A1 | 5/2001 | Palmaz et al. |
| 2001/0002000 A1 | 5/2001 | Kumar et al. |
| 2001/0002435 A1 | 5/2001 | Berg et al. |
| 2001/0013166 A1 | 8/2001 | Yan |
| 2001/0021871 A1 | 9/2001 | Stinson |
| 2001/0021873 A1 | 9/2001 | Stinson |
| 2001/0027299 A1 | 10/2001 | Yang et al. |
| 2001/0029398 A1 | 10/2001 | Jadhav |
| 2001/0029660 A1 | 10/2001 | Johnson |
| 2001/0032011 A1 | 10/2001 | Stanford |
| 2001/0032013 A1 | 10/2001 | Marton |
| 2001/0032014 A1 | 10/2001 | Yang et al. |
| 2001/0044650 A1 | 11/2001 | Simso et al. |
| 2002/0000175 A1 | 1/2002 | Hintermaier et al. |
| 2002/0000406 A1 | 1/2002 | Izumi |
| 2002/0004060 A1* | 1/2002 | Heublein et al. ............ 424/422 |
| 2002/0007102 A1 | 1/2002 | Salmon et al. |
| 2002/0007209 A1 | 1/2002 | Scheerder et al. |
| 2002/0010505 A1 | 1/2002 | Richter |
| 2002/0016623 A1 | 2/2002 | Kula et al. |
| 2002/0016624 A1 | 2/2002 | Patterson et al. |
| 2002/0028827 A1 | 3/2002 | Naicker et al. |
| 2002/0032477 A1 | 3/2002 | Helmus et al. |
| 2002/0035394 A1 | 3/2002 | Fierens et al. |
| 2002/0038146 A1 | 3/2002 | Harry |
| 2002/0042039 A1 | 4/2002 | Kim et al. |
| 2002/0049495 A1 | 4/2002 | Kutryk et al. |
| 2002/0051730 A1 | 5/2002 | Bodnar et al. |
| 2002/0051846 A1 | 5/2002 | Kirkpatrick et al. |
| 2002/0065553 A1 | 5/2002 | Weber |
| 2002/0082679 A1 | 6/2002 | Sirhan et al. |
| 2002/0087123 A1 | 7/2002 | Hossainy et al. |
| 2002/0090313 A1 | 7/2002 | Wang et al. |
| 2002/0091375 A1 | 7/2002 | Sahatjian et al. |
| 2002/0098278 A1 | 7/2002 | Bates et al. |
| 2002/0099434 A1 | 7/2002 | Buscemi et al. |
| 2002/0099438 A1 | 7/2002 | Furst |
| 2002/0103527 A1 | 8/2002 | Kocur et al. |
| 2002/0103528 A1 | 8/2002 | Schaldach et al. |
| 2002/0111694 A1 | 8/2002 | Ellingsen et al. |
| 2002/0121497 A1 | 9/2002 | Tomonto |
| 2002/0123801 A1 | 9/2002 | Pacetti et al. |
| 2002/0133222 A1 | 9/2002 | Das |
| 2002/0133224 A1 | 9/2002 | Bajgar et al. |
| 2002/0138100 A1 | 9/2002 | Stoll et al. |
| 2002/0138131 A1 | 9/2002 | Solovay et al. |
| 2002/0138136 A1 | 9/2002 | Chandresekaran et al. |
| 2002/0138154 A1* | 9/2002 | Li et al. .................. 623/66.1 |
| 2002/0144757 A1 | 10/2002 | Craig et al. |
| 2002/0151964 A1 | 10/2002 | Smith et al. |
| 2002/0155212 A1 | 10/2002 | Hossainy |
| 2002/0165265 A1 | 11/2002 | Hunter et al. |
| 2002/0165578 A1 | 11/2002 | Sawitowski et al. |
| 2002/0165600 A1 | 11/2002 | Banas et al. |
| 2002/0165607 A1 | 11/2002 | Alt |
| 2002/0169493 A1 | 11/2002 | Widenhouse et al. |
| 2002/0178570 A1 | 12/2002 | Sogard et al. |
| 2002/0182241 A1 | 12/2002 | Borenstein et al. |
| 2002/0183581 A1 | 12/2002 | Yoe et al. |
| 2002/0183682 A1 | 12/2002 | Darvish et al. |
| 2002/0187260 A1 | 12/2002 | Sheppard, Jr. et al. |
| 2002/0193336 A1 | 12/2002 | Elkins et al. |
| 2002/0193869 A1 | 12/2002 | Dang |
| 2002/0197178 A1 | 12/2002 | Yan |
| 2002/0198601 A1 | 12/2002 | Bales et al. |
| 2003/0003127 A1* | 1/2003 | Brown et al. .............. 424/423 |
| 2003/0003220 A1 | 1/2003 | Zhong et al. |
| 2003/0004563 A1 | 1/2003 | Jackson et al. |
| 2003/0004564 A1* | 1/2003 | Elkins et al. ............. 623/1.15 |
| 2003/0009214 A1 | 1/2003 | Shanley |
| 2003/0018380 A1 | 1/2003 | Craig et al. |
| 2003/0018381 A1 | 1/2003 | Whitcher et al. |
| 2003/0023300 A1 | 1/2003 | Bailey et al. |
| 2003/0028242 A1 | 2/2003 | Vallana et al. |
| 2003/0028243 A1 | 2/2003 | Bates et al. |
| 2003/0032892 A1 | 2/2003 | Erlach et al. |

| Pub. No. | Date | Inventor |
|---|---|---|
| 2003/0033007 A1 | 2/2003 | Sirhan et al. |
| 2003/0044446 A1 | 3/2003 | Moro et al. |
| 2003/0044596 A1 | 3/2003 | Lazarov et al. |
| 2003/0050687 A1 | 3/2003 | Schwade et al. |
| 2003/0050692 A1 | 3/2003 | Sirhan et al. |
| 2003/0059640 A1 | 3/2003 | Marton et al. |
| 2003/0060871 A1 | 3/2003 | Hill et al. |
| 2003/0060873 A1 | 3/2003 | Gertner et al. |
| 2003/0064095 A1 | 4/2003 | Martin et al. |
| 2003/0068355 A1 | 4/2003 | Shanley et al. |
| 2003/0069631 A1 | 4/2003 | Stoll |
| 2003/0074053 A1 | 4/2003 | Palmaz et al. |
| 2003/0077200 A1 | 4/2003 | Craig et al. |
| 2003/0077310 A1 | 4/2003 | Pathak et al. |
| 2003/0083614 A1 | 5/2003 | Eisert |
| 2003/0083646 A1 | 5/2003 | Sirhan et al. |
| 2003/0083731 A1 | 5/2003 | Kramer et al. |
| 2003/0087024 A1 | 5/2003 | Flanagan |
| 2003/0088307 A1 | 5/2003 | Shulze et al. |
| 2003/0088312 A1 | 5/2003 | Kopia et al. |
| 2003/0099684 A1 | 5/2003 | Domb |
| 2003/0100815 A1 | 5/2003 | Da Silva et al. |
| 2003/0100830 A1 | 5/2003 | Zhong et al. |
| 2003/0104030 A1 | 6/2003 | Igaki et al. |
| 2003/0105511 A1 | 6/2003 | Welsh et al. |
| 2003/0108659 A1 | 6/2003 | Bales et al. |
| 2003/0114917 A1 | 6/2003 | Holloway et al. |
| 2003/0114921 A1 | 6/2003 | Yoon |
| 2003/0118692 A1* | 6/2003 | Wang et al. ............ 426/6 |
| 2003/0120339 A1 | 6/2003 | Banik et al. |
| 2003/0124055 A1 | 7/2003 | Li et al. |
| 2003/0125803 A1 | 7/2003 | Vallana |
| 2003/0130718 A1 | 7/2003 | Palmas et al. |
| 2003/0139799 A1 | 7/2003 | Ley et al. |
| 2003/0143330 A1 | 7/2003 | Loomis et al. |
| 2003/0144728 A1 | 7/2003 | Scheuermann et al. |
| 2003/0150380 A1 | 8/2003 | Yoe |
| 2003/0153901 A1 | 8/2003 | Herweck et al. |
| 2003/0158598 A1 | 8/2003 | Ashton et al. |
| 2003/0170605 A1 | 9/2003 | Long et al. |
| 2003/0181975 A1 | 9/2003 | Ishii et al. |
| 2003/0185895 A1 | 10/2003 | Lanphere |
| 2003/0190406 A1* | 10/2003 | Hossainy et al. ............ 427/2.25 |
| 2003/0195613 A1 | 10/2003 | Curcio et al. |
| 2003/0199993 A1 | 10/2003 | Gellman et al. |
| 2003/0204239 A1 | 10/2003 | Carlyle et al. |
| 2003/0211135 A1 | 11/2003 | Greenhalgh et al. |
| 2003/0216803 A1 | 11/2003 | Ledergerber |
| 2003/0219562 A1 | 11/2003 | Rypacek et al. |
| 2003/0221307 A1 | 12/2003 | Kaese et al. |
| 2003/0228523 A1 | 12/2003 | DeLongchamp et al. |
| 2003/0236513 A1 | 12/2003 | Schwarz et al. |
| 2004/0000046 A1 | 1/2004 | Stinson |
| 2004/0000540 A1 | 1/2004 | Soboyejo et al. |
| 2004/0004063 A1 | 1/2004 | Merdan |
| 2004/0006382 A1 | 1/2004 | Sohier |
| 2004/0018296 A1 | 1/2004 | Castro et al. |
| 2004/0019376 A1 | 1/2004 | Alt |
| 2004/0022939 A1 | 2/2004 | Kim et al. |
| 2004/0024448 A1 | 2/2004 | Chang et al. |
| 2004/0029303 A1 | 2/2004 | Hart et al. |
| 2004/0030218 A1 | 2/2004 | Kocur et al. |
| 2004/0030377 A1 | 2/2004 | Dubson et al. |
| 2004/0030379 A1 | 2/2004 | Hamm et al. |
| 2004/0034409 A1 | 2/2004 | Heublein et al. |
| 2004/0039438 A1* | 2/2004 | Alt .................. 623/1.15 |
| 2004/0039441 A1 | 2/2004 | Rowland et al. |
| 2004/0044397 A1 | 3/2004 | Stinson |
| 2004/0047980 A1 | 3/2004 | Pacetti et al. |
| 2004/0059407 A1 | 3/2004 | Escamilla et al. |
| 2004/0059409 A1 | 3/2004 | Stenzel |
| 2004/0067301 A1 | 4/2004 | Ding |
| 2004/0071861 A1 | 4/2004 | Mandrusov et al. |
| 2004/0073155 A1 | 4/2004 | Laufer et al. |
| 2004/0073284 A1 | 4/2004 | Bates et al. |
| 2004/0073293 A1 | 4/2004 | Thompson |
| 2004/0073297 A1 | 4/2004 | Rohde et al. |
| 2004/0073298 A1 | 4/2004 | Hossainy |
| 2004/0078071 A1 | 4/2004 | Escamilla et al. |
| 2004/0082682 A1 | 4/2004 | Loomis et al. |
| 2004/0088038 A1 | 5/2004 | Dehnad et al. |
| 2004/0088041 A1 | 5/2004 | Stanford |
| 2004/0093071 A1 | 5/2004 | Jang |
| 2004/0093075 A1 | 5/2004 | Kuehne |
| 2004/0093076 A1 | 5/2004 | White et al. |
| 2004/0098089 A1 | 5/2004 | Weber |
| 2004/0098108 A1 | 5/2004 | Harder et al. |
| 2004/0098119 A1 | 5/2004 | Wang |
| 2004/0106975 A1* | 6/2004 | Solovay et al. ............ 623/1.11 |
| 2004/0106984 A1 | 6/2004 | Stinson |
| 2004/0106985 A1 | 6/2004 | Jang |
| 2004/0111150 A1 | 6/2004 | Berg et al. |
| 2004/0116999 A1 | 6/2004 | Ledergerber |
| 2004/0117005 A1 | 6/2004 | Gadde et al. |
| 2004/0117008 A1* | 6/2004 | Wnendt et al. ............ 623/1.46 |
| 2004/0122504 A1 | 6/2004 | Hogendijk |
| 2004/0126566 A1 | 7/2004 | Axen et al. |
| 2004/0133270 A1 | 7/2004 | Grandt |
| 2004/0134886 A1 | 7/2004 | Wagner et al. |
| 2004/0137039 A1 | 7/2004 | Sukhishvili et al. |
| 2004/0138738 A1 | 7/2004 | Stinson |
| 2004/0142014 A1 | 7/2004 | Litvack et al. |
| 2004/0143317 A1 | 7/2004 | Stinson et al. |
| 2004/0143321 A1 | 7/2004 | Litvack et al. |
| 2004/0148010 A1 | 7/2004 | Rush |
| 2004/0148015 A1 | 7/2004 | Lye et al. |
| 2004/0153138 A1 | 8/2004 | Murphy |
| 2004/0157073 A1* | 8/2004 | Burrell et al. ............ 428/500 |
| 2004/0158308 A1 | 8/2004 | Hogendijk et al. |
| 2004/0158310 A1 | 8/2004 | Weber et al. |
| 2004/0167572 A1 | 8/2004 | Roth et al. |
| 2004/0167609 A1 | 8/2004 | Majercak |
| 2004/0167612 A1 | 8/2004 | Grignani et al. |
| 2004/0172124 A1 | 9/2004 | Vallana et al. |
| 2004/0181252 A1 | 9/2004 | Boyle et al. |
| 2004/0181275 A1 | 9/2004 | Noble et al. |
| 2004/0181276 A1 | 9/2004 | Brown et al. |
| 2004/0181278 A1 | 9/2004 | Tseng et al. |
| 2004/0182511 A1* | 9/2004 | Rakos et al. ............ 623/1.44 |
| 2004/0186553 A1 | 9/2004 | Yan |
| 2004/0191293 A1 | 9/2004 | Claude |
| 2004/0191404 A1 | 9/2004 | Hossainy et al. |
| 2004/0202692 A1 | 10/2004 | Shanley et al. |
| 2004/0204750 A1 | 10/2004 | Dinh |
| 2004/0211362 A1 | 10/2004 | Castro et al. |
| 2004/0219214 A1 | 11/2004 | Gravett et al. |
| 2004/0220510 A1 | 11/2004 | Koullick et al. |
| 2004/0220659 A1 | 11/2004 | Girton |
| 2004/0220660 A1 | 11/2004 | Shanley et al. |
| 2004/0220662 A1 | 11/2004 | Dang et al. |
| 2004/0224001 A1 | 11/2004 | Pacetti et al. |
| 2004/0225346 A1 | 11/2004 | Mazumder et al. |
| 2004/0228905 A1 | 11/2004 | Greenspan et al. |
| 2004/0230176 A1 | 11/2004 | Shanahan et al. |
| 2004/0230225 A1 | 11/2004 | Penner et al. |
| 2004/0230290 A1 | 11/2004 | Weber et al. |
| 2004/0230293 A1 | 11/2004 | Yip et al. |
| 2004/0234737 A1 | 11/2004 | Pacetti |
| 2004/0236415 A1 | 11/2004 | Thomas |
| 2004/0236416 A1 | 11/2004 | Falotico |
| 2004/0237282 A1 | 12/2004 | Hines |
| 2004/0242106 A1 | 12/2004 | Rabasco et al. |
| 2004/0243217 A1 | 12/2004 | Andersen |
| 2004/0243237 A1 | 12/2004 | Unwin et al. |
| 2004/0243241 A1 | 12/2004 | Istephanous et al. |
| 2004/0247671 A1 | 12/2004 | Prescott et al. |
| 2004/0249440 A1 | 12/2004 | Bucker et al. |
| 2004/0249443 A1 | 12/2004 | Shanley et al. |
| 2004/0249444 A1 | 12/2004 | Reiss |
| 2004/0249445 A1 | 12/2004 | Rosenthal et al. |
| 2004/0249449 A1 | 12/2004 | Shanley et al. |
| 2004/0254419 A1 | 12/2004 | Wang et al. |
| 2004/0254635 A1 | 12/2004 | Shanley et al. |
| 2005/0004661 A1 | 1/2005 | Lewis et al. |
| 2005/0010275 A1 | 1/2005 | Sahatjian |
| 2005/0010279 A1 | 1/2005 | Tenerz et al. |
| 2005/0015142 A1 | 1/2005 | Austin et al. |
| 2005/0019265 A1 | 1/2005 | Hammer et al. |

| | | |
|---|---|---|
| 2005/0019371 A1 | 1/2005 | Anderson et al. |
| 2005/0021127 A1 | 1/2005 | Kawula |
| 2005/0021128 A1 | 1/2005 | Nakahama et al. |
| 2005/0022627 A1 | 2/2005 | Chen |
| 2005/0025804 A1 | 2/2005 | Heller |
| 2005/0027350 A1 | 2/2005 | Momma et al. |
| 2005/0033407 A1* | 2/2005 | Weber et al. ............... 623/1.15 |
| 2005/0033411 A1 | 2/2005 | Wu et al. |
| 2005/0033412 A1 | 2/2005 | Wu et al. |
| 2005/0033417 A1 | 2/2005 | Borges et al. |
| 2005/0037047 A1 | 2/2005 | Song |
| 2005/0037050 A1 | 2/2005 | Weber |
| 2005/0038134 A1 | 2/2005 | Loomis et al. |
| 2005/0038501 A1 | 2/2005 | Moore, Jr. et al. |
| 2005/0042288 A1 | 2/2005 | Koblish et al. |
| 2005/0042440 A1 | 2/2005 | Bach et al. |
| 2005/0055044 A1 | 3/2005 | Kangas |
| 2005/0055080 A1 | 3/2005 | Istephanous et al. |
| 2005/0055085 A1 | 3/2005 | Rivron et al. |
| 2005/0060020 A1 | 3/2005 | Jenson |
| 2005/0060021 A1* | 3/2005 | O'Brien et al. ............... 623/1.15 |
| 2005/0064088 A1 | 3/2005 | Fredrickson |
| 2005/0069630 A1 | 3/2005 | Fox et al. |
| 2005/0070989 A1 | 3/2005 | Lye et al. |
| 2005/0070990 A1 | 3/2005 | Stinson |
| 2005/0070996 A1 | 3/2005 | Dinh et al. |
| 2005/0071016 A1 | 3/2005 | Hausdorf et al. |
| 2005/0072544 A1 | 4/2005 | Palmaz et al. |
| 2005/0074479 A1 | 4/2005 | Weber et al. |
| 2005/0074545 A1 | 4/2005 | Thomas |
| 2005/0075714 A1 | 4/2005 | Cheng et al. |
| 2005/0077305 A1 | 4/2005 | Guevara |
| 2005/0079132 A1 | 4/2005 | Wang et al. |
| 2005/0079199 A1 | 4/2005 | Heruth et al. |
| 2005/0079356 A1 | 4/2005 | Rathenow et al. |
| 2005/0092615 A1 | 5/2005 | Birdsall et al. |
| 2005/0096731 A1 | 5/2005 | Looi et al. |
| 2005/0100577 A1 | 5/2005 | Parker et al. |
| 2005/0100609 A1 | 5/2005 | Claude |
| 2005/0102025 A1 | 5/2005 | Laroche et al. |
| 2005/0106212 A1 | 5/2005 | Gertner et al. |
| 2005/0107869 A1 | 5/2005 | Sirhan et al. |
| 2005/0107870 A1* | 5/2005 | Wang et al. ............... 623/1.44 |
| 2005/0113936 A1 | 5/2005 | Brustad et al. |
| 2005/0119723 A1 | 6/2005 | Peacock |
| 2005/0129727 A1 | 6/2005 | Weber et al. |
| 2005/0129731 A1 | 6/2005 | Horres et al. |
| 2005/0131509 A1 | 6/2005 | Atanassoska et al. |
| 2005/0131521 A1 | 6/2005 | Marton |
| 2005/0131522 A1 | 6/2005 | Stinson et al. |
| 2005/0131527 A1 | 6/2005 | Pathak |
| 2005/0131528 A1 | 6/2005 | Buscemi et al. |
| 2005/0136090 A1 | 6/2005 | Falotico et al. |
| 2005/0137677 A1 | 6/2005 | Rush |
| 2005/0137679 A1 | 6/2005 | Changelian et al. |
| 2005/0137684 A1 | 6/2005 | Changelian et al. |
| 2005/0149169 A1 | 7/2005 | Wang et al. |
| 2005/0149170 A1 | 7/2005 | Tassel et al. |
| 2005/0149175 A1 | 7/2005 | Hunter et al. |
| 2005/0149177 A1 | 7/2005 | Weber et al. |
| 2005/0159804 A1 | 7/2005 | Lad et al. |
| 2005/0159805 A1* | 7/2005 | Weber et al. ............... 623/1.15 |
| 2005/0159809 A1 | 7/2005 | Hezi-Yamit et al. |
| 2005/0160600 A1 | 7/2005 | Bien et al. |
| 2005/0163821 A1 | 7/2005 | Sung et al. |
| 2005/0163954 A1 | 7/2005 | Shaw |
| 2005/0165301 A1 | 7/2005 | Smith et al. |
| 2005/0165468 A1 | 7/2005 | Marton |
| 2005/0165470 A1 | 7/2005 | Weber |
| 2005/0169969 A1 | 8/2005 | Li et al. |
| 2005/0171595 A1 | 8/2005 | Feldman et al. |
| 2005/0177226 A1 | 8/2005 | Banik et al. |
| 2005/0180919 A1 | 8/2005 | Tedeschi |
| 2005/0182361 A1 | 8/2005 | Lennox |
| 2005/0182478 A1 | 8/2005 | Holman et al. |
| 2005/0186250 A1 | 8/2005 | Gertner et al. |
| 2005/0187605 A1 | 8/2005 | Greenhalgh et al. |
| 2005/0187611 A1 | 8/2005 | Ding et al. |
| 2005/0187615 A1 | 8/2005 | Williams et al. |
| 2005/0192657 A1 | 9/2005 | Colen et al. |
| 2005/0192662 A1 | 9/2005 | Ward |
| 2005/0192664 A1 | 9/2005 | Eisert |
| 2005/0196424 A1 | 9/2005 | Chappa |
| 2005/0208098 A1 | 9/2005 | Castro et al. |
| 2005/0208100 A1 | 9/2005 | Weber et al. |
| 2005/0209680 A1 | 9/2005 | Gale et al. |
| 2005/0209681 A1 | 9/2005 | Curcio et al. |
| 2005/0211680 A1 | 9/2005 | Li et al. |
| 2005/0214951 A1 | 9/2005 | Nahm et al. |
| 2005/0216074 A1 | 9/2005 | Sahatjian |
| 2005/0216075 A1 | 9/2005 | Wang et al. |
| 2005/0220853 A1 | 10/2005 | Dao et al. |
| 2005/0221072 A1 | 10/2005 | Dubrow et al. |
| 2005/0222671 A1 | 10/2005 | Schaeffer et al. |
| 2005/0222477 A1 | 10/2005 | Grainger et al. |
| 2005/0228483 A1* | 10/2005 | Kaplan et al. ............... 623/1.15 |
| 2005/0228491 A1 | 10/2005 | Snyder et al. |
| 2005/0232968 A1 | 10/2005 | Palmaz et al. |
| 2005/0233965 A1 | 10/2005 | Schwartz et al. |
| 2005/0234538 A1 | 10/2005 | Litvack et al. |
| 2005/0240280 A1 | 10/2005 | Aliski et al. |
| 2005/0244459 A1 | 11/2005 | DeWitt et al. |
| 2005/0251245 A1* | 11/2005 | Sieradzki et al. ............. 623/1.39 |
| 2005/0251249 A1 | 11/2005 | Sahatjian |
| 2005/0252893 A1 | 11/2005 | Shapovalov et al. |
| 2005/0255707 A1 | 11/2005 | Hart et al. |
| 2005/0261760 A1 | 11/2005 | Weber |
| 2005/0266039 A1 | 12/2005 | Weber |
| 2005/0266040 A1 | 12/2005 | Gerberding |
| 2005/0266041 A1 | 12/2005 | Gerold et al. |
| 2005/0267560 A1 | 12/2005 | Bates et al. |
| 2005/0267561 A1 | 12/2005 | Jones et al. |
| 2005/0271703 A1 | 12/2005 | Anderson et al. |
| 2005/0271706 A1 | 12/2005 | Anderson et al. |
| 2005/0276837 A1 | 12/2005 | Anderson et al. |
| 2005/0278016 A1 | 12/2005 | Welsh et al. |
| 2005/0278021 A1 | 12/2005 | Bates et al. |
| 2005/0281863 A1 | 12/2005 | Anderson et al. |
| 2005/0283224 A1* | 12/2005 | King ............... 623/1.13 |
| 2005/0283229 A1* | 12/2005 | Dugan et al. ............... 623/1.38 |
| 2005/0287188 A1 | 12/2005 | Anderson et al. |
| 2006/0002979 A1 | 1/2006 | Ashammakhi et al. |
| 2006/0009839 A1* | 1/2006 | Tan ............... 623/1.38 |
| 2006/0013850 A1 | 1/2006 | Domb |
| 2006/0014039 A1* | 1/2006 | Zhang et al. ............... 428/615 |
| 2006/0015175 A1 | 1/2006 | Palmaz et al. |
| 2006/0015361 A1 | 1/2006 | Sattler et al. |
| 2006/0020742 A1 | 1/2006 | Au et al. |
| 2006/0025848 A1 | 2/2006 | Weber et al. |
| 2006/0035026 A1 | 2/2006 | Atanassoska et al. |
| 2006/0036281 A1 | 2/2006 | Patterson et al. |
| 2006/0036311 A1 | 2/2006 | Nakayama et al. |
| 2006/0038027 A1 | 2/2006 | O'Connor et al. |
| 2006/0040388 A1 | 2/2006 | Bromberg et al. |
| 2006/0041182 A1 | 2/2006 | Forbes et al. |
| 2006/0051397 A1 | 3/2006 | Maier et al. |
| 2006/0052744 A1 | 3/2006 | Weber |
| 2006/0052863 A1 | 3/2006 | Harder et al. |
| 2006/0052864 A1 | 3/2006 | Harder et al. |
| 2006/0058868 A1* | 3/2006 | Gale et al. ............... 623/1.15 |
| 2006/0062820 A1 | 3/2006 | Gertner et al. |
| 2006/0064160 A1 | 3/2006 | Gerold et al. |
| 2006/0067908 A1 | 3/2006 | Ding |
| 2006/0069427 A1 | 3/2006 | Savage et al. |
| 2006/0075044 A1 | 4/2006 | Fox et al. |
| 2006/0075092 A1 | 4/2006 | Kidokoro |
| 2006/0079958 A1 | 4/2006 | Stratford et al. |
| 2006/0085062 A1 | 4/2006 | Lee et al. |
| 2006/0085065 A1 | 4/2006 | Krause et al. |
| 2006/0088566 A1 | 4/2006 | Parsonage et al. |
| 2006/0088567 A1 | 4/2006 | Warner et al. |
| 2006/0088653 A1 | 4/2006 | Chappa et al. |
| 2006/0088666 A1 | 4/2006 | Kobrin et al. |
| 2006/0100696 A1 | 5/2006 | Atanasoska et al. |
| 2006/0115512 A1 | 6/2006 | Peacock et al. |
| 2006/0118236 A1 | 6/2006 | House et al. |
| 2006/0121080 A1 | 6/2006 | Lye et al. |
| 2006/0122694 A1* | 6/2006 | Stinson et al. ............... 623/1.34 |

| | | |
|---|---|---|
| 2006/0122697 A1 | 6/2006 | Shanley et al. |
| 2006/0124472 A1 | 6/2006 | Rokicki |
| 2006/0127266 A1 | 6/2006 | Miura et al. |
| 2006/0129215 A1 | 6/2006 | Helmus et al. |
| 2006/0129222 A1 | 6/2006 | Stinson |
| 2006/0129225 A1 | 6/2006 | Kopia et al. |
| 2006/0136048 A1 | 6/2006 | Pacetti et al. |
| 2006/0136051 A1 | 6/2006 | Furst et al. |
| 2006/0141156 A1 | 6/2006 | Viel et al. |
| 2006/0149352 A1 | 7/2006 | Schlum |
| 2006/0153729 A1 | 7/2006 | Stinson et al. |
| 2006/0155361 A1 | 7/2006 | Schomig et al. |
| 2006/0167543 A1 | 7/2006 | Bailey et al. |
| 2006/0177480 A1* | 8/2006 | Sung et al. .................... 424/426 |
| 2006/0178727 A1 | 8/2006 | Richter |
| 2006/0184235 A1 | 8/2006 | Rivron et al. |
| 2006/0193886 A1 | 8/2006 | Owens et al. |
| 2006/0193887 A1* | 8/2006 | Owens et al. ................ 424/423 |
| 2006/0193888 A1* | 8/2006 | Lye et al. ..................... 424/423 |
| 2006/0193889 A1 | 8/2006 | Spradlin et al. |
| 2006/0193890 A1 | 8/2006 | Owens et al. |
| 2006/0193892 A1* | 8/2006 | Furst et al. ................... 424/426 |
| 2006/0195142 A1 | 8/2006 | Shalaby |
| 2006/0198869 A1* | 9/2006 | Furst et al. ................... 424/426 |
| 2006/0199876 A1* | 9/2006 | Troczynski et al. ........... 523/115 |
| 2006/0200229 A1 | 9/2006 | Burgermeister et al. |
| 2006/0200231 A1 | 9/2006 | O'Brien et al. |
| 2006/0200232 A1 | 9/2006 | Phaneuf et al. |
| 2006/0200233 A1 | 9/2006 | Kujawski |
| 2006/0204441 A1 | 9/2006 | Atala et al. |
| 2006/0204445 A1 | 9/2006 | Atala et al. |
| 2006/0210595 A1 | 9/2006 | Singhvi et al. |
| 2006/0212108 A1 | 9/2006 | Tittelbach |
| 2006/0222679 A1 | 10/2006 | Shanley et al. |
| 2006/0222844 A1 | 10/2006 | Stinson |
| 2006/0224237 A1 | 10/2006 | Furst et al. |
| 2006/0229711 A1* | 10/2006 | Yan et al. .................... 623/1.38 |
| 2006/0229713 A1 | 10/2006 | Shanley et al. |
| 2006/0230476 A1 | 10/2006 | Atanasoska et al. |
| 2006/0233941 A1 | 10/2006 | Olson |
| 2006/0241739 A1 | 10/2006 | Besselink et al. |
| 2006/0251701 A1 | 11/2006 | Lynn et al. |
| 2006/0259133 A1* | 11/2006 | Sowinski et al. ............ 623/1.54 |
| 2006/0264138 A1* | 11/2006 | Sowinski et al. ............. 442/315 |
| 2006/0271156 A1* | 11/2006 | Ledergerber ................ 623/1.13 |
| 2006/0271168 A1 | 11/2006 | Kleine et al. |
| 2006/0271169 A1 | 11/2006 | Lye et al. |
| 2006/0271192 A1 | 11/2006 | Olsen et al. |
| 2006/0275554 A1 | 12/2006 | Zhao et al. |
| 2006/0276877 A1 | 12/2006 | Owens et al. |
| 2006/0276878 A1 | 12/2006 | Owens et al. |
| 2006/0276879 A1 | 12/2006 | Lye et al. |
| 2006/0276884 A1* | 12/2006 | Lye et al. ..................... 623/1.39 |
| 2006/0276885 A1* | 12/2006 | Lye et al. ..................... 623/1.39 |
| 2006/0280770 A1 | 12/2006 | Hossainy et al. |
| 2006/0287709 A1 | 12/2006 | Rao |
| 2006/0292388 A1 | 12/2006 | Palumbo et al. |
| 2007/0003589 A1 | 1/2007 | Astafieva et al. |
| 2007/0003596 A1 | 1/2007 | Tittelbach et al. |
| 2007/0020306 A1 | 1/2007 | Schultheiss |
| 2007/0027532 A1 | 2/2007 | Wang et al. |
| 2007/0032858 A1 | 2/2007 | Santos et al. |
| 2007/0032862 A1* | 2/2007 | Weber et al. ................ 623/1.34 |
| 2007/0032864 A1 | 2/2007 | Furst et al. |
| 2007/0034615 A1* | 2/2007 | Kleine .................... 219/121.72 |
| 2007/0036905 A1 | 2/2007 | Kramer |
| 2007/0038176 A1 | 2/2007 | Weber et al. |
| 2007/0038289 A1 | 2/2007 | Nishide et al. |
| 2007/0038290 A1* | 2/2007 | Huang et al. ................ 623/1.16 |
| 2007/0045252 A1* | 3/2007 | Kleine et al. ............ 219/121.69 |
| 2007/0048350 A1 | 3/2007 | Falotico et al. |
| 2007/0050007 A1* | 3/2007 | Kondyurin et al. .......... 623/1.13 |
| 2007/0050009 A1 | 3/2007 | Flanagan |
| 2007/0052497 A1 | 3/2007 | Tada |
| 2007/0055349 A1 | 3/2007 | Santos et al. |
| 2007/0055354 A1 | 3/2007 | Santos et al. |
| 2007/0055364 A1 | 3/2007 | Hossainy et al. |
| 2007/0059435 A1 | 3/2007 | Santos et al. |
| 2007/0065418 A1 | 3/2007 | Vallana et al. |
| 2007/0073385 A1 | 3/2007 | Schaeffer et al. |
| 2007/0073390 A1* | 3/2007 | Lee ............................. 623/1.46 |
| 2007/0077163 A1 | 4/2007 | Furst et al. |
| 2007/0100385 A1 | 5/2007 | Rawat et al. |
| 2007/0104753 A1* | 5/2007 | Flanagan ...................... 424/423 |
| 2007/0106347 A1 | 5/2007 | Lin |
| 2007/0106363 A1* | 5/2007 | Weber ......................... 623/1.11 |
| 2007/0123131 A1 | 5/2007 | Nguyen et al. |
| 2007/0123973 A1 | 5/2007 | Roth et al. |
| 2007/0129789 A1* | 6/2007 | Cottone et al. .............. 623/1.41 |
| 2007/0129792 A1 | 6/2007 | Picart et al. |
| 2007/0134288 A1 | 6/2007 | Parsonage et al. |
| 2007/0135908 A1 | 6/2007 | Zhao |
| 2007/0141106 A1 | 6/2007 | Bonutti et al. |
| 2007/0142897 A1* | 6/2007 | Consigny et al. ............ 623/1.15 |
| 2007/0142899 A1 | 6/2007 | Lootz et al. |
| 2007/0148251 A1 | 6/2007 | Hossainy et al. |
| 2007/0151093 A1 | 7/2007 | Curcio et al. |
| 2007/0156231 A1 | 7/2007 | Weber |
| 2007/0156248 A1 | 7/2007 | Marco et al. |
| 2007/0160641 A1* | 7/2007 | Jang ............................. 424/423 |
| 2007/0168016 A1 | 7/2007 | Gronemeyer et al. |
| 2007/0173923 A1* | 7/2007 | Savage et al. ................ 623/1.15 |
| 2007/0178129 A1 | 8/2007 | Flanagan |
| 2007/0181433 A1 | 8/2007 | Birdsall et al. |
| 2007/0184083 A1 | 8/2007 | Coughlin |
| 2007/0190104 A1 | 8/2007 | Kamath et al. |
| 2007/0191923 A1 | 8/2007 | Weber |
| 2007/0191928 A1 | 8/2007 | Rolando et al. |
| 2007/0191931 A1 | 8/2007 | Weber |
| 2007/0191943 A1 | 8/2007 | Shrivastava et al. |
| 2007/0197980 A1 | 8/2007 | Barry et al. |
| 2007/0202466 A1 | 8/2007 | Schwarz et al. |
| 2007/0207186 A1* | 9/2007 | Scanlon et al. ............... 424/424 |
| 2007/0208412 A1* | 9/2007 | Elmaleh ...................... 623/1.15 |
| 2007/0219626 A1 | 9/2007 | Rolando et al. |
| 2007/0224116 A1 | 9/2007 | Chandrasekaran et al. |
| 2007/0224244 A1 | 9/2007 | Weber et al. |
| 2007/0225799 A1 | 9/2007 | Doty |
| 2007/0244541 A1 | 10/2007 | Schulman |
| 2007/0244569 A1* | 10/2007 | Weber et al. ............... 623/23.75 |
| 2007/0250155 A1 | 10/2007 | Simpson |
| 2007/0250156 A1* | 10/2007 | Palmaz ........................ 623/1.39 |
| 2007/0250158 A1 | 10/2007 | Krivoruchko et al. |
| 2007/0255388 A1 | 11/2007 | Rudakov et al. |
| 2007/0255392 A1 | 11/2007 | Johnson |
| 2007/0264199 A1 | 11/2007 | Labhasetwar et al. |
| 2007/0264303 A1 | 11/2007 | Atanasoska et al. |
| 2007/0270940 A1 | 11/2007 | Doty |
| 2007/0270942 A1 | 11/2007 | Thomas |
| 2007/0281073 A1* | 12/2007 | Gale et al. .................... 427/2.25 |
| 2007/0281117 A1* | 12/2007 | Kaplan et al. ................ 428/35.7 |
| 2007/0282432 A1 | 12/2007 | Stinson et al. |
| 2007/0299509 A1 | 12/2007 | Ding |
| 2007/0299512 A1 | 12/2007 | Korzuschnik et al. |
| 2008/0003251 A1 | 1/2008 | Zhou |
| 2008/0003256 A1 | 1/2008 | Martens et al. |
| 2008/0003431 A1 | 1/2008 | Fellinger et al. |
| 2008/0004691 A1 | 1/2008 | Weber et al. |
| 2008/0031765 A1 | 2/2008 | Gerold et al. |
| 2008/0033522 A1* | 2/2008 | Grewe et al. ................ 623/1.11 |
| 2008/0033530 A1 | 2/2008 | Zberg et al. |
| 2008/0033531 A1 | 2/2008 | Barthel et al. |
| 2008/0033533 A1 | 2/2008 | Borck et al. |
| 2008/0033536 A1 | 2/2008 | Wittchow |
| 2008/0033537 A1 | 2/2008 | Tittelbach |
| 2008/0033538 A1 | 2/2008 | Borck et al. |
| 2008/0033539 A1 | 2/2008 | Sternberg et al. |
| 2008/0033576 A1 | 2/2008 | Gerold et al. |
| 2008/0038146 A1 | 2/2008 | Wachter et al. |
| 2008/0050413 A1 | 2/2008 | Horvers et al. |
| 2008/0051335 A1 | 2/2008 | Kleiner et al. |
| 2008/0051866 A1* | 2/2008 | Chen et al. .................. 623/1.11 |
| 2008/0051872 A1 | 2/2008 | Borck |
| 2008/0051881 A1* | 2/2008 | Feng et al. ................... 623/1.39 |
| 2008/0057105 A1 | 3/2008 | Atanasoska et al. |
| 2008/0058919 A1* | 3/2008 | Kramer-Brown et al. ... 623/1.34 |
| 2008/0058921 A1* | 3/2008 | Lindquist ..................... 623/1.42 |
| 2008/0058923 A1 | 3/2008 | Bertsch et al. |

| Publication | Date | Inventor(s) | Ref |
|---|---|---|---|
| 2008/0069854 A1* | 3/2008 | Xiao et al. | 424/423 |
| 2008/0069858 A1 | 3/2008 | Weber | |
| 2008/0071348 A1 | 3/2008 | Boismier et al. | |
| 2008/0071349 A1* | 3/2008 | Atanasoska et al. | 623/1.15 |
| 2008/0071350 A1* | 3/2008 | Stinson | 623/1.15 |
| 2008/0071351 A1* | 3/2008 | Flanagan et al. | 623/1.15 |
| 2008/0071352 A1* | 3/2008 | Weber et al. | 623/1.15 |
| 2008/0071353 A1* | 3/2008 | Weber et al. | 623/1.15 |
| 2008/0071355 A1* | 3/2008 | Weber et al. | 623/1.16 |
| 2008/0071357 A1 | 3/2008 | Girton et al. | |
| 2008/0071358 A1* | 3/2008 | Weber et al. | 623/1.42 |
| 2008/0082162 A1 | 4/2008 | Boismier et al. | |
| 2008/0086199 A1* | 4/2008 | Dave et al. | 623/1.42 |
| 2008/0086201 A1* | 4/2008 | Weber et al. | 623/1.42 |
| 2008/0090097 A1 | 4/2008 | Shaw et al. | |
| 2008/0097577 A1 | 4/2008 | Atanasoska et al. | |
| 2008/0103589 A1 | 5/2008 | Cheng et al. | |
| 2008/0103594 A1* | 5/2008 | Loffler et al. | 623/11.11 |
| 2008/0107890 A1 | 5/2008 | Bureau et al. | |
| 2008/0109072 A1 | 5/2008 | Girton | |
| 2008/0113083 A1 | 5/2008 | Sutermeister et al. | |
| 2008/0124373 A1* | 5/2008 | Xiao et al. | 424/423 |
| 2008/0131479 A1 | 6/2008 | Weber et al. | |
| 2008/0140172 A1 | 6/2008 | Carpenter et al. | |
| 2008/0140186 A1 | 6/2008 | Grignani et al. | |
| 2008/0145400 A1* | 6/2008 | Weber et al. | 424/423 |
| 2008/0147175 A1 | 6/2008 | Krivoruchko et al. | |
| 2008/0147177 A1 | 6/2008 | Scheuermann et al. | |
| 2008/0148002 A1 | 6/2008 | Fleming | |
| 2008/0152929 A1 | 6/2008 | Zhao | |
| 2008/0160166 A1* | 7/2008 | Rypacek et al. | 427/2.1 |
| 2008/0160259 A1* | 7/2008 | Nielson et al. | 428/148 |
| 2008/0161906 A1* | 7/2008 | Atanasoska et al. | 623/1.46 |
| 2008/0171929 A1 | 7/2008 | Katims | |
| 2008/0175885 A1 | 7/2008 | Asgari | |
| 2008/0177378 A1 | 7/2008 | Asgari | |
| 2008/0183269 A2* | 7/2008 | Kaplan et al. | 623/1.11 |
| 2008/0183277 A1 | 7/2008 | Atanasoska et al. | |
| 2008/0183278 A1 | 7/2008 | Atanasoska et al. | |
| 2008/0188927 A1 | 8/2008 | Rohde et al. | |
| 2008/0195170 A1 | 8/2008 | Asgari | |
| 2008/0195189 A1 | 8/2008 | Asgari | |
| 2008/0195198 A1 | 8/2008 | Asgari | |
| 2008/0208308 A1 | 8/2008 | Allen et al. | |
| 2008/0208313 A1 | 8/2008 | Yu et al. | |
| 2008/0208352 A1 | 8/2008 | Krivoruchko et al. | |
| 2008/0213377 A1 | 9/2008 | Bhatia et al. | |
| 2008/0215129 A1 | 9/2008 | Venturelli et al. | |
| 2008/0215139 A1 | 9/2008 | McMorrow et al. | |
| 2008/0215140 A1 | 9/2008 | Borck et al. | |
| 2008/0241218 A1* | 10/2008 | McMorrow et al. | 424/426 |
| 2008/0243113 A1 | 10/2008 | Shastri et al. | |
| 2008/0243230 A1 | 10/2008 | Lootz et al. | |
| 2008/0243231 A1 | 10/2008 | Flanagan et al. | |
| 2008/0243234 A1 | 10/2008 | Wilcox | |
| 2008/0243240 A1 | 10/2008 | Doty et al. | |
| 2008/0243242 A1 | 10/2008 | Kappelt et al. | |
| 2008/0249600 A1 | 10/2008 | Atanasoska et al. | |
| 2008/0249615 A1 | 10/2008 | Weber | |
| 2008/0255508 A1* | 10/2008 | Wang | 604/103.02 |
| 2008/0255509 A1 | 10/2008 | Wang | |
| 2008/0262589 A1 | 10/2008 | Nagura | |
| 2008/0268308 A1 | 10/2008 | Schilling et al. | |
| 2008/0269872 A1 | 10/2008 | Lootz et al. | |
| 2008/0288048 A1 | 11/2008 | Rolando et al. | |
| 2008/0290467 A1 | 11/2008 | Shue | |
| 2008/0294236 A1 | 11/2008 | Anand et al. | |
| 2008/0294246 A1 | 11/2008 | Scheuermann | |
| 2008/0306584 A1 | 12/2008 | Kramer-Brown | |
| 2009/0005862 A1 | 1/2009 | Nakatani et al. | |
| 2009/0012599 A1 | 1/2009 | Broome et al. | |
| 2009/0018639 A1* | 1/2009 | Kuehling | 623/1.15 |
| 2009/0018647 A1 | 1/2009 | Benco et al. | |
| 2009/0018648 A1 | 1/2009 | Wittchow | |
| 2009/0022771 A1 | 1/2009 | Lynn et al. | |
| 2009/0024199 A1 | 1/2009 | Birdsall et al. | |
| 2009/0024209 A1 | 1/2009 | Ozdil et al. | |
| 2009/0024210 A1 | 1/2009 | Klocke et al. | |
| 2009/0024211 A1 | 1/2009 | Wittchow | |
| 2009/0028785 A1 | 1/2009 | Clarke | |
| 2009/0030494 A1 | 1/2009 | Stefanadis et al. | |
| 2009/0030500 A1 | 1/2009 | Weber et al. | |
| 2009/0030504 A1* | 1/2009 | Weber et al. | 623/1.42 |
| 2009/0030506 A1 | 1/2009 | Klocke et al. | |
| 2009/0030507 A1 | 1/2009 | Klocke et al. | |
| 2009/0035351 A1 | 2/2009 | Berglund et al. | |
| 2009/0043330 A1 | 2/2009 | To | |
| 2009/0043374 A1 | 2/2009 | Nakano | |
| 2009/0043380 A1 | 2/2009 | Blaha et al. | |
| 2009/0048660 A1 | 2/2009 | Adden | |
| 2009/0062905 A1 | 3/2009 | Moore, Jr. et al. | |
| 2009/0069884 A1 | 3/2009 | Mueller | |
| 2009/0076588 A1 | 3/2009 | Weber | |
| 2009/0076596 A1 | 3/2009 | Adden et al. | |
| 2009/0081293 A1* | 3/2009 | Murase et al. | 424/484 |
| 2009/0081450 A1 | 3/2009 | Ascher et al. | |
| 2009/0088831 A1 | 4/2009 | Goto | |
| 2009/0088834 A1 | 4/2009 | Wang | |
| 2009/0093871 A1 | 4/2009 | Rea et al. | |
| 2009/0095715 A1* | 4/2009 | Sabaria | 216/83 |
| 2009/0118809 A1 | 5/2009 | Scheuermann et al. | |
| 2009/0118812 A1 | 5/2009 | Kokate et al. | |
| 2009/0118813 A1* | 5/2009 | Scheuermann et al. | 623/1.15 |
| 2009/0118814 A1 | 5/2009 | Schoenle et al. | |
| 2009/0118815 A1 | 5/2009 | Arcand et al. | |
| 2009/0118818 A1* | 5/2009 | Foss et al. | 623/1.42 |
| 2009/0118819 A1* | 5/2009 | Merz et al. | 623/1.42 |
| 2009/0118820 A1 | 5/2009 | Gregorich et al. | |
| 2009/0118821 A1* | 5/2009 | Scheuermann et al. | 623/1.49 |
| 2009/0118822 A1 | 5/2009 | Holman et al. | |
| 2009/0118823 A1 | 5/2009 | Atanasoska et al. | |
| 2009/0123517 A1 | 5/2009 | Flanagan et al. | |
| 2009/0123521 A1 | 5/2009 | Weber et al. | |
| 2009/0124956 A1* | 5/2009 | Swetlin et al. | 604/8 |
| 2009/0131540 A1 | 5/2009 | Hiromoto et al. | |
| 2009/0143855 A1* | 6/2009 | Weber et al. | 623/1.42 |
| 2009/0149942 A1* | 6/2009 | Edelman et al. | 623/1.15 |
| 2009/0157165 A1* | 6/2009 | Miller et al. | 623/1.15 |
| 2009/0157172 A1 | 6/2009 | Kokate et al. | |
| 2009/0164002 A1 | 6/2009 | Becher et al. | |
| 2009/0171452 A1 | 7/2009 | Yamamoto et al. | |
| 2009/0177273 A1 | 7/2009 | Piveteau et al. | |
| 2009/0182290 A1 | 7/2009 | Harder et al. | |
| 2009/0182337 A1 | 7/2009 | Stopek et al. | |
| 2009/0182425 A1 | 7/2009 | Duda et al. | |
| 2009/0192571 A1 | 7/2009 | Stett et al. | |
| 2009/0192594 A1 | 7/2009 | Borck | |
| 2009/0192595 A1 | 7/2009 | Nagura et al. | |
| 2009/0192596 A1 | 7/2009 | Adden | |
| 2009/0196899 A1 | 8/2009 | Birdsall et al. | |
| 2009/0198320 A1 | 8/2009 | Mueller et al. | |
| 2009/0202610 A1* | 8/2009 | Wilson | 424/426 |
| 2009/0204203 A1 | 8/2009 | Allen et al. | |
| 2009/0208428 A1 | 8/2009 | Hill et al. | |
| 2009/0208555 A1 | 8/2009 | Kuttler et al. | |
| 2009/0214373 A1 | 8/2009 | Stinson et al. | |
| 2009/0220612 A1 | 9/2009 | Perera | |
| 2009/0228037 A1 | 9/2009 | Rego | |
| 2009/0240323 A1 | 9/2009 | Wilcox | |
| 2009/0254171 A1 | 10/2009 | Heikkila | |
| 2009/0259300 A1 | 10/2009 | Dorogy, Jr. et al. | |
| 2009/0270979 A1 | 10/2009 | Adden | |
| 2009/0274737 A1 | 11/2009 | Borck | |
| 2009/0281613 A1* | 11/2009 | Atanasoska et al. | 623/1.15 |
| 2009/0287301 A1* | 11/2009 | Weber | 623/1.46 |
| 2009/0287302 A1 | 11/2009 | Thomas et al. | |
| 2009/0306584 A1 | 12/2009 | Schmidtlein et al. | |
| 2009/0306756 A1 | 12/2009 | Cho et al. | |
| 2009/0306765 A1* | 12/2009 | Weber | 623/1.15 |
| 2009/0306766 A1 | 12/2009 | Mcdermott et al. | |
| 2009/0311300 A1 | 12/2009 | Wittchow | |
| 2009/0312807 A1* | 12/2009 | Boudreault et al. | 606/86 R |
| 2009/0319035 A1* | 12/2009 | Terry | 623/1.46 |
| 2009/0324684 A1 | 12/2009 | Atanasoska et al. | |
| 2009/0326638 A1 | 12/2009 | Atanasoska et al. | |
| 2010/0008970 A1* | 1/2010 | O'Brien et al. | 424/426 |
| 2010/0010621 A1* | 1/2010 | Klocke | 623/1.16 |
| 2010/0010640 A1 | 1/2010 | Gerold et al. | |

| | | |
|---|---|---|
| 2010/0015206 A1 | 1/2010 | Flanagan et al. |
| 2010/0016940 A1 | 1/2010 | Shokoohi et al. |
| 2010/0021523 A1 | 1/2010 | Scheuermann et al. |
| 2010/0023112 A1 | 1/2010 | Borck et al. |
| 2010/0023116 A1 | 1/2010 | Borck et al. |
| 2010/0028436 A1 | 2/2010 | Ohrlander et al. |
| 2010/0030326 A1* | 2/2010 | Radhakrishnan et al. ... 623/1.46 |
| 2010/0034899 A1 | 2/2010 | Harder et al. |
| 2010/0042205 A1* | 2/2010 | Atanasoska et al. ......... 623/1.38 |
| 2010/0042206 A1* | 2/2010 | Yadav et al. ................. 623/1.42 |
| 2010/0047312 A1 | 2/2010 | Wittchow |
| 2010/0047324 A1* | 2/2010 | Fritz et al. ..................... 424/446 |
| 2010/0049146 A1* | 2/2010 | Nielsen et al. ................ 604/265 |
| 2010/0049296 A1* | 2/2010 | Sarasam et al. ............. 623/1.11 |
| 2010/0049299 A1 | 2/2010 | Popowski et al. |
| 2010/0049300 A1 | 2/2010 | Harder |
| 2010/0055151 A1 | 3/2010 | Flanagan |
| 2010/0057188 A1 | 3/2010 | Weber |
| 2010/0057197 A1* | 3/2010 | Weber et al. ................. 623/1.42 |
| 2010/0070256 A1 | 3/2010 | Venturelli et al. |
| 2010/0075162 A1 | 3/2010 | Yang et al. |
| 2010/0076544 A1* | 3/2010 | Hoffmann et al. ........... 623/1.15 |
| 2010/0076556 A1 | 3/2010 | Tomantschger et al. |
| 2010/0081735 A1* | 4/2010 | Mao et al. ....................... 524/27 |
| 2010/0082092 A1 | 4/2010 | Gerold |
| 2010/0087910 A1 | 4/2010 | Weber |
| 2010/0087911 A1 | 4/2010 | Mueller |
| 2010/0087914 A1 | 4/2010 | Bayer et al. |
| 2010/0087915 A1 | 4/2010 | Bayer et al. |
| 2010/0087916 A1 | 4/2010 | Bayer et al. |
| 2010/0092535 A1 | 4/2010 | Cook et al. |
| 2010/0106243 A1 | 4/2010 | Wittchow |
| 2010/0119576 A1 | 5/2010 | Harder et al. |
| 2010/0119581 A1 | 5/2010 | Gratz et al. |
| 2010/0121432 A1 | 5/2010 | Klocke et al. |
| 2010/0125325 A1 | 5/2010 | Allen et al. |
| 2010/0125328 A1 | 5/2010 | Flanagan |
| 2010/0131050 A1 | 5/2010 | Zhao |
| 2010/0131052 A1 | 5/2010 | Kappelt et al. |
| 2010/0161031 A1 | 6/2010 | Papirov et al. |
| 2010/0217370 A1* | 8/2010 | Scheuermann et al. ..... 623/1.11 |

FOREIGN PATENT DOCUMENTS

| | | |
|---|---|---|
| AU | 2003 203 722 | 11/2003 |
| CA | 2 235 031 | 10/1998 |
| CA | 2 346 857 | 5/2000 |
| CA | 2 371 800 | 8/2000 |
| DE | 198 11 033 | 8/1999 |
| DE | 198 56 983 | 12/1999 |
| DE | 103 57 281 | 7/2005 |
| DE | 103 61 941 | 7/2005 |
| DE | 10 2006 38236 | 2/2008 |
| EP | 0 006 544 | 6/1979 |
| EP | 0 337 035 | 10/1989 |
| EP | 0 337 035 | 11/1993 |
| EP | 0 615 769 | 9/1994 |
| EP | 0 923 389 | 7/1998 |
| EP | 0 923 912 | 6/1999 |
| EP | 0 966 979 | 12/1999 |
| EP | 0 972 563 | 1/2000 |
| EP | 1 054 644 | 11/2000 |
| EP | 1 071 490 | 1/2001 |
| EP | 1 222 901 | 7/2002 |
| EP | 1 260 214 | 11/2002 |
| EP | 1 270 023 | 1/2003 |
| EP | 1 273 314 | 1/2003 |
| EP | 1 370 306 | 12/2003 |
| EP | 0 923 912 | 2/2004 |
| EP | 1 389 471 | 2/2004 |
| EP | 1 393 766 | 3/2004 |
| EP | 1 419 793 | 5/2004 |
| EP | 0 951 877 | 6/2004 |
| EP | 1 260 214 | 6/2004 |
| EP | 0 875 218 | 2/2005 |
| EP | 1 389 471 | 8/2006 |
| EP | 1 733 746 | 12/2006 |
| EP | 1 752 167 | 2/2007 |
| EP | 1 835 042 | 9/2007 |
| EP | 1 750 780 | 10/2007 |
| EP | 1 562 565 | 3/2008 |
| EP | 1 642 551 | 12/2008 |
| EP | 1 653 885 | 4/2009 |
| EP | 1 632 256 | 9/2009 |
| EP | 2 139 535 | 1/2010 |
| EP | 1 883 380 | 3/2010 |
| EP | 2 189 169 | 5/2010 |
| RU | 2 218 242 | 12/2003 |
| WO | WO 93/04118 | 3/1993 |
| WO | WO 97/11724 | 4/1997 |
| WO | WO 98/48851 | 11/1998 |
| WO | WO 99/47077 | 9/1999 |
| WO | 99/64580 | 12/1999 |
| WO | WO 99/64580 | 12/1999 |
| WO | WO 00/25841 | 5/2000 |
| WO | WO 00/48660 | 8/2000 |
| WO | WO 00/51136 | 8/2000 |
| WO | WO 00/66190 | 11/2000 |
| WO | WO 01/49338 | 7/2001 |
| WO | WO 01/78906 | 10/2001 |
| WO | 01/80920 | 11/2001 |
| WO | WO 02/45764 | 6/2002 |
| WO | WO 02/47739 | 6/2002 |
| WO | WO 02/053202 | 7/2002 |
| WO | 03/002243 | 1/2003 |
| WO | WO 03/013396 | 2/2003 |
| WO | WO 03/035131 | 5/2003 |
| WO | WO 03/035278 | 5/2003 |
| WO | 03/046062 | 6/2003 |
| WO | WO 03/063733 | 8/2003 |
| WO | WO 03/094990 | 11/2003 |
| WO | 2004/025332 | 3/2004 |
| WO | WO 2004/093643 | 11/2004 |
| WO | WO 2005/065576 | 7/2005 |
| WO | 2005/079335 | 9/2005 |
| WO | WO 2005/110395 | 11/2005 |
| WO | WO 2005/118019 | 12/2005 |
| WO | 2006/008739 | 1/2006 |
| WO | 2006/060534 | 6/2006 |
| WO | WO 2006/060033 | 6/2006 |
| WO | WO 2006/065356 | 6/2006 |
| WO | 2006/077154 | 7/2006 |
| WO | WO 2006/108065 | 10/2006 |
| WO | WO 2007/005806 | 1/2007 |
| WO | 2007/013102 | 2/2007 |
| WO | WO 2007/018931 | 2/2007 |
| WO | 2007/035791 | 3/2007 |
| WO | WO 2007/024552 | 3/2007 |
| WO | 2007/079636 | 7/2007 |
| WO | WO 2007/082147 | 9/2007 |
| WO | 2008/036457 | 3/2008 |
| WO | 2008/036548 | 3/2008 |
| WO | 2008/036554 | 3/2008 |
| WO | WO 2008/062414 | 5/2008 |
| WO | WO 2008/117315 | 10/2008 |
| WO | 2009/045773 | 4/2009 |

OTHER PUBLICATIONS

Di Mario et al. "MOONLIGHT: a controlled registry of an iridium-oxide coated stent with angiographic follow up" *International Journal of Cardiology*. 2004 (95) 329-331.

Liu et al. "Sol-gel deposited Ti02 film on NiTi surgical alloy for biocompatibility improvement" *Thin Solid Films*. Apr. 1, 2003, pp. 225-230.

International Preliminary Report on Patentability in Application No. PCT/US2007/078476, mailed Mar. 26, 2009, 7 pages.

U.S. Appl. No. 10/849,742, filed May 20, 2004, Chen et al.
U.S. Appl. No. 60/826,002, filed Sep. 18, 2006, Girton et al.
U.S. Appl. No. 60/862,318, filed Oct. 20, 2006, Atanasoska et al.
U.S. Appl. No. 60/845,136, filed Sep. 15, 2006, Weber et al.

"Galvanic cell" printout from wikipedia, 2 pgs, printed Oct. 28, 2005.
"Galvanic corrosion", http://www.corrosion-doctors.org/Aircraft/galvdefi.htm, 3 pgs., printed Oct. 28, 2005.
"Galvanic series" printout from Wikipedia, p. 1 of 2, printed Oct. 28, 2005.
"Corrosion Theory and Corrosion Protection," *EM 1110-2-3400*, 1995, 8 pages.

Aghion et al., "Newly Developed Magnesium Alloys for Powertrain Applications," *JOM*, 2003, p. 30.
Andión et al., "Corrosion behaviour at the interface of steel bars embedded in cement slurries. Effect of phenol polymer coatings," *Corrosion Science*, 2002, 44:2805-2816.
Antipov et al., "Polyelectrolyte Multilayer Capsule Permeability Control," *Colloids and Surfaces A: Physiochem. Eng. Aspects*, 2002, 198-200, 535-541.
Antipov et al., "Polyelectrolyte Multilayer Capsules as Vehicles with Tunable Permeability," *Advances in Colloid and Interface Science*, 2004, 111:49-61.
Arts et al., "Polyphenols and disease risk in epidemiologic studies," *Am. J. Clin. Nutr.*, 2005, 81:317S-325S.
Artyukhin et al., "Layer-by-Layer Electrostatic Self-Assembly of Polyelectrolyte Nanoshells on Individual Carbon Nanotube Templates," *Langmuir*, 2004, 20:1442-1448.
Bakkar et al., "Improving corrosion resistance of magnesium-based alloys by surface modification with hydrogen by electrochemical ion reduction (EIR) and by plasma immersion ion implantation (PIII)," *Corrosion Science*, 2005, 47:1211-1225.
Berkland et al., "Controlling Surface Nano-structure Using Flow-Limited Field-Injection Electrostatic Spraying (FFESS) of poly(D,L-lactide-*co*-glycolide)," *Biomaterials*, 2004, 25:5649-5658.
Berry et al., "Functionalisation of magnetic nanoparticles for applications in biomedicine," *J. Phys. D: Appl. Phys.*, 2003, 36:R198-R206.
Bolz et al., "Effect of smooth, porous and fractal surface structure on the properties of an interface," *J. Materials Science: Materials in Medicine*, 1995, 6:844-848.
Brandau et al., "Nanoporous Ceramic Coatings for Synthesis of Radioactive Implants," *Journal of Nuclear Medicine Abstract Book*, Jun. 7, 2000, p. 244P, Abstract No. 1076.
Brückner et al., "Metal plasma immersion ion implantation and deposition (MPIIID): chromium on magnesium," *Surface and Coatings Technology*, 1998, 103-104, pp. 227-230.
Caruso et al., "Ultrathin Molybdenum Polyoxometalate-Polyelectrolyte Multilayer Films," *Langmuir*, 1998,14:3462-3465.
Casan-Pastor et al., "Polyoxometalates: From Inorganic Chemistry to Materials Science," *Frontiers in Bioscience*, 2004, 9:1759-1770.
Chaieb et al, "Inhibition of the corrosion of steel in 1 M HCl by eugenol derivatives," *Applied Surface Science*, 2005, 246:199-206.
Changwen et al., "Polyoxometalate-based organic-inorganic hybrid materials"; http://www.solgel.com/articles/oct01/changwen.asp, Retrieved from the Internet on Nov. 1, 2004 (17 pages).
Clemente-Leon et al., "Hybrid Langmuir-Blodgett Films Formed by Alternating Layers of Magnetic Polyoxometalate Clusters and Organic Donor Molecules—Towards the Preparation of Multifunctional Molecular Materials," *Adv. Mater.*, 2001, 13:574-577.
International Search Report/Written Opinion in PCT/US05/16600 mailed May 4, 2006, 15 pages.
International Preliminary Report on Patentability in PCT/US05/16600 mailed Nov. 30, 2006, 7 pages.
Authorized Officer Simin Baharlou, International Search Report/Written Opinion in PCT/US07/66568 mailed Oct. 8, 2007, 11 pages.
Authorized Officer Simin Baharlou, International Preliminary Report on Patentability in PCT/US07/66568 mailed Oct. 23, 2008, 10 pages.
International Search Report/Written Opinion in PCT/US07/78505 mailed Mar. 4, 2008, 10 pages.
International Preliminary Report on Patentability in PCT/US07/78505 mailed Mar. 26, 2009, 7 pages.
Authorized Officer Athina Nickitas-Etienne, International Search Report/Written Opinion in PCT/US07/78449, mailed Jan. 13, 2009, 24 pages.
Authorized Officer Athina Nickitas-Etienne, International Preliminary Report on Patentability in PCT/US07/78449 mailed Mar. 26, 2009, 9 pages.
Authorized Officer Simin Baharlou, International Search Report/Written Opinion in PCT/US07/75072 mailed Jan. 25, 2008, 21 pages.
Authorized Officer Simin Baharlou, International Preliminary Report on Patentability in PCT/US07/75072 mailed Feb.12, 2009, 9 pages.
International Search Report/Written Opinion in PCT/US07/78429 mailed Mar. 28, 2008, 13 pages.
International Preliminary Report on Patentability in PCT/US07/78429 mailed Apr. 2, 2009, 8 pages.
International Preliminary Report on Patentability in PCT/US07/78411 mailed Feb. 4, 2009, 8 pages.
Authorized Officer Elisabeth Reinecke, International Search Report/Written Opinion in PCT/US07/60137 mailed Jul. 27, 2007, 20 pages.
International Preliminary Report on Patentability in PCT/US07/78412 mailed Apr. 2, 2009, 7 pages.
Authorized Officer Trudy Hinterwimmer, International Search Report/Written Opinion in PCT/US07/78412 mailed Mar. 3, 2008, 10 pages.
Authorized Officer Joëlle Gerber, International Search Report/Written Opinion in PCT/US07/78450 mailed Nov. 19, 2008, 17 pages.
International Preliminary Report on Patentability in PCT/US07/78450 mailed Mar. 26, 2009, 7 pages.
International Search Report/Written Opinion in PCT/US07/73839 mailed Apr. 16, 2008, 17 pages.
International Preliminary Report on Patentability in PCT/US07/73839 mailed Apr. 2, 2009, 10 pages.
Authorized Officer Cecilia Giel-Barragán Ramos, International Search Report/Written Opinion in PCT/US07/79841 mailed Feb. 4, 2009, 21 pages.
Authorized Officer Athina Nickitas-Etienne, International Preliminary Report on Patentability in PCT/US07/79841 mailed Apr. 30, 2009, 7 pages.
Authorized Officer Joëlle Gerber, International Search Report/Written Opinion in PCT/US07/88888 mailed Jul. 13, 2009, 24 pages.
Authorized Officer Nora Lindner, International Preliminary Report on Patentability in PCT/US07/88888 mailed Jul. 30, 2009, 11 pages.
Authorized Officer Véronique van Loon-Mégard, International Search Report/Written Opinion in PCT/US08/75976 mailed Nov. 25, 2008, 20 pages.
Authorized Officer Trudy Hinterwimmer, International Search Report/Written Opinion in PCT/US09/49422 mailed Aug. 24, 2009, 10 pages.
Damiani et al., "Vasorelaxant effects on eugenol on rat thoracic aorta," *Vascular Pharmacol.*, 2003, 40:59-66.
Duygu, "Controlled Release Systems," http://www.biomed.metu.edu.tr/courses/term_papers/contr-rel-sys_duygu.htp (Dec. 30, 2005).
Eniola and Hammer, "Characterization of biodegradable drug delivery vehicles with the adhesive properties of leukocytes II: effect of degradation on targeting activity," *Biomaterials*, 2005, 26:661-670.
Farhat et al., "Corrosion Control Using Polyelectrolyte Multilayers," *Electrochemical and Solid State Letters*, 2002, 5(4):B13-B15.
Ferrando, "Review of Corrosion and Corrosion Control of Magnesium Alloys and Composites," *J. Mater. Eng.*, 1989, 11:299-313.
Fischer et al., "Hydrogen in magnesium alloys and magnesium interfaces: preparation, electronic properties and interdiffusion," *J. Less Common Metals*, 1991, 172:808-815.
Fontenier et al., "Study of a 'Platinum-Magnesium' Cell to Supply Current to a Pacemaker," *Bioelectrochemistry and Bioenergetics*, 1975, 2(2):106-123.
Frei, "On the Role of Vitamin C and Other Antioxidants in Atherogenesis and Vascular Dysfunction," *Proceedings—Society for Experimental Biology and Medicine*, 1999, 222:196-204.
Gomes et al., "Alternative tissue engineering scaffolds based on starch: processing methodologies, morphology, degradation and mechanical properties," *Materials Science and Engineering C*, 2002, 20:19-26.
Grassi et al., "Short-term administration of dark chocolate is followed by a significant increase in insulin sensitivity and a decrease in blood pressure in healthy persons," *Am. J. Clin. Nutr.*, 2005, 81(3):611-614.
Gray and Luan, "Protective coatings on magnesium and its alloys—a critical review," *J. Alloys Compounds*, 2002, 336:88-113.
Guo et al., "Manipulation of single-wall carbon nanotubes into aligned molecular layers," *Chem. Phys. Lett.*, 2002, 362:314-318.
Gurib-Fakim, "Medicinal plants: Traditions of yesterday and drugs of tomorrow," *Molecular Aspects of Medicine*, 2006, 27:1-93.

Hau et al., "Surface-Chemistry Technology for Microfluidics," *J. Micromech. Microeng.*, 2003, 13:272-278.

Huang et al., "A Review on Polymer Nanofibers by Electro-spinning and their Applications in Nanocomposites," *Composites Science & Technology*, 2003, 63:2223-2253.

Heublein et al., "Biocorrosion of magnesium alloys: a new principle in cardiovascular implant technology?" *Heart*, 2003, 89:651-656.

Heublein et al., "Bio-corrosion—a new principle for temporary cardiovascular implants?" *European Heart Journal, Journal of the European Society of Cardiology*, 2000, vol. 21, p. 286, Abstract No. P1605.

Heublein et al., "Degradation of Metallic Alloys—A New Principle in Stent Technology?" *The American Journal of Cardiology, Eleventh Annual Symposium Transcatheter Cardiovascular Therapeutics Abstracts*, Sep. 22, 1999.

Heublein et al., "Local Tissue Engineering by Biocorrosion Vision or Reality?" *The American Journal of Cardiology, TCT Abstracts/Poster*, Oct. 16, 2000.

Ito et al., "Antioxidant action of eugenol compounds; role of metal ion in the inhibition of lipid peroxidation," *Food Chem. Toxicol.*, 2005, 43:461-466.

Ivanova and Ivanov, "Mechanisms of the extracellular antioxidant defend," *Experimental Pathology and Parasitology*, 2000, 4:49-59.

Jiang, "A review of wet impregnation—An alternative method for the fabrication of high performance and nano-structured electrodes of solid oxide fuel cells," *Materials Science and Engineering A*, 2006, 418:199-210.

Kean and Davies, "Cathodic Protection," 7 pages, 1981; http://www.npl.co.uk/upload/pdf/cathodic_protection.pdf.

Kim et al., "Comprehensive study on vitamin C equivalent antioxidant capacity (VCEAC) of various polyphenols in scavenging a free radical and its structural relationship," *Crit. Rev. Food Sci. Nutr.*, 2004, 44(4):253-273.

Kurth et al., "Multilayer on Solid Planar Substrates: From Structure to Function", *Multi-layer Thin Films Sequential Assembly of Nanocomposite Materials*, 2003, Chapter 14, pp. 393-426.

Kurth et al., "Ultrathin Composite Films Incorporating the Nanoporous Isopolyoxomolybdate 'Keplerate' $(NH_4)_42[Mo_{132}O_{372}(CH_3COO)_{30}(H_2O)_{72}]$," *Chem. Mater.*, 2000, 12:2829-2831.

Lambert et al., "Inhibition of carcinogenesis by polyphenols: evidence from laboratory investigations," *Am. J.Clin. Nutr.*, 2005, 81:284S-291S.

Liao et al., "Fabrication of porous biodegradable polymer scaffolds using a solvent merging/particulate leaching method," *J. Biomed. Mater. Res.*, 2002, 59(4):676-681.

Liu, *Introduction to Corrosion and Protection*, Corrosion and Protection Centre, School of Materials, The University of Manchester, 2006, 36 pages.

Mamedov et al., "Molecular Design of Strong Single-Wall Carbon Nanotube/Polyelectrolyte Multilayer Composites," *Nature Materials*, 2002, 1:190-194.

Matsuoka et al., "Hyperthermia Using Magnetite Cationic Liposomes for Hamster Osteosarcoma," *BioMagnetic Research and Technology*, 2004, 2:3-8.

Medical Device Daily, "Conor Cites Positive 12-month Results for Its CoStar Stent", May 2005 (1 page).

Middleton and Tipton, "Synthetic Biodegradable Polymers as Medical Devices," http://www.devicelink.com/mpb/archive/98/03/002.html, Mar. 1998, 9 pages.

Mihailovic et al., "Unusual Magnetic State in Lithium-Doped $MoS_2$ Nanotubes," *Phys. Rev. Lett.*, 2003, 90 146401-1-4.

Mikos and Temenoff, "Formation of highly porous biodegradable scaffolds for tissue engineering," *Electronic Journal of Biotechnology*, 2000, 3(2):1-6.

Mohanty et al., "Effect of *Curcuma longa* and *Ocimum sanctum* on myocardial apoptosis in experimentally induced myocardial ischemic-reperfusion injury," *BMC Complementary and Alternative Medicine*, 2006, 6:3-14.

Mohanty et al. "Evaluation of soft tissue response to a poly[urethane urea]," *Biomaterials*, 1992, 13(10):651-656.

Moskaug et al., "Polyphenols and glutathione synthesis regulation," *Am. J. Clin. Nutr.*, 2005, 81:277S-283S.

Niemeyer et al., "Magnesium alloys as biodegradable metallic implant materials for cardiovascularic and orthopaedic surgery," *Euromat 2001, 7th European Conference on Advanced Materials and Processes*, Jun. 10-14, 2001 (Abstract).

Park et al., "Microstructural change and precipitation hardening in melt-spun Mg—X—Ca alloys," *Science and Technology of Advanced Materials*, 2001, 2:73-78.

Peuster et al., "Long-term biocompatibility of a corrodible peripheral iron stent in the porcine of descending aorta," *Biomaterials*, 2006, 27:4955-4962.

Peuster et al., "A novel approach to temporary stenting: degradable cardiovascular stents produced from corrodible metal-results 6-18 months after implantation into New Zealand white rabbits," *Heart*, 2001, 86(5): 563-569.

Remskar et al., "Self-Assembly of Subnanometer-Diameter Single-Wall $MoS_2$ Nanotubes," *Science*, 2001,292:479-481.

Rutledge et al., "Electrostatic Spinning and Properties of Ultrafine Fibers," *National Textile Center Annual Report*, Nov. 2001, M01-D22, pp. 1-10.

Satoh et al., "Effect of Antioxidants on Radical Intensity and Cytotoxic Activity of Eugenol," *Anticancer Res.*,1998, 18:1549-1552.

Sawitowski et al., "Nanoporous Alumina Coatings for Medical Implants and Stents—Radiotherapy, Drug Delivery, Biological Compatibility," *Materials Research Society Symposium Proceedings*, 1999, 581:523-528.

Sawitowski, "New Drug Delivery Systems—Examples of Applied Nanotechnology," *VDE World Microtechnologies Congress*, Sep. 25-27, 2000, Expo 2000, Hannover, Germany, Proveeds vol. 1, p. 343-346.

Sawyer et al., "Electrochemical Criteria in the Choice of Materials used in Vascular Prostheses," *Biophysical Mechanisms in Vascular Homeostasis and Intravascular Thrombosis*, 1965, pp. 337-348.

Schetky, "Shape Memory Alloys," *Encyclopedia of Chemical Technology* (3rd ed.), 1962, John Wiley & Sons, 20:726.

Shaw, "Corrosion Resistance of Magnesium Alloys," *ASM Handbook* vol. 13A: *Corrosion: Fundamentals, Testing, and Protection*, 2003, 5 pages.

Shenoy et al., "Role of Chain Entanglements on Fiber Formation During Electrospinning of Polymer Solutions: Good Solvent, Non-Specific Polymer-polymer Interaction Limit," *Polymer*, 2005, 46:3372-3384.

Shi et al., "A novel electrically conductive and biodegradable composite made of polypyrrole nanoparticles and polylactide," *Biomaterials*, 2004, 25:2477-2488.

Shin, "Experimental Characterization of Electro spinning: the Electrically Forced Jet and Instabilities," *Polymer*, 2001, 42:9955-9967.

Singh et al., "Electrocatalytic Activity of Electrodeposited Composite Films of Polypyrrole and $CoFe_2O_4$ Nanoparticles Towards Oxygen Reduction Reaction," *Electrochimica Acta*, 2004, 49:4605-4612.

Song et al., "Galvanic corrosion of magnesium alloy AZ91D in contact with an aluminium alloy, steel and zinc," *Corrosion Science*, 2004, 46:955-977.

Stoclet et al., "Vascular protection by dietary polyphenols," *Eur. J. Pharmacol.*, 2004, 500:299-313.

Straumal et al., "Vacuum arc deposition of protective layers on glass and polymer," *Thin Solid Films*, 2001, 383:224-226.

Suhaj, "Spice antioxidants isolation and their antiradical activity: a review," *J. Food Composition and Analysis*, 2006, 19:531-537.

Sukhorukov et al., "Comparative Analysis of Hollow and Filled Polyelectrolyte Microcapsules Templated on Melamine Formaldehyde and Carbonate Cores," *Macromol. Chem. Phys.*, 2004, 205:530-535.

Suslick et al., "The Photochemistry of Chromium, Manganese, and Iron Porphyrin Complexes," *J. Chem.*, 1992, 16:633-642.

Tada et al., "Distribution of pH during galvanic corrosion of a Zn/steel couple," *Electrochimica Acta*, 2004, 49:1019-1026.

Tan et al., "Systematic Parameter Study for Ultra-Fine Fiber Fabrication Via Electrospinning Process," *Polymer*, 2005, 46:6128-6134.

Tian et al., "Corrosion resistance improvement of magnesium alloy using nitrogen plasma ion implantation," *Surface & Coatings Technology*, 2005, 198:454-458.

Vermette et al., "Immobilized Liposome Layers for Drug Delivery Applications," *J. Controlled Release*, 2002, 80:179-195.
von Euler et al., "Cell proliferation and apoptosis in rat mammary cancer after electrochemical treatment (EChT)," *Bioelectrochemistry*, 2004, 62:57-65.
Vrbanic et al., "Air-Stable Monodispersed $Mo_6S_3I_6$ Nanowires," *Nanotechnology*, 2004, 15:635-638.
Wallerath et al., "A blend of polyphenols explains the stimulatory effect of red wine on human endothelial NO synthase," *Nitric Oxide*, 2005, 12(2):97-104.
Wan et al., "Influence of Plasma Immersion Ion Implantation on Corrosion Properties of Magnesium," South Jiaotong University, Chengdu, 2005.
Wang et al., "Nonlinear optical properties of thin iron films grown on MgO (100) by pulsed laser deposition," *Thin Solid Films*, 2005, 471:86-90.
Wang et al., "Characterisation of Severely Deformed Austenitic Stainless Steel Wire," *Materials Science and Technology*, 2005, 21:1323-1328.
Wang, "Recent development of non-platinum catalysts for oxygen reduction reaction," *J. Power Sources*, 2005, 152:1-15.
Weber et al., "Hardness and corrosion resistance of single-phase nitride and carbide on ion," *Materials Science and Engineering*, 1995, 99:205-210.
Weh et al., "Evolution of afractal-like surface structures in layers of polyacrylonitrile solutions by interfacial dynamic processes," *J. Colloid and Interface Science*, 2004, 271:407-415.
Widmer et al., "Manufacture of porous biodegradable polymer conduits by an extrusion process for guided tissue regeneration," *Biomaterials*, 1998, 19:1945-1955.
Wieneke et al., "Stent Coating: A New Approach in Interventional Cardiology," *Herz*, 2002, 27(6):518-526.
Williamson et al., "Bioavailability and bioefficacy of polyphenols in humans. II. Review of 93 intervention studies," *Am. J. Clin. Nutr.*, 2005, 81:243S-255S.
Witte et al., "In vitro and in vivo corrosion measurements of magnesium alloys," *Biomaterials*, 2006, 27:1013-1018.
Yamaguchi et al., "Mg2Si Coating Technology on Magnesium Alloys to Improve Corrosion and Wear Resistance", *JOM*, 2004, p. 343.
Yi et al., "Characterization of a bioactive nanotextured surface created by controlled chemical oxidation of titanium," *Surface Science*, 2006, 600:4613-4621.
You et al., "The Effect of Calcium Additions on the Oxidation Behavior in Magnesium Alloys," *Scripta Mat.*, 2000, 42:1089-1094.
Yu and Uan, "Sacrificial Mg film anode for cathodic protection of die cast Mg-9-wt.%-1 wt.%Zn alloy in NaCl aqueous solution," *Scripta Mat.*, 2006, 54:1253-1257.
Yue et al., "Improvement in the Corrosion Resistance of Magnesium ZK60/SiC Composite by Excimer Laser Surface Treatment," *Scripta Materialia*, 1998, 38(2):191-198.
Zeta Potential—An Introduction in 30 Minutes, Technical Note; http://www.nbtc.cornell.edu/facilities/downloads/Zeta%20potential%20-%20An%20introduction%20in%2030%20minutes.pdf, Retrieved from the Internet on May 9, 2005 (6 pages).
Zhang et al., "Natural Polyelectrolyte Films Based on Layer-by-Layer Deposition of Collagen and Hyaluronic Acid," *Biomaterials*, 2005, 26:3353-3361.
Zhang et al., "Improving multilayer films endurance by photoinduced interaction between Dawson-type polyoxometalate and diazo resin," *Materials Chemistry and Physics*, 2005, 90:57-52.
Zhang et al., "Ways for fabricating stable layer-by layer self-assemblies: combined ionic self-assembly and post chemical reaction," *Colloids and Surfaces A: physiochemical and Engineering Aspects*, 2002, pp. 198-200, 439-442.
Zhou et al., "Drug-loaded, Magnetic, hollow silica nanocomposites for nanomedicine," *Nanomedicine: Nanotechnology, Biology and Medicine*, 2005, 1:233-237.
Zucchi et al., "Influence of a silane treatment on the corrosion resistance of a WE43 magnesium alloy," *Surface Coatings Technol.*, 2006, 200:4136-4143.
"Best of the ACC Scientific Session 2002," Rev. Cardiovasc. Med., 2002, 3(2):85-104.

"Galvanic cell" printout from wikipedia, 5 pages, printed on Aug. 16. 2010.
"Galvanicc corrosion," http://www.corrosion-doctors.org/aircraft/galvdefi.htm, 3 pgs., printed Oct. 28, 2005.
"Galvanic series" printout from Wikipedia, p. 1 of 2, printed Oct. 28, 2005.
Aaltonen, "Atomic Layer Deposition of Noble Metal Thin Films," *University of Helsinki*, Apr. 8, 2005, pp. 1-71.
Aghion et al., "Newly Developed Magnesium Alloys for Powertrain Applications," p. 30 *JOM*, 2003, p. 30.
Albion Research Notes, Newsletter, Oct. 1994, 3(4): 1-4.
Anand et al., "Ion-exchange resins: carrying drug delivery forward," *DDT*, 2001, 6: 905-914.
Anderson et al., "A new conductive polymer as a replacement for chrome coatings," 2003 *Aerospace Coatings Removel and Coatings Conference*, May 20-22, 2003, Colorado Springs, CO, 7 pages.
Arts et al., "Polyphenols and disease risk in epidemiologic studies," *Am. J. Clin. Nutr.*, 2005, 81:317S-325S.
Ashtari et al. "An efficient method for recovery of target ssDNA based on amino-modified silica-coated magnetic nanoparticles" *Talanta* 67. (2005). 548-554.
Atta, "Electrochemical synthesis, characterization and some properties of a polymer derived from thioflavin S.," *European Polymer Journal*, 2005, 41: 3018-3025.
Australian Government, Department of Health and Aging, "Horizon Scanning Prioritising Summary-Biodegradable stents for coronary artery disease," *Horizon Scanning Network (ANZHSN)*, Aug. 2007, pp. 1-13.
Authorized Officer Athina Nickitas-Etienne, International Preliminary Report on Patentability in PCT/US07/78449 mailed Mar. 26, 2009, 9 pages.
Authorized officer Athina Nickitas-Etienne, International Preliminary Report on Patentability in PCT/US08/86639 mailed Jun. 24, 2010, 2 pages.
Authorized Officer Cecilia Giel-Barragan Ramos, International Search Report/Written in PCT/US07/79841 mailed Feb. 4, 2009, 11 pages.
Authorized Officer Elisabeth Reinecke, International Search Report/Written Opinion in PCT/US07/60137 mailed Jul. 27, 2007, 20 pages.
Authorized Officer Joëlle Gerber, International Search Report/Written Opinion in PCT/US07/78450 mailed Nov. 19, 2008, 17 pages.
Authorized Officer Joëlle Gerber, International Search Report/Written Opinion in PCT/US07/88888 mailed Jul. 13, 2009, 24 pages.
Authorized Officer Nora Lindner, International Preliminary Report on Patentability in PCT/US07/88888 mailed Jul. 30, 2009, 11 pages.
Authorized Officer Simin Baharlou, International Preliminary Report on Patentability in PCT/US07/66568 mailed Oct. 23, 2008, 10 pages.
Authorized Officer Simin Baharlou, International Preliminary Report on Patentability in PCT/US07/75072 mailed Feb. 12, 2009, 9 pages.
Authorized Officer Trudy Hinterwimmer, International Search Report/Written Opinion in PCT/US07/78412 mailed Mar. 3, 2008, 10 pages.
Authorized Officer Trudy Hinterwimmer, International Search Report/Written Opinion in PCT/US09/49422 mailed Aug. 24, 2009, 10 pages.
Authorized Officer Véronique van Loon-Megard, International Search Report/Written Opinion in PCT/US08/75976 mailed Nov. 25, 2008, 20 pages.
International Search Report/Written Opinion in PCT/US2009/43326 mailed Aug. 6, 2009, 9 pages.
Babapulle and Eisenberg, "Coatred stents for their prevention of restenosis: 2002, 106: 2849-2866 Part II," *Circulation*, 2002, 106: 2849-2866.
Bach et al., "Corrosion, Protection and Repassivation After the Deformation of Magnesium Alloys Coated With a Protective Magnesium Fluoride Layer," *JOM*, 2004, p. 343.
Bakkar et al., "Improving corrosion resistance of magnesium-based alloys by surface modification with hydrogen by electrochemical ion reduction (EIR) and by plasma immersion ion implantation (PIII)," *Corrosion Science*, 2005, 47:1211-1225.

Balasubramanian et al. "Dispersion and Stability Studies of Resorcinarene-Encapsulated Gold Nanoparticles." *Langmuir*, 2002, 1676-3681.

Bao, Y. et al. "Preparation of functionalized and gold-coated cobalt nanocrystals for biomedical applications." *Journal of Magnetism and Magnetic Materials*, 2005, 293:15-19.

Baurschmidt et al., "The Electrochemical Aspects of the Thrombogenicity of a Material," *J. Bioengineering*, 1977, 1:261-278.

Bekesi et al., "Efficient Submircon Processing of Metals with Femto," *Appl. Phys. A.*, Published Oct. 25, 2002, pp. 355-357.

Ben-Hamu et al., "Influence of Si, Ca and Ag addition on corrosion behaviour of new wrought Mg-Zn alloys," *Materials Science and Technology*, 2006, vol. 22, No. 10, pp. 1213-1218.

Bereket et al., "Electrochemical synthesis and anti-corrosive properties of polyaniline, poly(2-anisidine), and poly (aniline-co-2-anisidine) films on stainless steel," *Progress in Organic Coatings*, 2005, 54: 63-72.

Berkland et al., "Controlling Surface Nano-structure Using Flow-Limited Field-Injection Electrostatic Spraying (FFESS) of poly(D,L-lactide-co-glycolide)," *Biomaterials*, 2004, 25:5649-5658.

Bernkop-Schnurch, "Chitosan and its derivatives: potential excipients for peroral peptide delivery systems," *International J. Of Pharmaceutics*, 2000, 194: 1-13.

Berry et al., "Functionalisation of magnetic nanoparticles for applications in biomedicine," *J. Phys. D: Appl. Phys.*, 2003, 36:R198-R206.

Biercuk et al., "Low-temperature atomic-layer-deposition lift-off method for microelectronic and nanoelectronic applications," *Applied Physics Letters*, vol. 83, No. 12, Sep. 22, 2003, pages 2405-2407.

Blanusa et al., "Chelators as Antidotes of Metal Toxicity Therapeutic and Experimental Aspects," *Current Medicinal Chemistry*, 2005, vol. 12, pp. 2771-2794.

Bolz et al., "Effect of smooth, porous and fractal surface structure on the properties of an interface," *J. Materials Science: Materials in Medicine*, 1995, 844-848.

Bosiers et al., "Absorbable Metal stent for CLI in Infrapopliteal lesions: 1 year results," *CX 2005 Global Endovascular Forum*, Apr. 2005, pp. 1-23.

Brandau et al., "Nanoporous Ceramic Coatings for Synthesis of Radioactive Implants," *Journal of Nuclear Medicine Abstract Book*, Jun. 7, 2000, p. 244P, Abstract No. 1076.

Brückner et al., "Metal plasma immersion ion implantation and deposition (MPIID): chromium on magnesium," *Surface and Coatings Technology*, 1998, 103-104, pp. 227-230.

Brunatto and Muzart, "Influence of the gas mixture flow on the processing parameters of hollow cathode discharge ion sintering," *J. Phys. D.: Appl. Phys.*, 2007, 40: 3937-3944.

Brunner et al., "Porosity Tailored Growth of Black Anodic Layers on Magnesium in an Organic Electrolyte," *Journal of the Electrochemical Society*, vol. 156 (2), Dec. 12, 2008, pp. C62-C66.

Buescher et al., "Characterization of Wet-Chemically Nanostructured Stainless Steel Surfaces," *Mat. Res. Soc. Symp. Proc.*, 2001, 676:1-6.

Caruso et al., "Ultrathin Molybdenum Polyoxometalate-Polyelectrolyte Multilayer Films," *Langmuir*, 1998, 14:3462-3465.

Casan-Pastor et al., "Polyoxometalates: From Inorganic Chemistry to Materials Science," *Frontiers in Bioscience*, 2004, 9:1759-1770.

Chaieb et al, "Inhibition of the corrosion of steel in 1 M HCl by eugenol derivaives," *Applied Surface Science*, 2005, 246:199-206.

Chang et al., "Effect of Heat Treatment on Corrosion and Electrochemical behavior of Mg-3Nd-0.2Zn-0.4Zr (wt. %) alloy," *Science Direct, Electrochimica Acta* 52, 2007, 3160-3167.

Chang et al., "Templated sythesis of Gold-iron Alloy nanoparticles using pulsed laser deposition," *Nanotechnology*, vol. 17, 2006, pp. 5131-5135.

Changwen et al., "Polyoxometalate-based organic-inorganic hybrid materials," 2004, *Sol-Gel*, pg 1.

Chen et al., "Laser Cladding of Mg20A18o Powder on ZM5 Magnesium Alloy," *Corrosion Engineering, Science and Technology*, 2007, vol. 42, No. 2, pp. 130-136.

Cheng et al., "Electrogeneration and electrochemical properties of hybrid materials: polypyrrole doped with polyoxometalates $PW_{12-x}Mo_xM_{40}{}^{3-}$(x=0,3,6,12)," *Synthetic Metals*, 2002, 129: 53-59.

Cho et al., "Gold-coated iron nanoparticles: a novel magnetic resonance agent for $T_1$ and $T_2$ weighted imaging," *Nanotechnology*, vol. 17, 2006, pp. 640-644.

Chou et al., "Electrochemical treatment of mouse and rat fibrosarcomas with direct current," *Bioelectromagnetics*, 1997, 18:14-24.

Clemente-Leon et al., "Hybrid Langmuir-Blodgett Films Formed by Alternating Layers of Magnetic Polyoxometalate Clusters and Organic Donor Molecules—Towards the Preparation of Multifunctional Molecular Materials," *Adv. Mater.*, 2001, 13:574-577.

Cogger et al. "An Introduction to Electrochemical Impedance Measurement," *Solartron Analytical*, 1999, 2-14.

Conolly et al., "X-Ray microtomography studies of localized corrosion and transitions to stress corrosion cracking," *Materials Science and Technology*, 2006, vol. 22, No. 9, pp. 1076-1085.

Costa et al., "The effect of the magnetic field on the corrosion behavior of Nd-Fe-B permanent magnets." *Journal of Magnetism and Magnetic Material*, 278, 2004, pp. 348-358.

Damen et al., "Paclitaxel esters of malic acid as prodrugs with improved water solubility," *Bioorganic & Medicinal Chemistry*, 2000, 8: 427-432.

Damiani et al., "Vasorelaxant effects on eugenol on rat thoracic aorta," *Vascular Pharmacol.*, 2003, 40:59-66.

Davies, "Changing the salt, changing the drug," *The Pharmaceutical Journal*, 2001, 266: 322-323.

De Geest et al., "Self-rupturing Microcapsules," *Adv. Mater.*, 2005, vol. 17, pp. 2357-2361.

de Witte, "Analysis of the principal component of external casing corrosion in deep wells," *J. Appl. Electrochem.*, 1985, 15: 325-334.

Dexter, "Galvanic Corrosion," MAS Note, University of Delaware Sea Grant Marine Advisory Service, 2003.

Di Mario et al., "Drug-eluting bioabsorbable magnesium stent," *J. Interventional Cardiol.*, 2004, 17(6): 391-395.

Dowling et al., "Anti-bacterial silver coatings exhibiting enhanced activity through the addition of Platinum," *Surf. & Coatings Tech.*, 2003, 163-164:637-640.

Duncan et al., "Polymer-drug conjugates, PDEPY and PELT: basic principles for design and transfer from the laboratory to clinic," *Journal of Controlled Release*, 2001, 74: 135-146.

Duncan, "The dawning era of polymer 360 therapeutics," *Nature Reviews/Drug Discovery*, 2003, 2: 347-360.

Duygu, "Controlled Release Systems," http://www.biomed.metu.edu.tr/courses/term_papers/contr-rel-sys_duygu.htm (Dec. 30, 2005).

Eggebrecht et al., "Novel Magnetic Resonance-Compatible Coronary Stent: The Absorbable Magnesium-Alloy Stent," *Circulation*, 2005, 112: 303-304.

Eniola et al., "Characterization of Biodegradable Drug Delivery Vehicles with the Adhesive Properties of Leukocytes II: Effect of Degradation on Targeting Activity," *Biomaterials*, 2005, 26:661-670.

Erbel et al., "Absorbierbare Stents-Eine Vielversprechende Neuerung?" *Urban & Vogel*, No. 4, 2007, pp. 308-319.

Erbel et al., "Temporary scaffolding of coronary arteries with bioabsorbable magnesium stents: a prospective, non-randomised multicentre trial," *Lancet*, 2007, vol. 369, pp. 1869-1875.

Erne et al., "The Road to Bioabsorbable Stents: Reaching Clinical Reality?" *Cardio Vascular and Interventional Radiology*, Sep. 26, 2005, pp. 11-16.

International Preliminary report on Patentability received in PCT/US2007/078417, mailed Mar. 26, 2009, 8 pages.

International Preliminary Report on Patentability, received in PCT/US2007/078407, mailed Mar. 26, 2009, 6 pages.

European Search Report from EP 10159664.1, mailed Jun. 4, 2010, 3 pages.

International Preliminary Report on Patentability in PCT/US05/16600 mailed Nov. 30, 2006, 7 pages.

International Search Report/Written Opinion in PCT/US05/16600 mailed May 4, 2006, 15 pages.

International Preliminary Report on Patentability in PCT/US07/78476 mailed Mar. 26, 2009, 7 pages.
International Preliminary Report on Patentability in PCT/US07/78411 mailed Feb. 4, 2009, 8 pages.
International Preliminary Report on Patentability in PCT/US07/78412 mailed Apr. 2, 2009, 7 pages.
International Preliminary Report on Patentability in PCT/US07/78505 mailed Mar. 26, 2009, 7 pages.
International Preliminary Report on Patentability in PCT/US07/78450 mailed Mar. 26, 2009, 7 pages.
Falotico, "Cordis Fully Bioabsorbable Stent Program," *Euro PCR09*, May 22, 2009, pp. 1-21.
Fan et al., "Influence of Lanthanum on the microstructure, mechanical property and corrosion resistance of magnesium alloy," *J. Mater Sci*, 2006, vol. 41, pp. 5409-5416.
Farhat et al., "Corrosion Control Using Polyelectrolyte Multilayers," *Electrochemical and Solid State Letters*, 2002, 5(4):B13-B15.
Feng et al., "Sonochemical preparation of photochromic nanocomposite thin film based on polyoxometalates well dispersed in polyacrylamide," *Journal of Solid State Chemistry*, 2002, 169: 1-5.
Feng et al., "Superplasticity and texture of SiC whiskers in a magnesium-based composite," *Scripta Materialia*, 2005, 53: 361-365.
Ferguson et al., "Corrosion—Fatigue Performance of Magnesium Alloys," International Journal of Modern Physics B, vol. 17, Nos. 8 & 9, 2003, pp. 1601-1607.
Fernando, "Review of Corrosion and Corrosion Control of Magnesium Alloys and Composites," *J. Mater. Eng.*, 1989, 11:299-313.
Fischer et al., "Hydrogen in magnesium alloys and magnesium interfaces: preparation, electronic properties and interdiffusion," *J. Less-Common Metals*, 1991, 172:808-815.
Fontenier et al., "Study of a 'Platinum-Magnesium' Cell to Supply Current to a Pacemaker," *Bioelectrochemistry and Bioenergetics*, 1975, 2(2):106-123.
Fraunhofer EZRT, "Quantitative material analysis by dual energy computed tomography for industrial NDT applications," 2009, 1 pg.
Fraunhofer IIS—Poster (German), "Prinzip der hochauflosenden Comptuertomographie," 2009, 1 page.
Frei, "On the Role of Vitamin C and Other Antioxidants in Atherogenesis and Vascular Dysfunction," *Proceedings—Society for Experimental Biology and Medicine*, 1999, 222:196-204.
Gabrielli, Claude. "Use and Applications of Electrochemical Impedance Analytical, 1997, 1-102. Techniques," *Solartron Analytical*, 1997, 1-102.
Garner et al., "Polypyrrole-heparin composites as stimulus-responsive substrates for endothelial cell growth," *J. Biomed. Mater. Res.*, 1999, 44: 121-129.
Gettleman et al., "Measurement of in vivo corrosion rates in baboons, and correlation with in vitro tests," *Journal of Dental Research*, 1980, 59: 689-707.
Gettleman et al., "Materials Science: Measurement of in vivo Corrosion Rates in Baboons, and Correlation with in vitro Tests," Journal of Dental Research, 1980, vol. 59, pp. 689-707.
Gomes et al., "Alternative tissue engineering morphology, degradation and mechanical 20:19-26 scaffolds based on starch: processing methodologies, properties," *Materials Science and Engineering C*, 2002, 20:19-26.
Grassi et al., "Short-term administration of dark chocolate is followed by a significant increase in insulin sensitivity and a decrease in blood pressure in healthy persons," *Am. J. Clin. Nutr.*, 2005, 81(3):611-614.
Gray and Luan, "Protective coatings on magnesium and its alloys — A critical review" *J. Alloys Compounds*, 2002, 336:88-113.
Griffiths et al., "Future devices: bioabsorbable stents" *Br. J. Cardiol. (Acute & Cardiology)*, 2004, 11: AIC80-AIC84.
Grube, "Bioabsorbable Stents-The Boston Scientific & REVA Technology," *EuroPCR 2009*, 2009, pp. 1-27.
Guo et al., "Manipulation of single-wall carbon nanotubes into aligned molecular layers," *Chem. Phys. Lett.*, 2002, 362:314-318.
Guo et al., "Multi-layer LB films of single-wall carbon nanotubes," *Physica B*. 2002, 323:235-236.
Gurib-Fakim, "Medicinal plants: Traditions of yesterday and drugs of tomorrow," *Molecular Aspects of Medicine*, 2006, 27:1-93.

Haferkamp et al., "Magnesium-Base-Alloys as Impant-Material Steps to the Production of Thin Components," *Magnesium*, 2000, 159-164.
Hau et al., "Surface-Chemistry Technology for Microfluidies," *J. Micromech. Microeng.*, 2003,13;272-278.
Heublein et al., "Biocorrosion of magnesium alloys: a new principle in cardiovascular implant technology?" *Heart*, 2003, 89:651-656.
Heublein et al., "Degradation of Metallic Alloys—A New Principle in Stent Technology?" *he American Journal of Cardiology, Elevent Annual Symposium Transcatheter Cardiovascular Therapeutics Abstracts*, Sep. 22, 1999.
Heublein et al., "Bio-corrosion—a new principle for temporary cardiovascular implants?" *European Heart Journal, Journal of the European Society of Cardiology*, 2000, vol. 21, p. 286, Abstract No. P1605.
Heublein et al., "Local Tissue Engineering by Biocorrosion Vision or Reality?" *The American Journal of Cardiology, TCT Abstracts/Poster*, Oct. 16, 2000.
Huang et al., "A review on Polymer Nanofibers by Electro-spinning and their Applications in Nanocomposites," 2003, 63:2223-2253.
International Preliminary Report on Patentability in PCT/US07/73839 mailed Apr. 2, 2009.
International Preliminary Report on Patentability in PCT/US07/78429 mailed Apr. 2, 2009.
International Search Report and Written Opinion in PCT/US07/78449, mailed Jan. 13, 2009, 15 pages.
International Search Report and Written Opinion mailed Jan. 25, 2008 in PCT/US07/75072, 14 pages.
International Search Report for PCT/US07/66568 daed Oct. 8, 2007, 15 pages.
International Search Report from PCT/US 03/20215, mailed Nov. 11, 2003, 4 pages.
International Search Report/Written Opinion in PCT/US07/73839 mailed Apr. 16, 2008, 16 pages.
International Search Report/Written Opinion in PCT/US07/78411 mailed Mar. 6, 2008, 12 pages.
International Search Report/Written Opinion in PCT/US07/78429 mailed Mar. 28, 2008, 14 pages.
International Search Report/Written Opinion in PCT/US07/78505 mailed Mar. 4, 2008, 10 pages.
Jiang, "A review of wet impregnation—An alternative method for the fabrication of high performance and nano-structured electrodes of solid oxide fuel cells," *Materials Science and Engineering A*, 2006, 418:199-210.
Kean and Davies, "Cathodic Protection," 7 pages, 1981; http://www.npl.co.uk/upload/pdf/cathodic_protection.
Kim et al., "Comprehensive study on vitamin C equivalent antioxidant capacity (VCEAC) of various polyphenols in scavenging a free radical and its structural relationship," *Crit. Rev. Food Sci. Nutr.*, 2004, 44(4):253-273.
Kim et al., "Effect of Anti-Oxidant (Carvedilol and Probucol) Loaded Stents in a Porcine Coronary Restenosis Model," *Circ. J.*, 2005, 69:101-106.
Kong et al., "Polyelectrolyte-functionalized multiwalled carbon nanotubes: preparation, characterization and layer-by-layer self assembly," *Polymer*, 2005, 46:2472-2485.
Kumar et al., "Polyanhydrides: an overview," *Advanced Drug Delivery Reviews*, 2002, 54:889-910.
Kurth et al., "Multilayer on Solid Planar Substrates: From Structure to Function", *Multi-layer Thin Films Sequential Assembly of Nanocomposite Materials*, 2003, Chapter 14, pp. 393-426.
Kurth et al., "Ultrathin Composite Films Incorporating the Nanoporous Isopolyoxomolybdate 'Keplerate' $(NH_4)_{42}[Mo_{132}O_{372}(CH_3COO)_{30}(H_20)_{72}]$," *Chem. Mater.*, 2000, 12:2829-2831.
Kutsenko et al., "Structural Changes in Mg Alloy induced by plasma immersion ion implantation of Ag," *Acta Materialia*, 2004, 52:4329-4335.
Lambert et al., "Inhibition of carcinogenesis by polyphenols: evidence from laboratory investigations," *Am. J. Clin. Nutr.*, 2005, 81(suppl):284S-291S.
Lee et al., "Retentive and compressive strengths of modified zinc oxide-eugenol cements," *J. Dentistry*, 2000, 28:69-75.

Liao et al., "Fabrication of porous biodegradable polymer scaffolds using a solvent merging/particulate leaching method," *J. Biomed. Mater. Res.*, 2002, 59:676-681.

Lin et al., "Micropatterning proteins and cells on polylactic acid and poly(lactide-co-glycolide)," *Biomaterials*, 2005, 26:3655-3662.

Liu et al., "Characterizations of polypyrrole (PPy) nano-tubules made by templated ac electropolymerization," *European Polymer Journal*, 2005, 41: 2117-2121.

Liu et al., "Layer-By-Layer Ionic Self-Assembly of Au Colloids Into Multilayer Thin-Films with Bulk Metal Conductivity," *Chemical Physics Letters*, 1998, 298:315-319.

Liu et al., "Functional Polyoxometalate Thin Films via Electrostatic Layer-by-Layer Self-Assembly," *Journal of Cluster Science*, 2003, 14:405-419.

Liu et al., "Sol-gel deposited TiO2 film on NiTi surgical alloy for biocompatibility improvement," *Thin Solid Films*, 2003, 429:225-230.

Liu, *Introduction to Corrosion and Protection*, Corrosion and Protection Centre, School of Materials, The University of Manchester, 2006, 36 pages.

Lu et al., "Theoretical analysis of calcium phosphate precipitation in simulated body fluid," *Biomaterials*, 2005, 26:1097-1108.

Maier et al., "High concentrations of magnesium modulate vascular endothelial cell behaviour in vitro," *Biochim. Biophys. Acta*, 2004, 1689:6-12.

Mansfeld, Florian. "Analysis and Interpretation of EIS Data for Metals and Alloys," *Solartron Analytical*, 1999, 1-77.

Matsuoka et al., "Hyperthermia Using Magnetite Cationic Liposomes for Hamster Osteosarcoma," *Biomagnetic Research and Technology*, Mar. 25, 2004, pp. 1-6.

Medical Device Daily, "Conor Cites Positive 12-month Results for Its CoStar Stent", May 2005 (1 page).

Meng Han, "Laser nitriding of metals: Influences of the ambient pressure and the pulse duration," 2001, Dissertation, Georg-Aug.-Universitat Gottingen, 134 pages.

Middleton and Tipton, "*Synthetic Biodegradable Polymers as Medical Devices*,"http://www.devicelink.com/mpb/archive/98/03/002.html, Mar. 1998, 9 pages.

Mihailovic et al., "Unusual Magnetic State in Lithium-Doped $MoS_2$ Nanotubes," *Phys. Rev. Lett.*, 2003, 90 146401-1-4.

Mikos and Temenoff, "Formation of highly porous biodegradable scaffolds for tissue engineering," *Electronic Journal of Biotechnology*, 2000, 3(2):114-119.

Mohanty et al. "Evaluation of soft tissue response to a poly[urethane urea]," *Biomaterials*, 1992,13(10):651-656.

Mohanty et al., "Effect of *Curcuma longa* and *Ocimum sanctum* on myocardial apoptosis in experimentally induced myocardial ischemic-reperfusion injury," *BMC Complementary and Alternative Medicine*, 2006, 6:3-14.

Molnar and Garai, "Plant-derived anti-inflammatory compounds affect MIF tautomerase activity," *International Immunopharmacology*, 2005, 5:849-856.

Moskaug et al., "Polyphenols and glutathione synthesis regulation," *Am. J. Clin. Nutr.*, 2005, 81 (suppl):277S-283 S.

Naderi et al., "Effect of some volatile oils on the affinity of intact and oxidized low-density lipoproteins for adrenal cell surface receptors," *Mol. Cell. Biochem.*, 2004, 267:59-66.

Niemeyer et al., "Magnesium alloys as biodegradable metallic implant materials for cardiovascularic and orthopaedic surgery," *Euromat* 2001, 7$^{th}$ *European Conference on Advanced Materials and Processes*, Jun. 10-14, 2001 (Abstract).

Niinisto, "Atomic Layer deposition: A key technology for the controlled growth of oxide thin films for advanced applications," *Proc. Estonian Acad. Sci. Phys. Math.*, 2003, 52(3):266-276.

Nilsson et al., "Development of a dosage method for electrochemical treatment of tumours: a simplified mathematical model," *Bioelectrochemistry and Bioenergetics*, 1998, 47:11-18.

Ormiston et al., "Bioabsorbable Coronary Stents," *Circulation Cardiovasc Intervent*, vol. 2, 2009, pp. 255-260.

Ou et al., "Protective effects of eugenol against oxidized LDL-induced cytotoxicity and adhesion molecule expression in endothelial cells," *Food Chem. Toxicol.*, 2006, 44:1485-1495.

Park et al., "Microstructural change and precipitation hardening in melt-spun Mg-X-Ca alloys," *Science and Technology of Advanced Materials*, 2001, 2:73-78.

Peuster et al. "Long-term biocompatibility of a corrodible peripheral iron stent in the porcine of descending aorta," *Biomaterials*, 2006, 4955-4962.

Peuster et al., "A novel approach to temporary stenting: degradable cardiovascular stents produced from corrodible metal-results 6-18 months after implantation into New Zealand white rabbits," *Heart*, 2001, 86(5):563-569.

Peuster et al., "Are resorbable implants about to become a reality," *Cardiol Young*, 2006, 16:107-116.

Pinto Slattow et al., "Optical coherence tomography and intravascular ultrasound imaging of bioabsorbable magnesium stent degradation in porcine coronary arteries," *Cardiovascular Revascularization Medicine* 9, (2008) pp. 248-254.

Prasse et al., "Electric Anisotropy of Carbon Nanofibre/Epoxy Resin Composites Due to Electric Field Induced Alignment," *Composites Science and Technology*, 2003, 63:1835-1841.

Purushothaman et al. "Reducing Mass-Transport Limitations by Application of Special Pulsed Current Modes". *Journal of the Electrochemical Society*, 152 (4), 2005, J33-J39.

Qasem et al., "Kinetics of paclitaxel 2'-N-methylpyridinium mesylate decomposition," *AAPS PharmSciTech*, 2003, 4(2), Article 21, 8 pages.

Quinard et al., "Development of metal/polymer mixtures for micro powder injection moulding," 10th *ESAFORM Conference on Material Forming*, 2007, pp. 933-939.

Ratnam et al., "Role of antioxidants in prophylaxis and therapy: A pharmaceutical perspective," *J. Controlled Release*, 2006, 113:189-207.

Remskar et al., "Self-Assembly of Subnanometer-Diameter Single-Wall $MoS_2$ Nanotubes," *Science*, 2001, 292:479-481.

Rezwan et al., "Biodegradable and bio active porous polymer/inorganic composite scaffolds for bone tissue engineering," *Biomaterials*, 2006, 27:3413-3431.

Rhule et al., "Polyoxometalates in Medicine," *Chem. Rev.*, 1998, 98:327-357.

Russell-Stevens et al., "The effect of thermal cycling on the properties of a carbon fibre reinforced magnesium composite," *Materials Science and Engineering A*, 2005, 397: 249-256.

Rutledge et al., "Electrostatic Spinning and Properties of Ultrafine Fibers," *National Textile Center Annual Report*, Nov. 2001, M01-D22, pp. 1-10.

Ryan et al., "Fabrication methods of porous metals for use in orthopaedic applications," *Biomaterials*, 2006, 27:2651-2670.

Sastry et al., "DNA-Mediated Electrostatic Assembly of Gold Nanoparticles into Linear Arrays by a Simple Drop-Coating Procedure," *Appl. Phys. Lett.*, 2001, 78:2943-2945.

Satoh et al., "Effect of Antioxidants on Radical Intensity and Cytotoxic Activity of Eugenol," *Anticancer Res.*, 1998, 18:1549-1552.

Sawitowski et al., "Nanoporous Alumina Coatings for Medical Implants and Stents—Radiotherapy, Drug Delivery, Biological Compatibility," *Materials Research Society Symposium Proceedings*, 1999, 581:523-528.

Sawitowski, "New Drug Delivery Systems—Examples of Applied Nanotechnology," *VDE World Microtechnologies Congress*, Sep. 25-27, 2000, Expo 2000, Hannover, Germany, Proveeds vol. 1, p. 343-346.

Sawyer et al., "Electrochemical Criteria in the Choice of Materials used in Vascular Prostheses," *Biophysical Mechanisms in Vascular Homeostasis and Intravascular Thrombosis*, 1965, pp. 337-348.

Schetky, "Shape Memory Alloys," *Encyclopedia of Chemical Technology* (3rd ed.), 1982, John Wiley & Sons, 20:726.

Shaw, "Corrosion Resistance of Magnesium Alloys," *ASM Handbook* vol. 13A: *Corrosion: Fundamentals, Testing, and Protection*, 2003, 5 pages.

Shenoy et al., "Role of Chain Entanglements on Fiber Formation During Electrospinning of Polymer Solutions: Good Solvent, Non-Specific Polymer-polymer Interaction Limit, " *Polymer*, 2005,46:3372-3384.

Shi et al., "A novel electrically conductive and biodegradable composite made of polypyrrole nanoparticles and polylactide," *Biomaterials*, 2004, 25:2477-2488.

Shin, "Experimental Characterization of Electrospinning: the Electrically Forced Jet and Instabilities," *Polymer*, 2001, 42:9955-9967.

Singh et al., "Electrocatalytic Activity of Electrodeposited Composite Films of Polypyrrole and $CoFe_2O_4$ Nanoparticles Towards Oxygen 4612 Reduction Reaction," *Electrochimica Acta*, 2004, 49:4605-4612.

Song et al., "Galvanic corrosion of magnesium alloy AZ91D in contact with an aluminium alloy, steel and zinc," *Corrosion Science*, 2004, 46:955-977.

Stoclet et al., "Vascular protection by dietary polyphenols," *Eur. J. Pharmacol.*, 2004, 500:299-313.

Straumal et al., "Vacuum arc deposition of protective layers on glass and polymer," *Thin Solid Films*,2001, 383:224-226.

Suhaj, "Spice antioxidants isolation and their antiradical activity: a review," *J. Food Composition and Analysis*, 2006, 19:531-537.

Sukhorukov et al., "Comparative Analysis of Hollow and Filled Polyelectrolyte Microcapsules Templated on Melamine Formaldehyde and Carbonate Cores," *Macromol. Chem. Phys.*, 2004, 205:530-535.

Suslick et al., "The photochemistry of chromium, manganese, and iron porphytin complexes," J. Chem., 1992, 16:633-642.

Tada et al., "Distribution of pH during galvanic corrosion of a Zn/steel couple," *Electrochimica Acta*, 2004, 49:1019-1026.

Tan et al., "Systematic Parameter Study for Ultra-Fine Fiber Fabrication Via Electrospinning Process," *Polymer*, 2005, 46:6128-6134.

Tian et al., "Corrosion resistance improvement of magnesium alloy using nitrogen plasma ion implantation," *Surface & Coatings Technology*, 2005, 198:454-458.

Vermette et al., "Immobilized Liposome Layers for Drug Delivery Applications," *J. Controlled Release*, 2002, 80:179-195.

Virtanen, "Corrosion of Biomedical Implant Materials," *Corrosion of Biomedical Implant Materials*, vol. 26, Nos. 2-3, 2008, pp. 147-171.

von Euler et al., "Cell proliferation and apoptosis in rat mammary cancer after electrochemical treatment (EChT)," *Bioelectrochemistry*, 2004, 62:57-65.

Vrbanic et al., "Air-Stable Monodispersed $Mo_6S_3I_6$ Nanowires," *Nanotechnology*, 2004, 15:635-638.

Waksman et al., "Early-and Long-Term Intravascular Ultrasound and Angiographic Findings After Bioabsorbable Magnesium Stent Implantation in Human Coronary Arteries," *JACC: Cardiovascular Interventions*, vol. 2, No. 4, 2009, pp. 1-9.

Wallerath et al., "A blend of polyphenolic compounds explains the stimulatory effect of red wine on human endothelial NO synthase," *Nitric Oxide*, 2005, 12:97-104.

Wan et al., "Preparation and characterization of porous conducting poly(DL-lactide) composite membrances," *Journal of Membrane Science*, 2005, 246: 193-201.

Wan et al., "Influence of Plasma Immersion Ion Implantation on Corrosion Properties of Magnesium," *Southwest Jiaotong University*, 2005, Chengu, 11 pages.

Wang et al., "Nonlinear optical properties of thin iron films grown on MgO (100) by uplsed laser deposition," *Thin Solid Films*, 2005, 471:86-90.

Wang et al., "Characterisation of Severely Deformed Austenitic Stainless Steel Wire." *Materials Science and Technology*, 2005, 21(11):1323-1328.

Wang, "Recent development of non-platinum catalysts for oxygen reduction reaction," *J. PowerSources*, 2005, 152:1-15.

Weber et al., "Hardness and corrosion resistance of single-phase nitride and carbide on ion," *Materials Science and Engineering*, 1995, 99:205-210.

Weh et al., "Evolution of afractal-like surface structures in layers of polyacrylonitrile solutions by interfacial dynamic processes," *J. Colloid and Interface Science*, 2004, 271: 407-415.

Witte, "The history of biodegradable magnesium implants: A review," *Acta Biomaterialia*, 2010, 6:1680-1692.

Xu et al., "In Vivo corrosion behaviouc of Mg-MnZn alloy for bone implant application," *Journal of Biomedical Materials Research Part A*, Jun. 4, 2007, pp. 703-711.

Yun et al., "Revolutionizing Biodegradable Materials," *Materials Today*, Oct. 2009, vol. 12, No. 10, pp. 1-11.

Zarras et al., "Progress in using conductive polymers as corrosion-inhibiting coatings, " *Radiation Physics and Chemistry*, 2003, 68: 387-394.

Zberg et al., "MgZnCa glasses without clinically observable hydrogen evolution for biodegradable implants," *Nature materials*, Sep. 27, 2009, vol. 8, pp. 887-891.

Zheng, "Symposium on Biodegradable/Biocorroded metallic materials," Nov. 24, 2009, pp. 1-74.

Li et al., "The corrosion inhibition of the self assembled Au, and Ag nonoparticles films on the surface of copper," Colloids and Surfaces A: Physiochem. Eng. Aspects, 2006, 273: 16-23.

Viswanathamurthi et al., "Preparation and morphology of niobuim oxide fibres by electrospinning," *Chemical Physics Letters*, 2003, 374: 79-84.

Authorized Officer Henrique Amaro, International Preliminary Report on Patentability from PCT/US09/043326 mailed Nov. 18, 2010, 7 pages.

Authorized Officer Jasmine Messemanne, International Search Report from PCT/US09/051965 mailed Aug. 20, 2010, 13 pages.

Authorized Officer Jasmine Messemanne, International Preliminary Report on Patentability from PCT/US09/051965 mailed Feb. 10, 2011, 8 pages.

Authorized Officer Antonio Espuch, International Preliminary Report on Patentability in PCT/US09/49422 mailed Jan. 13, 2011, 7 pages.

Authorized Officer Aurore Schneider, International Preliminary Report on Patentability from PCT/US2010/042772 mailed Feb. 4, 2011, 9 pages.

Authorized Officer Henrique Amaro, International Preliminary Report on Patentability in PCT/US2009/43326 mailed Nov. 18, 2010, 7 pages.

Authorized Officer Antoine Laurent, International Preliminary Report on Patentability in PCT/US09/046750 mailed Dec. 23, 2010, 8 pages.

Wikipedia, the Free Encyclopedia, "Galvanic Corrosion." <http://en.wikipedia.org/wiki/Galvanic_corrosion> on Mar. 11, 2011, 7 pages.

Authorized Officer Mary Celine, International Search Report from PCT/US2010/060412 mailed Feb. 21, 2011, 10 pages.

Dumas et al., "Characterization of magnesium fluoride thin films produced by argon ion beam-assisted deposition," *Thin Solid Films*, 2001, pp. 61-68.

Authorized Officer Razik Menidjel, International Preliminary Report on Patentability from PCT/US09/059424, mailed May 5, 2011, 8 pages.

US 6,533,715, 03/2003, Hossainy et al. (withdrawn)

* cited by examiner

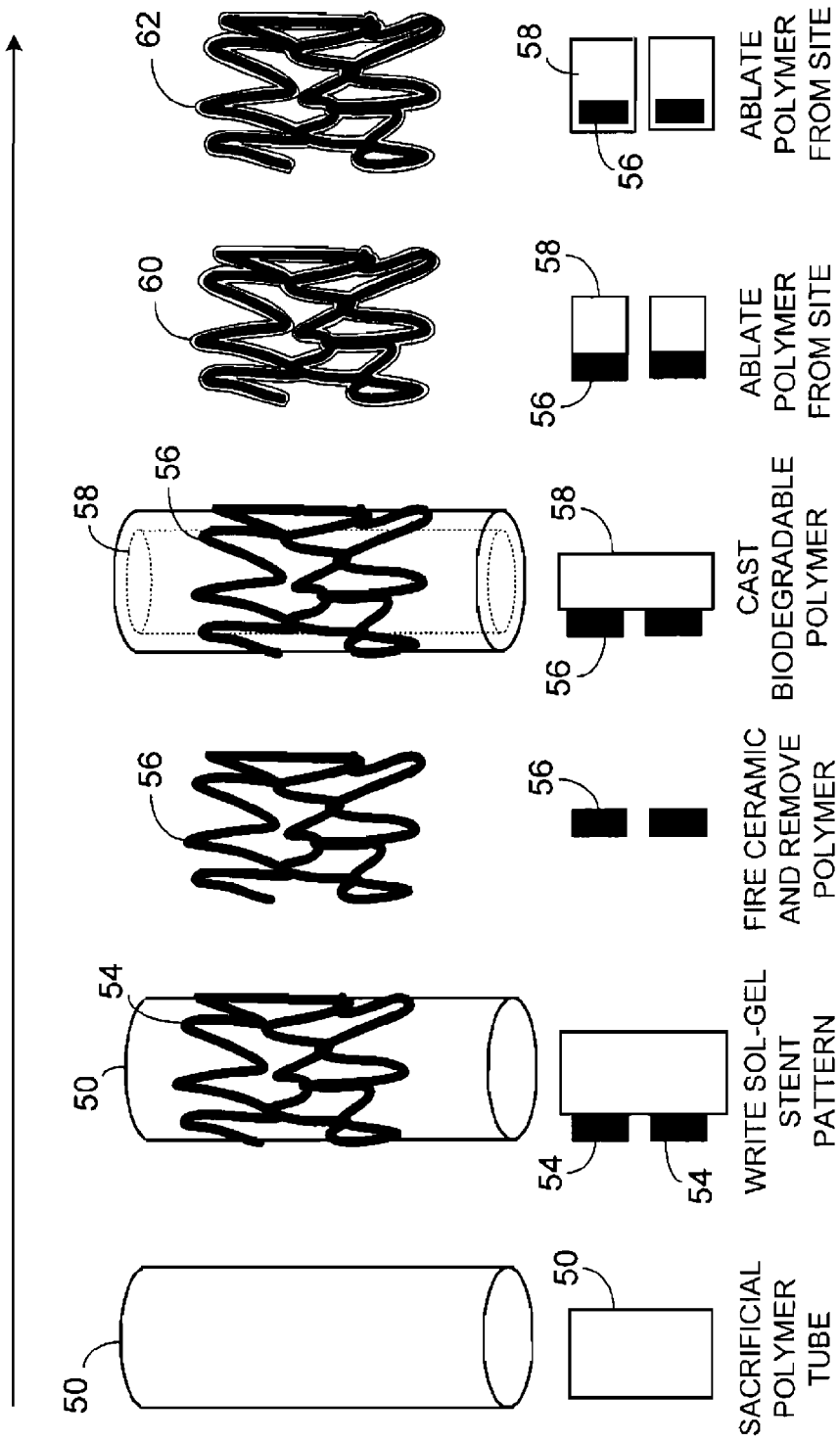

US 8,128,689 B2

BIOERODIBLE ENDOPROSTHESIS WITH BIOSTABLE INORGANIC LAYERS

CROSS-REFERENCE TO RELATED APPLICATIONS

This application claims priority under 35 USC §119(e) to U.S. Provisional Patent Application Ser. No. 60/845,135, filed on Sep. 15, 2006, the entire contents of which are hereby incorporated by reference.

TECHNICAL FIELD

This invention relates to medical devices, such as endoprostheses, and methods of making and using the same.

BACKGROUND

The body includes various passageways including blood vessels such as arteries, and other body lumens. These passageways sometimes become occluded or weakened. For example, they can be occluded by a tumor, restricted by plaque, or weakened by an aneurysm. When this occurs, the passageway can be reopened or reinforced, or even replaced, with a medical endoprosthesis. An endoprosthesis is an artificial implant that is typically placed in a passageway or lumen in the body. Many endoprostheses are tubular members, examples of which include stents, stent-grafts, and covered stents.

Many endoprostheses can be delivered inside the body by a catheter. Typically the catheter supports a reduced-size or compacted form of the endoprosthesis as it is transported to a desired site in the body, for example the site of weakening or occlusion in a body lumen. Upon reaching the desired site the endoprosthesis is installed so that it can contact the walls of the lumen.

One method of installation involves expanding the endoprosthesis. The expansion mechanism used to install the endoprosthesis may include forcing it to expand radially. For example, the expansion can be achieved with a catheter that carries a balloon in conjunction with a balloon-expandable endoprosthesis reduced in size relative to its final form in the body. The balloon is inflated to deform and/or expand the endoprosthesis in order to fix it at a predetermined position in contact with the lumen wall. The balloon can then be deflated, and the catheter withdrawn.

When the endoprosthesis is advanced through the body, its progress can be monitored, e.g., tracked, so that the endoprosthesis can be delivered properly to a target site. After the endoprosthesis is delivered to the target site, the endoprosthesis can be monitored to determine whether it has been placed properly and/or is functioning properly. Methods of tracking and monitoring a medical device include X-ray fluoroscopy and magnetic resonance imaging (MRI).

SUMMARY

In one aspect, the invention features an endoprosthesis, e.g., a stent, having a biostable layer and a bioerodible underlying structure, wherein the biostable layer is about 5% or less of the wall thickness.

In another aspect, the invention features a method of making an endoprosthesis, e.g., stent, having a biostable layer and an underlying structure.

In yet another aspect, the invention features a method that includes implanting an endoprosthesis, e.g., stent, having a biostable layer and an underlying structure in a body passageway to stimulate the attachment of endothelial cells to the stent or control the erosion rate of the underlying structure.

Embodiments may include one or more of the following features. The biostable layer of the endoprosthesis, e.g., stent, has one or more of the following characteristics: a thickness on average of about 10 to 20 nm; an average volume in the range of about 5,000 to 20,000 cubic micrometer per square millimeter of stent surface area; includes ceramic material; includes one or more metal oxides; includes one or more of titanium oxide, ruthenium oxide, or iridium oxide; includes a crystalline form of titanium oxide; includes a plurality of nodules about 15-20 nm in size; is on a surface of the stent, e.g., an interior surface, an exterior surface or a sidewall, of the stent; is covered, in full or in part, by a bioerodible layer; and/or is a monolayer. In embodiments, the bioerodible underlying structure includes one or more bioerodible materials chosen from one or more of a bioerodible metal, a bioerodible metal alloy or a bioerodible non-metal.

In embodiments, the endoprosthesis, e.g., stent, includes: one or more monolayers of a metal oxide, an organic material, a polymeric material or a biological material; and/or further includes at least one therapeutic agent, e.g., paclitaxel.

Further embodiments may include one or more of the following features. The biostable layer is formed by a sol-gel process. In embodiments, the process of making the biostable layer includes: modifying a selected portion of the surface of the underlying structure with hydroxyl groups; allowing the hydroxyl groups to react with one or more metal alkoxides to form a covalently-bound biostable layer of the one or more metal alkoxides; (optionally) removing excess adsorbed metal alkoxide; and hydrolyzing the covalently-bound surface of the biostable layer. In embodiments, the process of making endoprosthesis, e.g., stent, having a biostable layer and a bioerodible structure includes: applying the biostable layer on a surface of a substantially tubular polymer; exposing the biostable layer to temperature sufficiently elevated to remove the tubular polymer without substantially affecting the biostable layer; and applying a bioerodible polymer to the biostable layer. In embodiments, the process further includes applying a bioerodible polymer layer onto at least a portion of the biostable layer.

Further embodiments may include one or more of the following features: at least a portion of the stent degrades over a period of time inside the organism and releases the therapeutic agent; and/or the stent is implanted in a cardiovascular passageway.

An erodible or bioerodible medical device, e.g., a stent, refers to a device, or a portion thereof, that exhibits substantial mass or density reduction or chemical transformation, after it is introduced into a patient, e.g., a human patient. Mass reduction can occur by, e.g., dissolution of the material that forms the device and/or fragmenting of the device. Chemical transformation can include oxidation/reduction, hydrolysis, substitution, electrochemical reactions, addition reactions, or other chemical reactions of the material from which the device, or a portion thereof, is made. The erosion can be the result of a chemical and/or biological interaction of the device with the body environment, e.g., the body itself or body fluids, into which it is implanted and/or erosion can be triggered by applying a triggering influence, such as a chemical reactant or energy to the device, e.g., to increase a reaction rate. For example, a device, or a portion thereof, can be formed from an active metal, e.g., Mg or Ca or an alloy thereof, and which can erode by reaction with water, producing the corresponding metal oxide and hydrogen gas (a redox reaction). For example, a device, or a portion thereof, can be formed from an erodible or bioerodible polymer, or an alloy or blend erodible or bioerodible polymers which can erode by hydrolysis with water. The erosion occurs to a desirable extent in a time frame that can provide a therapeutic benefit. For example, in embodiments, the device exhibits substantial mass reduction after a period of time which a function of the device, such as support of the lumen wall or drug delivery is no longer needed or desirable. In particular embodiments, the device exhibits a mass reduction of about 10 percent or more, e.g. about 50 percent or more, after a period of implantation of one day or more, e.g. about 60 days or more, about 180 days or more, about 600 days or more, or 1000 days or less. In embodiments, the device exhibits fragmentation by erosion processes. The fragmentation occurs as, e.g., some regions of the device erode more rapidly than other regions. The faster eroding regions become weakened by more quickly eroding through the body of the endoprosthesis and fragment from the slower eroding regions. The faster eroding and slower eroding regions may be random or predefined. For example, faster eroding regions may be predefined by treating the regions to enhance chemical reactivity of the regions. Alternatively, regions may be treated to reduce erosion rates, e.g., by using coatings. In embodiments, only portions of the device exhibits erodibilty. For example, an exterior layer or coating may be erodible, while an interior layer or body is non-erodible. In embodiments, the endoprosthesis is formed from an erodible material dispersed within a non-erodible material such that after erosion, the device has increased porosity by erosion of the erodible material.

Erosion rates can be measured with a test device suspended in a stream of Ringer's solution flowing at a rate of 0.2 m/second. During testing, all surfaces of the test device can be exposed to the stream. For the purposes of this disclosure, Ringer's solution is a solution of recently boiled distilled water containing 8.6 gram sodium chloride, 0.3 gram potassium chloride, and 0.33 gram calcium chloride per liter.

Aspects and/or embodiments may have one or more of the following additional advantages. The presence of a biostable layer in a bioerodible medical device offers several advantages including one or more of: providing a firm substrate to an otherwise eroding structure, thus facilitating endothelial cell growth and/or attachment while retaining sufficient flexibility to facilitate stent delivery and deployment; providing a biostable layer that offers increased flexibility for tailoring a stent surface (e.g., tailoring one or more of: texture, thickness, functional group attachment and/or formation of molecule-sized cavities upon removal of organic templates or "molecular imprinting"); and/or controlling erosion (e.g., bioerosion) of the endoprosthesis by protecting the underlying structure from corrosion. By placing one or more biostable layers at predetermined locations, the rate of erosion of different portions of the endoprosthesis can be controlled. Release of a therapeutic agent from the endoprosthesis can be controlled as the rate of erosion is controlled. Moreover, the visibility of the endoprosthesis, e.g., biodegradable endoprosthesis, to imaging methods, e.g., X-ray and/or Magnetic Resonance Imaging (MRI), can be enhanced, even after the endoprosthesis is partly eroded, by e.g., incorporating a radiopaque material into the biostable layer.

Other aspects, features, and advantages will be apparent from the description and drawings, and from the claims.

DESCRIPTION OF DRAWINGS

FIGS. 7A-7F are perspective and cross-sectional views of a process for making the stent having a biostable and a bioerodible underlying structure.

Like reference symbols in the various drawings indicate like elements.

DETAILED DESCRIPTION

Figure 1A:
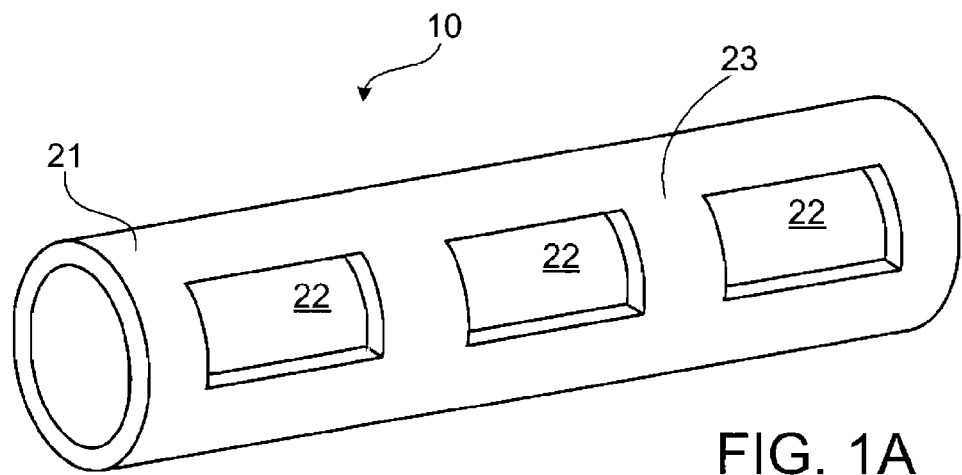
FIGS. 1A-1B are a perspective view and a cross-sectional view through the stent wall, respectively, of a stent.
Figure 1B:
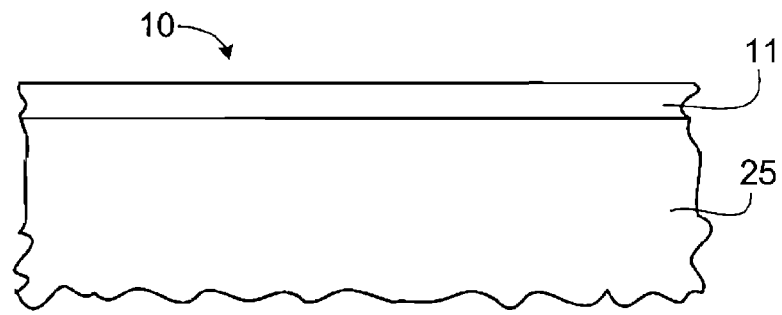
Figure 2A:
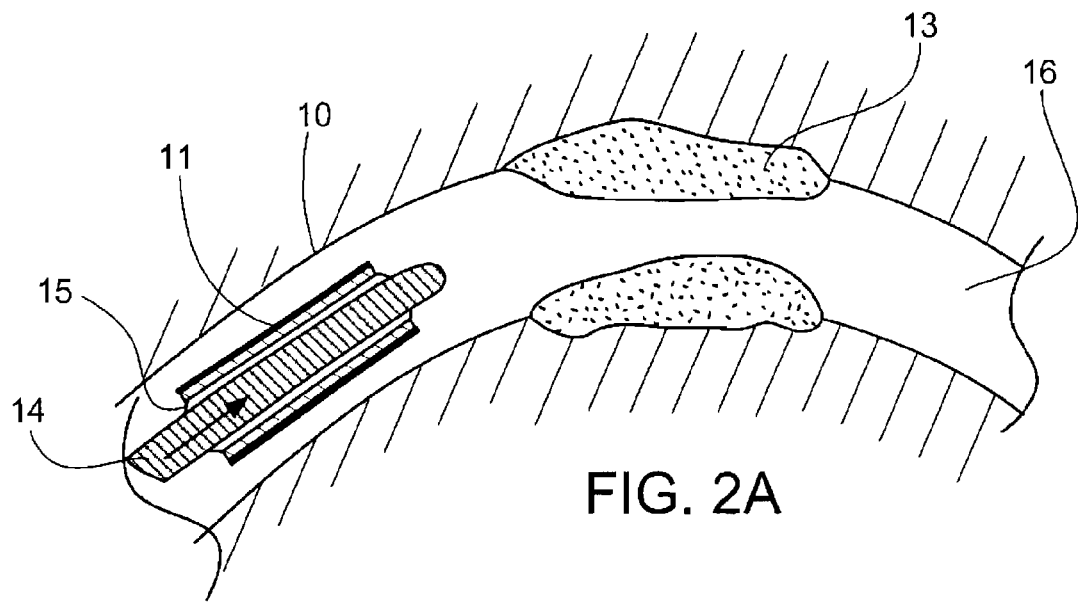
FIGS. 2A-2D are longitudinal cross-sectional views, illustrating delivery of a stent in a collapsed state (FIG. 2A), expansion of the stent (FIG. 2B), deployment of the stent (FIG. 2C), and degradation of the stent (FIG. 2D).
Figure 2B:
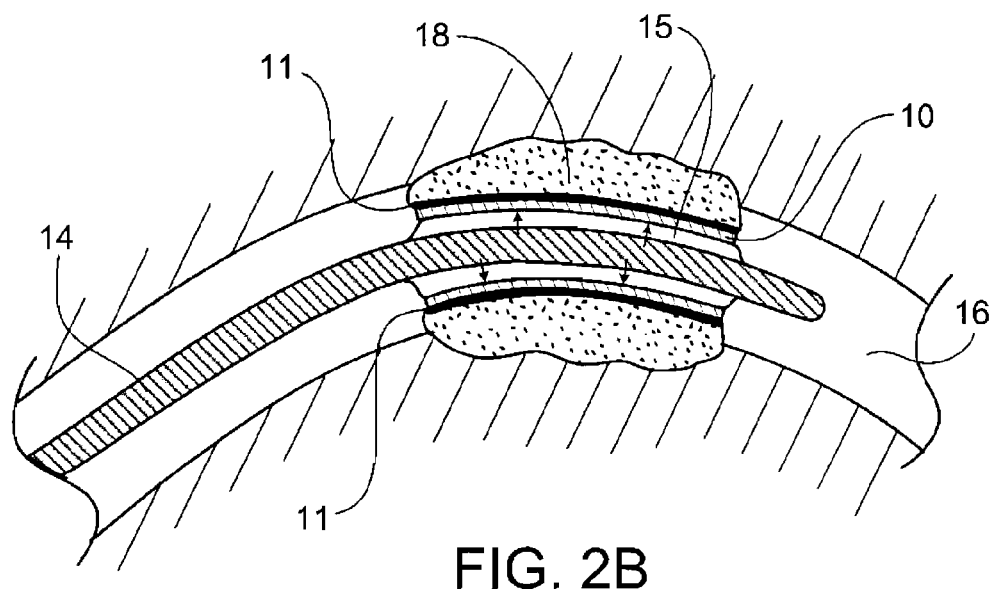
Figure 2C:
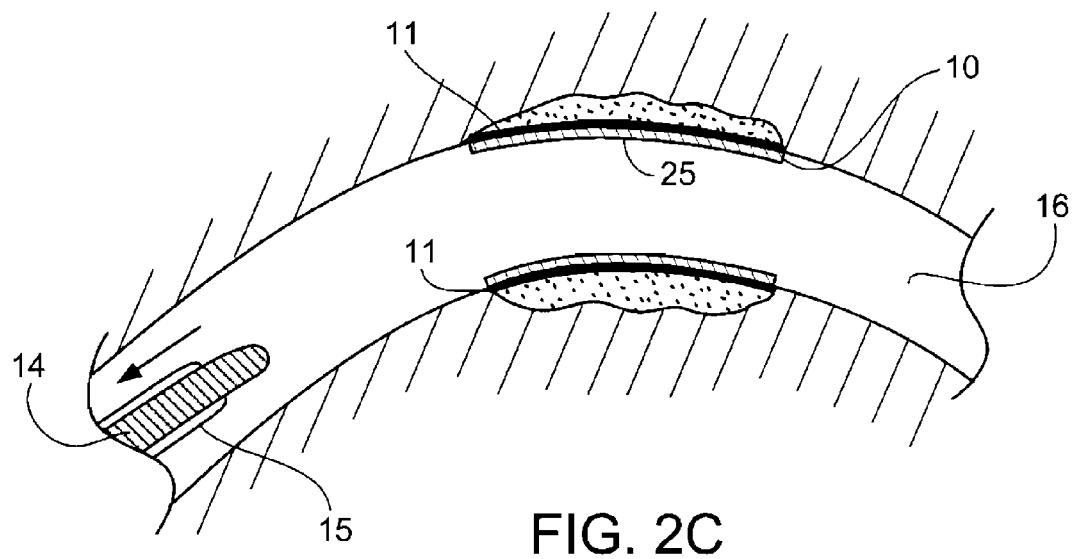
Figure 2D:
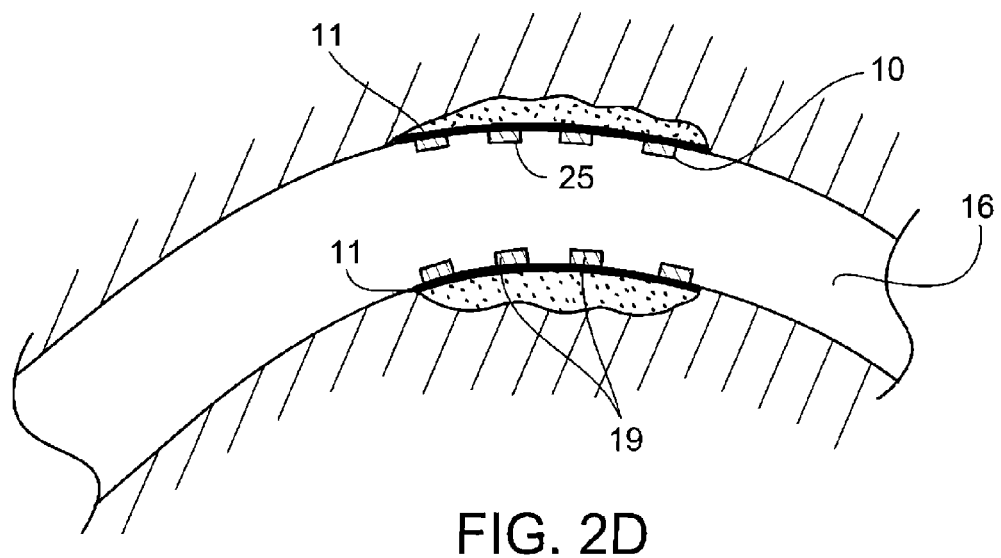

Referring to FIGS. 1A-1B, the stent 10 is generally a tubular device defined by a stent wall 21 including fenestrations 22 separated by struts 23. Referring as well to FIG. 1B, a cross-section through the stent wall, a thin continuous biostable layer 11 is provided on the outside of an erodible layer 25. In this embodiment, the bioerodible layer is eroded by exposure to bodily fluid from the interior of the stent, while the biostable layer provides a firm structure to enhance endothelization and reduce dislodgement of fragments of the bioerodible layer. Referring to FIGS. 2A-2D, in use, stent 10 is placed over a balloon 15 carried near the distal end of a catheter 14, and is directed through a lumen 16 (FIG. 2A) until the portion carrying the balloon and stent reaches the region of an occlusion 18. The stent 10 is then radially expanded by inflating the balloon 15 and pressed against the vessel wall with the result that occlusion 18 is compressed (FIG. 2B). The vessel wall surrounding the stent 10 undergoes a radial expansion (FIG. 2B). The pressure is then released from the balloon 15, and the catheter 14 is withdrawn from the vessel (FIG. 2C). Over time, the underlying structure 25 of the stent 10 erodes in the body, sometimes creating fragments 19. The biostable layer 11 remains leaving a firm structure for endothelization from the lumen wall which envelopes the stent and, to some extent, reducing erosion and/or dislodgement of the fragments (FIG. 2D).

Figure 3A:
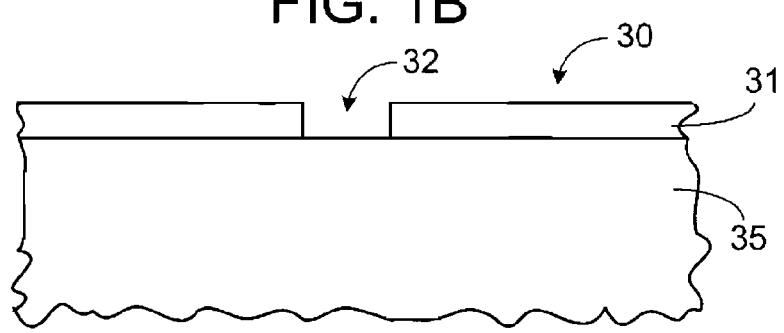
FIGS. 3A-3B are cross-sectional views of a stent wall before and after erosion of an erodible layer, respectively.
Figure 3B:
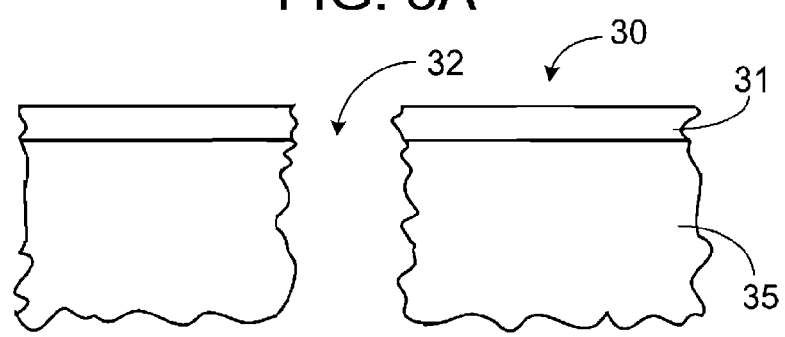

Referring to FIGS. 3A and 3B, in another embodiment, stent 30 having a non-continuous biostable layer 31 on top of a bioerodible underlying structure 35 is illustrated before and after exposure to external fluids, respectively. The non-continuous layer 31 defines a window 32 through which the bioerodible structure is exposed to the body from the exterior of the stent. Prior to exposure to the bodily fluids, the bioerodible underlying structure 35 is substantially intact (FIG. 3A). Over time, portion(s) of the underlying structure 35 exposed to external fluids erode at a faster rate than the corresponding areas covered by the biostable layer 31, thus creating a differentially fragmented stent structure (FIG. 3B).

The underlying stent structure can include one or more bioerodible materials chosen from, e.g., a bioerodible metal, a bioerodible metal alloy, or a bioerodible non-metal. In particular embodiments, the stent structure has an overall thickness, stiffness and other mechanical properties sufficient to maintain the patency of the occluded region of a lumen after an angioplasty procedure. As the erodible structure degrades over time, the wall thickness is reduced and the flexibility of the stent is increased. Endothelization of the erodible structure may be typically inhibited by the continuous erosion. The biostable layer provides a non-eroding surface on which cell growth can occur. The biostable layer is sufficiently flexible, e.g., because of its thinness, so that it does not substantially inhibit the mechanical properties of the stent needed for delivery and deployment or inhibit the natural motion of the blood vessel. The biostable layer can also be textured to enhance endothelization. The biostable layer can be provided, and textured morphologies can be formed, by low temperature processes, such as sol-gel processes.

In particular embodiments, the biostable material is a ceramic and the bioerodible material is a polymer. The biostable layer typically makes up about 50%, 20%, 10% or less of the wall thickness of the stent at implantation, e.g., about 5%, 1%, 0.5%, or 0.05% or less of the wall thickness of the stent at implantation. Typically, the relative thinness of the biostable layer is adjusted such that the stent retains the flexibility needed for stent delivery and deployment. The stent typically retains at least about 50%, 75%, 90% or more of the flexibility of a stent otherwise identical but without the biostable layer. The flexibility of the stent can be measured by techniques known in the art. For example, the stent can be expanded into a silicon rubber test tube with similar mechanical properties as a blood vessel. After expansion, the change in flexibility of the stented vessel area can be measured by bending the vessel in a three-point bend test. The three-point bend test is known in the art as a way of evaluating stent stiffness (or its reciprocal, flexibility). It typically involves determining the slope of a force-displacement curve by measuring the stent deflection when the sent is secured by two end-points at a predetermined distance apart, e.g., 20 mm apart, and applying a vertical force or traction midway between the two secured end-points (e.g., applying a force to a hook suspended by an Instron), which provides the third point of the three-point bend test. The three-point bend test is described further in Ormiston, J. et al. (2000) *Catherization and Cardiovascular Interventions* 50:120-124. Alternatively, the bending of the stent on the balloon catheter can be measured, e.g., by performing a track test. Track testing is known in the art, and is described, for example, in paragraphs 47-53 of U.S. 2004-0210211.

Examples of ceramics include metal oxides, e.g., oxides that include one or more of titanium oxide, ruthenium oxide or iridium oxide. For example, one or more layers of titanium oxide can be used because of its good biocompatibility and induction of endothelization. Titanium oxide can be used in crystalline or amorphous form. Crystalline forms can enhance attachment and/or growth of endothelial cells. Titanium oxides are discussed further in Chen, J. Y., Wan, G. J. (2004) *Surface & Coating Technology* 186:270-276. The thickness of the biostable layer can vary as needed, but is typically substantially thin to provide a flexible stent structure to facilitate, e.g., stent deployment, while providing a substantially firm substrate to facilitate endothelization. Typically, the biostable layer 11 has a thickness in the range of less than 1000 nm, typically less than 100 nm microns, and about 1 to 50 nm, more typically, about 10 to 20 nm. The biostable layer can have a volume an average volume in the range of about 2,000 to 30,000, more typically 5,000 to 20,000 cubic micrometer per square millimeter of stent surface area. The volume can be measured, e.g., indirectly by statistically making a line measurement along the stent surface using, for example, atomic force microscopy (AFM), or focused ion beam to produce cross-sections along lines. Alternatively, field emission scanning electron microscopy (FSEM) can be used to examine the surface topology and/or the percentage of the stent surface that is covered with the biostable layer. The biostable layer 11 can extend over an entire surface of the stent 10 (e.g., an inner or outer surface, or a side wall, or any combination thereof), or can cover a portion of the stent (e.g., 25%, 50%, 75% of the length of the stent surface).

The biostable layer can coat one or more of the interior or exterior stent surfaces and/or sidewalls, leaving the abluminal surface exposed. In embodiments, the interior surface is coated. Selected portions of the biostable layer can be removed as desired using, for example, a laser to control the rate and/or location of erosion. The stent can have one, two or more layers of biostable materials as desired. In other embodiments, one or more layers of biostable materials can be embedded with one or more bioerodible materials (e.g., organic, polymeric, biological or metallic materials), thus forming a multi-layered hybrid structure.

Figure 4A:
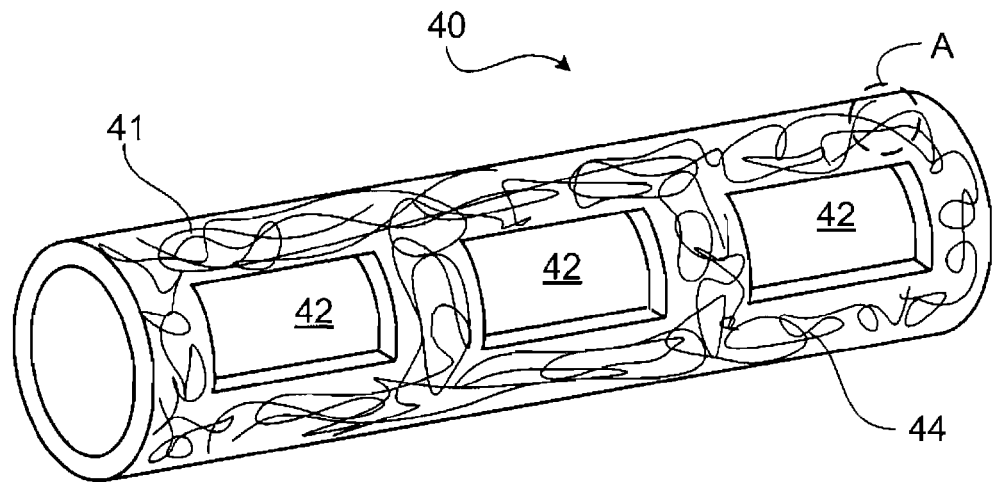
FIGS. 4A-4B are a perspective view and a cross-sectional view, respectively, of a textured stent.
Figure 4B:
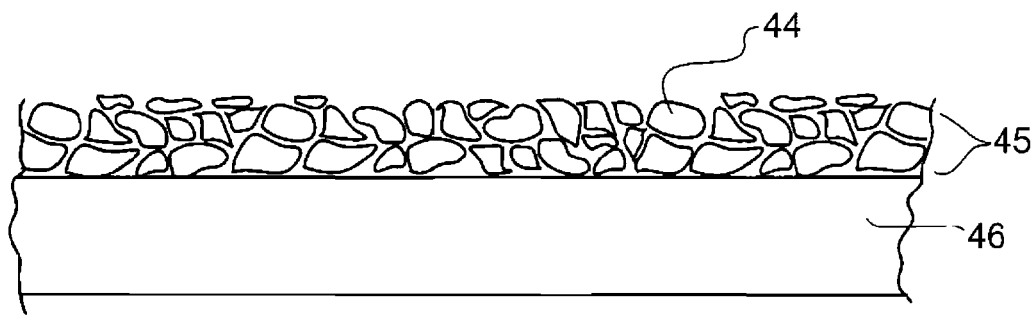
Figure 5:
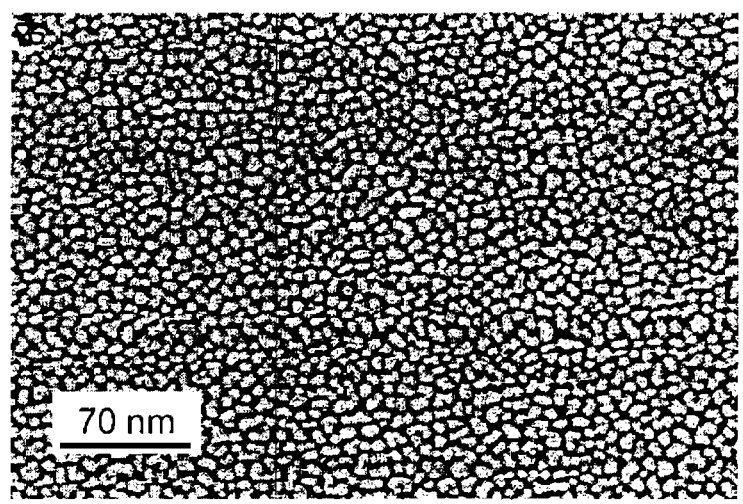
FIG. 5 is a scanning electron microscopy (SEM) micrograph of an exemplary textured stent.

The biostable layer offers additional advantages, such as allowing tailoring of the stent surface (e.g., tailoring of one or more of: texture, thickness, functional group attachment and/or molecular imprinting by forming molecule-sized cavities upon removal of organic templates). Referring to FIGS. 4A-4B, a perspective view of a stent 40 having a textured surface 41, and a cross-sectional view of the region A in FIG. 4A, respectively, the biostable layer 45 can have a texture (also referred to herein as "nanotexture") characterized by a plurality of nodules 44 that facilitates endothelial cell migration and/or attachment. Referring to FIG. 5, a scanning electron microscopy (SEM) micrograph of an exemplary high magnification top view of a textured surface titania layer shows a spherical grain morphology of a plurality of nodules about 15-20 nm in size (scale bar in FIG. 5 corresponds to about 70 nm). Surface morphologies of ceramic layers are described further in Daoud, W. et al. (2005) *Journal of Non-Crystalline Solids* 351:1486-1490. The nodule diameter is typically less than 100 nm, e.g., less than 50 nm, typically about 5 to 30 nm, more typically about 10 to 20 nm. The texture defines spaces between the nodules of about 50 to 500 nm, e.g., around 200 nm, or about the size of a typical endothelial cell. Textured coatings enhance growth and migration of both smooth muscle and endothelial cells. In order to reduce smooth muscle coverage, the textured biostable layer can include a drug that preferentially inhibits smooth muscle cell growth, e.g., paclitaxel, thereby maximizing endothelial cell coverage of the stent.

The biostable layer can be formed by sol-gel processes. Sol-gel processes, in particular, low temperature sol-gel process, are useful for creating a crystalline metal oxide coating on a polymeric substrate (Daoud, W. et al. (2005) supra; Yun, Y-J et al. (2004) *Materials Letters* 58:3703-3706; Nishio, K. et al. (1999) *Thin Solid Films* 350:96-100; Wu, L. et al. (2005) *Journal of Solid State Chemistry* 178:321-328). In embodiments, the metal oxide is applied to the polymer. In other embodiments, the polymer is applied to the metal oxide. Sol gel processes can form thin coatings, without excessive heating which could destroy the polymer or other substrates. For example, crystalline titanium dioxide ($TiO_2$) thin films can be deposited onto an erodible stent at low temperatures using a sol-gel dip-coating method. The titania sol can be prepared, for example, at room temperature by mixing titanium tetraisopropoxide (TTIP) in acidic aqueous solutions and subsequently refluxed at 80° C. for 8 hours to facilitate the formation of anatase crystallites. The deposited titanium oxide films can be heated at 115° C. Homogeneous surfaces of spheroids typically about 20-60 nm in size can be formed. One or more biostable layers of iridium oxide can be prepared by, e.g., a sol-gel dip-coating process where iridium chloride is used as the starting material. The coating solution can also be prepared by reacting iridium chloride, ethanol and acetic acid as described in Nishio, K. et al. (1999) supra. Sol-solvothermal processes can be used to form mesoporous nanocrystalline titanium dioxide with photocatlytic activity as described in Wu et al. (2005) supra. In embodiments, the deposition of the biostable layers is carried out at room temperature.

A surface sol-gel process involving a layer-by-layer approach can be used to add one or more monolayers of metal oxides, organic, polymeric, and/or biological materials (e.g., peptides such as RGD peptides to promote endothelial cell binding) (see e.g., Kunitake, T., Lee, S-W. (2004) *Analytica Chimica Acta* 504:1-6).

Figure 6:
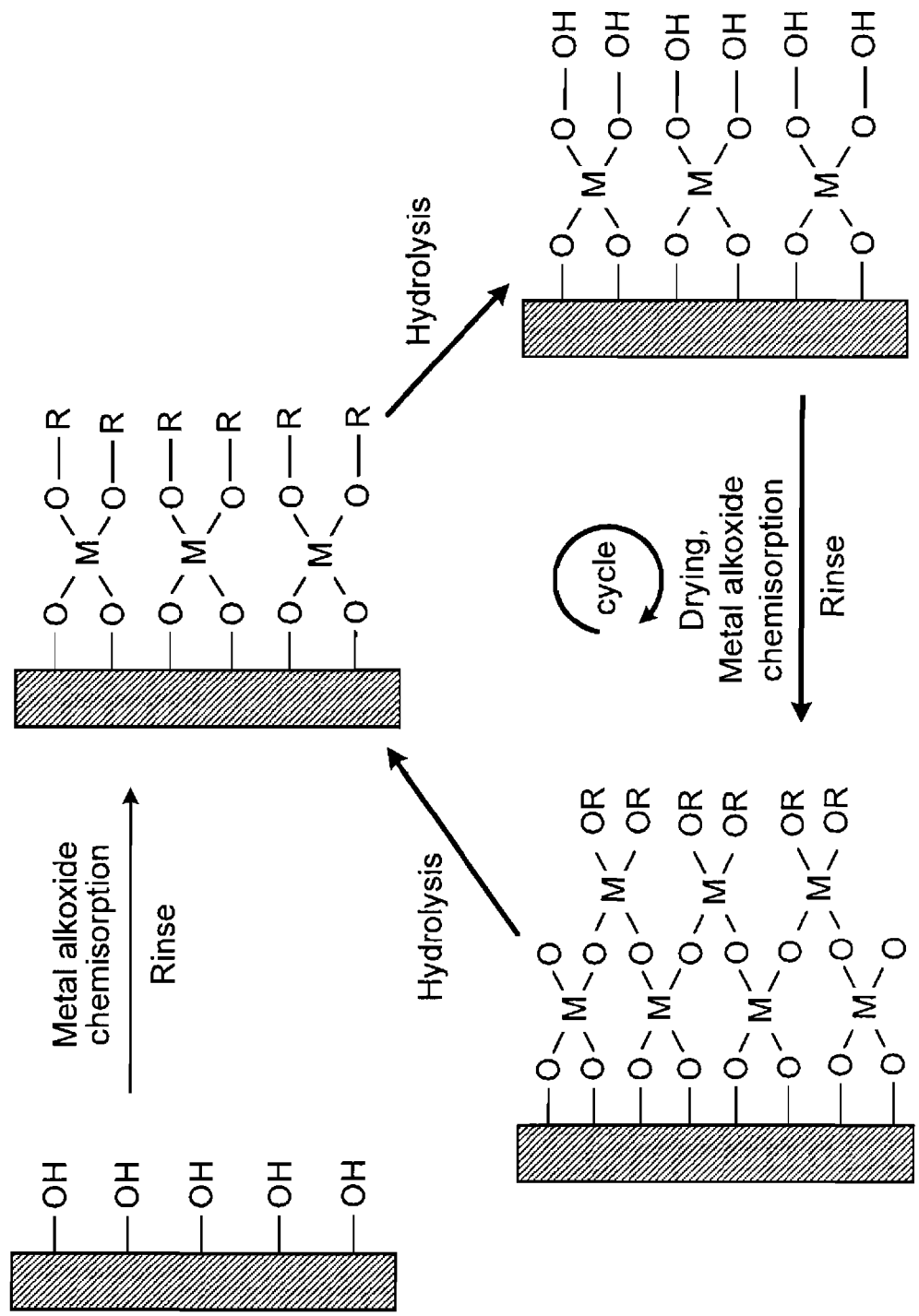
FIG. 6 is a general scheme of the surface sol-gel process.

Referring to FIG. 6, a general scheme of surface sol-gel process shows a solid substrate with hydroxyl groups on its surface, which is allowed to react with metal alkoxides in solution to form a covalently-bound surface monolayer of the metal alkoxide. The excessively adsorbed alkoxide can be removed by rinsing. The chemisorbed alkoxide monolayer is then hydrolyzed to give a new hydroxylated surface. The thickness of the metal oxide layer can be as thin as about 1 nm. In embodiments, the polyhydroxyl compounds adsorbed on the surface provide free hydroxyl groups, and metal alkoxides are subsequently adsorbed. The process can be repeated as desired to form one or more multilayers of the same or different materials, e.g., other metal oxides, organic materials (e.g., functional groups), polymeric materials, and/or biological materials (e.g., peptides). The biostable layer can be derivatized as desired by altering the compositions of the layers, thus creating functionalized groups and/or selective molecular imprinting sites. For example, organic polyhydroxyl compounds (e.g., carboxylic acids) can be readily incorporated onto a surface of a metal oxide layer. Upon removal of the organic template, molecule-sized cavities are formed imprinting a cavity that reflects the structural and enantioselective features of the template. The biostable layer can be derivatized further, e.g., to include biodegradable polymers to create surface features that enhance endothelial cell function. For example, biodegradable polymers, such as polylactic acid and/or polyglycolic acid (e.g., poly(lactic-co-glycolic acid) (PLGA)) can be used as scaffolds to support endothelial cell attachment. Suitable techniques are described in Miller, D. C. et al. (2004) *Biomaterials* 25:53-61. Since the attachment of both smooth muscle and endothelial cells is typically increased using PLGA, the polymer may optionally include an inhibitor of smooth muscle cells, such as paclitaxel.

The biostable layer can be applied to the stent before or after adding the bioerodible structure. For example, the biostable layer can be applied to the stent prior to forming the bioerodible structure. In those embodiments, the biostable layer(s) (e.g., ceramic layer) can be exposed to high temperatures before it is connected to the bioerodible structure.

Referring to FIGS. 7A-7F, perspective and cross-sectional views of the stent undergoing coating steps 7A-7E (upper and lower panels, respectively), starting from step 7A, a solid polymer of tubular shape 50 (e.g., a tube made of nylon, poly(ethylene oxide), polyimine (PI)) having a substantially smooth surface is shown. Referring to FIG. 7B, a stent pattern 54 can be formed on the polymer tube 50, e.g., by writing the stent shape on the polymer tube 50 using an ink pen containing a thick sol-gel solution. In other embodiments, a metallic solution can be used to write a metallic layer on the polymer tube. Ink pens are commercially available from Ohm Craft, Honeoye Falls, N.Y. under the registered mark MicroPen®. Referring back to FIG. 7B and FIG. 7C, by applying heating conditions according to ceramic specifications, a titanium oxide coating is converted into an anatase state (e.g., by heating the polymer to about 500° C. for about 6 hours) and the polymer tube is eliminated, thereby resulting in a very thin biostable (e.g., ceramic) film 56 in the shape of the stent. The biostable film 56 can then be fitted inside a cylindrical tube (not shown) with an inner diameter the size of the desired inner diameter of the final stent and an outer diameter slightly larger than the biostable (e.g., ceramic) film 56. Referring to FIG. 7D, a bioerodible polymer is deposited within the cylindrical tube, resulting in a bioerodible tube 58 with a biostable (e.g., ceramic) layer 56 having a stent shape embedded within. Portions of the bioerodible tube 58 can be selectively removed, e.g., using an excimer laser to ablate the polymer, thereby forming a coated ceramic film 60 (i.e., a ceramic film 56 coated with a biodegradable layer 58). Referring back to FIG. 7D, the removal can be done, for example, by aiming the laser radially to the bioerodible tube 58 and focusing the laser in a number steps to the whole cylinder at a fluence level which is high enough to ablate the polymer, but lower than the ablation threshold of the biostable, e.g., ceramic, film 56. The biodegradable polymer 58 adjacent to the biostable, e.g., ceramic, film 56 will remain substantially intact as it is in the shadow of the biostable, e.g., ceramic, film. Referring to FIG. 7E, the polymer in between can be ablated, thus resulting in a stent 60 made of a biodegradable polymer 58 with a biostable, e.g., ceramic, outer film 56. Referring to FIG. 7F, further embodiments (optionally) include applying (e.g., spraying) to the stent 60 of FIG. 7E, one or more layers of a bioerodible polymer (e.g., the same or different bioerodible polymer as the one used to form the bioerodible tube 58), such that the biostable (e.g., ceramic) film 56 is embedded (fully or a portion thereof) within a thin bioerodible polymeric film 58. In the embodiment shown in FIG. 7F, the same bioerodible polymer is applied to the stent 60 as the one used in FIGS. 7D-7E. The bioerodible polymer is expected to degrade in the body at a fast rate, however it is expected to reduce the propensity of the biostable ceramic layer to break off after expansion.

Referring back to FIG. 7A-7F, the biostable, e.g., ceramic, layer can be further altered to enhance the bond between the bioerodible and the biostable layers. In embodiments, a plurality of indentations or markings can be formed on stent pattern 54, using, for example, an excimer laser. Such indentations or markings will create pitts on the inside of the ceramic shape once the firing has taken place, thus enhancing the bond between the biodegradable polymer and the biostable, e.g., ceramic, layer.

In embodiments, the biostable layer can be used for corrosion protection when the bioerodible underlying structure of the stent is a bioerodible metal, such as magnesium, iron, and nickel (Cheng, F. T. et al. (2004) *Scripta Materilia* 51:1041-1045; Atik, M. et al. (1995) *Ceramics International* 21:403-406). Other coatings that can be used to form thin layers by sol-gel for corrosion protection include zirconium dioxide ($ZrO_2$), binary compositions of titanium dioxide and silicon dioxide ($TiO_2$—$SiO_2$), and aluminium oxide and silicon dioxide ($Al_2O_3$—$SiO_2$) (Atik, M. et al. (1995) supra).

The stent may additionally include one or more biostable materials in addition to one or more biostable layer described above. Examples of biostable materials include stainless steel, tantalum, niobium, platinum, nickel-chrome, cobalt-chromium alloys such as Elgiloy® and Phynox®, Nitinol (e.g., 55% nickel, 45% titanium), and other alloys based on titanium, including nickel titanium alloys, thermo-memory alloy materials. Stents including biostable and bioerodible regions are described, for example, in US 2006-0122694, entitled "Medical Devices and Methods of Making the Same." The material can be suitable for use in, for example, a balloon-expandable stent, a self-expandable stent, or a combination of both (see e.g., U.S. Pat. No. 5,366,504). The components of the medical device can be manufactured, or can be obtained commercially. Methods of making medical devices such as stents are described in, for example, U.S. Pat. No. 5,780,807, and U.S. Patent Application Publication No. 2004-0000046-A1, both of which are incorporated herein by reference. Stents are also available, for example, from Boston Scientific Corporation, Natick, Mass., USA, and Maple Grove, Minn., USA.

Bioerodible materials are described, for example, in U.S. Pat. No. 6,287,332 to Bolz; U.S. Patent Application Publication No. US 2002/0004060 A1 to Heublein; U.S. Pat. Nos. 5,587,507 and 6,475,477 to Kohn et al., the entire contents of each of which is hereby incorporated by reference. Examples of bioerodible metals include alkali metals, alkaline earth metals (e.g., magnesium), iron, zinc, and aluminum. Examples of bioerodible metal alloys include alkali metal alloys, alkaline earth metal alloys (e.g., magnesium alloys), iron alloys (e.g., alloys including iron and up to seven percent carbon), zinc alloys, and aluminum alloys. Examples of bioerodible non-metals include bioerodible polymers, such as, e.g., polyanhydrides, polyorthoesters, polylactides, polyglycolides, polysiloxanes, cellulose derivatives and blends or copolymers of any of these. Bioerodible polymers are disclosed in U.S. Published Patent Application No. 2005/0010275, filed Oct. 10, 2003; U.S. Published Patent Application No. 2005/0216074, filed Oct. 5, 2004; and U.S. Pat. No. 6,720,402, the entire contents of each of which is incorporated by reference herein.

The stent can be manufactured, or the starting stent can be obtained commercially. Methods of making stents are described, for example, in U.S. Pat. No. 5,780,807 and U.S. Application Publication US-2004-0000046-A1. Stents are also available, for example, from Boston Scientific Corporation, Natick, Mass., USA, and Maple Grove, Minn., USA. The stent can be formed of any biocompatible material, e.g., a metal or an alloy, as described herein. The biocompatible material can be suitable for use in a self-expandable stent, a balloon-expandable stent, or both. Examples of other materials that can be used for a balloon-expandable stent include noble metals, radiopaque materials, stainless steel, and alloys including stainless steel and one or more radiopaque materials.

The endoprosthesis, e.g., the stent, can, further include at least one therapeutic agent present in the biostable and/or bioerodible portion of the stent. If the therapeutic agent is found in the bioerodible portion of the stent (e.g., interspersed throughout or localized to a predetermined site), release of the therapeutic agent can be controlled as the bioerodible portion of the stent erodes. The terms "therapeutic agent", "pharmaceutically active agent", "pharmaceutically active material", "pharmaceutically active ingredient", "drug" and other related terms may be used interchangeably herein and include, but are not limited to, small organic molecules, peptides, oligopeptides, proteins, nucleic acids, oligonucleotides, genetic therapeutic agents, non-genetic therapeutic agents, vectors for delivery of genetic therapeutic agents, cells, and therapeutic agents identified as candidates for vascular treatment regimens, for example, as agents that reduce or inhibit restenosis. By small organic molecule is meant an organic molecule having 50 or fewer carbon atoms, and fewer than 100 non-hydrogen atoms in total.

The therapeutic agent can be chosen from one or more of, e.g., an anti-thrombogenic agent, an anti-proliferative/anti-mitotic agents, an inhibitor of smooth muscle cell proliferation, an antioxidant, an anti-inflammatory agent, an anesthetic agents, an anti-coagulant, an antibiotic, or an agent that stimulates endothelial cell growth and/or attachment. Exemplary therapeutic agents include, e.g., anti-thrombogenic agents (e.g., heparin); anti-proliferative/anti-mitotic agents (e.g., paclitaxel, 5-fluorouracil, cisplatin, vinblastine, vincristine, inhibitors of smooth muscle cell proliferation (e.g., monoclonal antibodies), and thymidine kinase inhibitors); antioxidants; anti-inflammatory agents (e.g., dexamethasone, prednisolone, corticosterone); anesthetic agents (e.g., lidocaine, bupivacaine and ropivacaine); anti-coagulants; antibiotics (e.g., erythromycin, triclosan, cephalosporins, and aminoglycosides); agents that stimulate endothelial cell growth and/or attachment. Therapeutic agents can be non-ionic, or they can be anionic and/or cationic in nature. Therapeutic agents can be used singularly, or in combination. Preferred therapeutic agents include inhibitors of restenosis (e.g., paclitaxel), anti-proliferative agents (e.g., cisplatin), and antibiotics (e.g., erythromycin). Additional examples of therapeutic agents are described in U.S. Published Patent Application No. 2005/0216074, the entire disclosure of which is hereby incorporated by reference herein.

To enhance the radiopacity of stent, a radiopaque material, such as gold nanoparticles, can be incorporated into endoprosthesis, e.g., the biostable layer or the stent body. For example, gold nanoparticles can be made positively charged by applying a outer layer of lysine to the nanoparticles, e.g., as described in "DNA Mediated Electrostatic Assembly of Gold Nanoparticles into Linear Arrays by a Simple Dropcoating Procedure" Murali Sastrya and Ashavani Kumar, *Applied Physics Letters*, Vol. 78, No. 19, 7 May 2001. Other radiopaque materials include, for example, tantalum, platinum, palladium, tungsten, iridium, and their alloys.

Medical devices, in particular endoprostheses, as described above include implantable or insertable medical devices, including catheters (for example, urinary catheters or vascular catheters such as balloon catheters), guide wires, balloons, filters (e.g., vena cava filters), stents of any desired shape and size (including coronary vascular stents, aortic stents, cerebral stents, urology stents such as urethral stents and ureteral stents, biliary stents, tracheal stents, gastrointestinal stents, peripheral vascular stents, neurology stents and esophageal stents), grafts such as stent grafts and vascular grafts, cerebral aneurysm filler coils (including GDC—Guglilmi detachable coils—and metal coils), filters, myocardial plugs, patches, pacemakers and pacemaker leads, heart valves, and biopsy devices. In one embodiment, the medical device includes a catheter having an expandable member, e.g., an inflatable balloon, at its distal end, and a stent or other endoprosthesis (e.g., an endoprosthesis or stent as described herein). The stent is typically an apertured tubular member (e.g., a substantially cylindrical uniform structure or a mesh) that can be assembled about the balloon. The stent typically has an initial diameter for delivery into the body that can be expanded to a larger diameter by inflating the balloon. The medical devices may further include drug delivery medical devices for systemic treatment, or for treatment of any mammalian tissue or organ.

The medical device, e.g., endoprosthesis, can be generally tubular in shape and can be a part of a stent. Simple tubular structures having a single tube, or with complex structures, such as branched tubular structures, can be used. Depending on specific application, stents can have a diameter of between, for example, 1 mm and 46 mm. In certain embodiments, a coronary stent can have an expanded diameter of from about 2 mm to about 6 mm. In some embodiments, a peripheral stent can have an expanded diameter of from about 4 mm to about 24 mm. In certain embodiments, a gastrointestinal and/or urology stent can have an expanded diameter of from about 6 mm to about 30 mm. In some embodiments, a neurology stent can have an expanded diameter of from about 1 mm to about 12 mm. An abdominal aortic aneurysm (AAA) stent and a thoracic aortic aneurysm (TAA) stent can have a diameter from about 20 mm to about 46 mm. Stents can also be preferably bioerodible, such; as a bioerodible abdominal aortic aneurysm (AAA) stent, or a bioerodible vessel graft.

In some embodiments, the medical device, e.g., endoprosthesis, is used to temporarily treat a subject without permanently remaining in the body of the subject. For example, in some embodiments, the medical device can be used for a certain period of time (e.g., to support a lumen of a subject), and then can disintegrate after that period of time. Subjects can be mammalian subjects, such as human subjects (e.g., an adult or a child). Non-limiting examples of tissues and organs for treatment include the heart, coronary or peripheral vascular system, lungs, trachea, esophagus, brain, liver, kidney, bladder, urethra and ureters, eye, intestines, stomach, colon, pancreas, ovary, prostate, gastrointestinal tract, biliary tract, urinary tract, skeletal muscle, smooth muscle, breast, cartilage, and bone.

All publications, patent applications, patents, and other references mentioned herein are incorporated by reference herein in their entirety.

Other embodiments are within the scope of the following claims.

What is claimed is:

1. A stent comprising a biostable layer and a bioerodible underlying structure, wherein the biostable layer is about 5% or less of a wall thickness of a strut of the stent, wherein the bioerodible underlying structure comprises a bioerodible metal.

2. The stent of claim 1, wherein the biostable layer has a thickness on average of about 10 to 20 nm.

3. The stent of claim 1, wherein the biostable layer has an average volume in the range of about 5,000 to 20,000 cubic micrometer per square millimeter of stent surface area.

4. The stent of any of claims 1-3, wherein the biostable layer comprises ceramic material.

5. The stent of claim 1, wherein the biostable layer comprises one or more metal oxides.

6. The stent of any of claims 1-3, wherein the biostable layer comprises a crystalline form of titanium oxide.

7. The stent of claim 1, wherein the biostable layer is on a surface of the stent.

8. The stent of claim 7, wherein the biostable layer is on an interior surface, an exterior surface or a sidewall.

9. The stent of claim 1, wherein at least a portion of the biostable layer is covered by a bioerodible layer.

10. The stent of claim 1, wherein the biostable layer formed by a sol-gel process.

11. The stent of claim 1, wherein the biostable layer is formed by a process comprising:
    modifying a selected portion of the surface of the underlying structure with hydroxyl groups;
    allowing the hydroxyl groups to react with one or more metal alkoxides to form a covalently-bound biostable layer of the one or more metal alkoxides;
    (optionally) removing excess adsorbed metal alkoxide; and
    hydrolyzing the covalently-bound surface of the biostable layer.

12. The stent of claim 1, wherein the biostable layer is a monolayer.

13. The stent of claim 1, comprising one or more monolayers of a metal oxide, an organic material, a polymeric material or a biological material.

14. The stent of claim 1, further comprising at least one therapeutic agent.

15. The stent of claim 14, wherein the therapeutic agent is paclitaxel.

16. A method comprising implanting the stent of claim 1 in a body passageway to stimulate the attachment of endothelial cells to the stent or control the erosion rate of the underlying structure.

17. The method of claim 16, wherein at least a portion of the stent degrades over a period of time inside the organism and releases a therapeutic agent.

18. The method of claim 16, wherein the stent is implanted in a cardiovascular passageway.

19. A stent comprising a biostable layer and a bioerodible underlying structure, wherein the biostable layer is about 5% or less of a wall thickness of a strut of the stent, wherein the bioerodible underlying structure comprises a bioerodible metal, wherein the biostable layer comprises one or more of titanium oxide, ruthenium oxide, or iridium oxide.

20. A stent comprising a biostable layer and a bioerodible underlying structure, wherein the biostable layer is about 5% or less of a wall thickness of a strut of the stent, wherein the biostable layer comprises a plurality of nodules about 15-20 nm in size.

21. The stent of claim 1, wherein the bioerodible underlying structure comprises magnesium or an alloy thereof.

* * * * *